(12) United States Patent
Suzuki

(10) Patent No.: US 10,208,131 B2
(45) Date of Patent: Feb. 19, 2019

(54) ARTIFICIALLY PRODUCED POLYCLONAL IMMUNOGLOBULIN PREPARATION

(71) Applicant: National University Corporation Chiba University, Chiba (JP)

(72) Inventor: Kazuo Suzuki, Chiba (JP)

(73) Assignee: National University Corporation Chiba University, Chiba (JP)

(*) Notice: Subject to any disclaimer, the term of this patent is extended or adjusted under 35 U.S.C. 154(b) by 124 days.

(21) Appl. No.: 13/716,469

(22) Filed: Dec. 17, 2012

(65) Prior Publication Data
US 2013/0164290 A1 Jun. 27, 2013

(30) Foreign Application Priority Data
Dec. 19, 2011 (JP) .................. 2011-277163

(51) Int. Cl.
*C07K 16/00* (2006.01)
*C07K 16/46* (2006.01)
*A61K 39/00* (2006.01)

(52) U.S. Cl.
CPC ............ *C07K 16/46* (2013.01); *C07K 16/00* (2013.01); *A61K 2039/505* (2013.01); *C07K 2317/51* (2013.01); *C07K 2317/53* (2013.01)

(58) Field of Classification Search
None
See application file for complete search history.

(56) References Cited

U.S. PATENT DOCUMENTS

2005/0260710 A1* 11/2005 Suzuki et al. .............. 435/69.1

FOREIGN PATENT DOCUMENTS

JP 2005312445 A 11/2005

OTHER PUBLICATIONS

Anthony et al. "Recapitulation of IVIG Anti-Inflammatory Activity with a Recombinant IgG Fc", Science vol. 320 Apr. 18, 2008, pp. 373-376.*
Wu et al.The Mystery of IVIg, , The Rheumatologist, Mar. 2012, pp. 1-11, http://www.the-rheumatologist.org/details/article/1532121/The_Mystery_of_IVIg.html, retrieved Aug. 23, 2013.*
Kallenberg, "Anti-neutrophil cytoplasmic antibody (ANCA)-associated vasculitis:where to go?" Clinical and Experimental Immunology 164 (Suppl. 1), 1-3, 2011.*
Loeffler et al., "Development of Antihuman IgG Antibodies and Hematologic Deficits but Not Clinical Abnormalities in C57BL/6 Mice after Repeated Administration of Human Intravenous Immunoglobulin", Comparative Medicine 62:31-36, 2012.*
Katz et al. (Curr Pharm Des. 2011;17(29):3166-75). (Year: 2011).*
Rezaei et al. (Expert Rev Clin Innnnunol. May 2011;7(3):301-16)). (Year: 2011).*
Hamano et al., "Genetic Dissection of Vasculitis, Myeloperoxidase-Specific Antineutrophil Cytoplasmic Autoantibody Production, and Related Traits in Spontaneous Crescentic Glomerulonephritis-Forming/Kinjoh Mice," The Journal of Immunology, vol. 176, 2006, pp. 3662-3673.
Hoshino et al., "MPO-ANCA induces IL-17 production by activated neutrophils in vitro via classical complement pathway-dependent manner," Journal of Autoimmunity, vol. 31, 2008, pp. 79-89.
Hoshino et al., "Trafficking of QD-Conjugated MPO-ANCA in Murine Systemic Vasculitis and Glomerulonephritis Model Mice," Microbiol. Immunol., vol. 51, No. 5, 2007, pp. 551-566.
Ishida-Okawara et al., "Neutrophil contribution to the crescentic glomerulonephritis in SCG/Kj mice," Nephrology Dialysis Transplantation, vol. 19, No. 7, 2004, pp. 1708-1715.
Kinjoh et al., "Genetic selection for crescent formation yields mouse strain with rapidly progressive glomerulonephritis and small vessel vasculitis," Proc. Natl. Acad. Sci., vol. 90, Apr. 1993, pp. 3413-3417.
Nagao et al., "Direct activation of glomerular endothelial cells by anti-moesin activity of anti-myeloperoxidase antibody," Nephrology Dialysis Transplantation, vol. 26, 2011, pp. 2752-2760.
Nagao et al., Up-regulation of adhesion molecule expression in glomerular endothelial cells by anti-myeloperoxidase antibody, Nephrology Dialysis Transplantation, vol. 22, 2007, pp. 77-87.
Tomizawa et al., "Reduction of MPO-ANCA epitopes in SCG/Kj mice by 15-deoxyspergualin treatment restricted by IgG2b associated with crescentic glomerulonephritis," Rheumatology, vol. 49, 2010, pp. 1245-1256.

* cited by examiner

*Primary Examiner* — Zachary S Skelding
(74) *Attorney, Agent, or Firm* — Kilyk & Bowersox, P.L.L.C.

(57) ABSTRACT

The present invention intended to provide an artificial polyclonal immunoglobulin composition having a high therapeutic effect and high safety, and being capable of stable supply in a large amount. Specifically provided is an artificial polyclonal immunoglobulin composition containing, as active ingredients, 204 polypeptides represented by amino acid sequences set forth in SEQ ID NOS: 1 to 204 of the sequence listing, the polypeptides being plural kinds of single chain variable fragments (also referred to as ScFvs) each comprised of a heavy chain variable region, heavy chain constant region 1, and hinge region (VH-CH1-hinge) of an immunoglobulin, in which the heavy chain variable regions are different each other.

5 Claims, 5 Drawing Sheets
Specification includes a Sequence Listing.

Figure 5-A
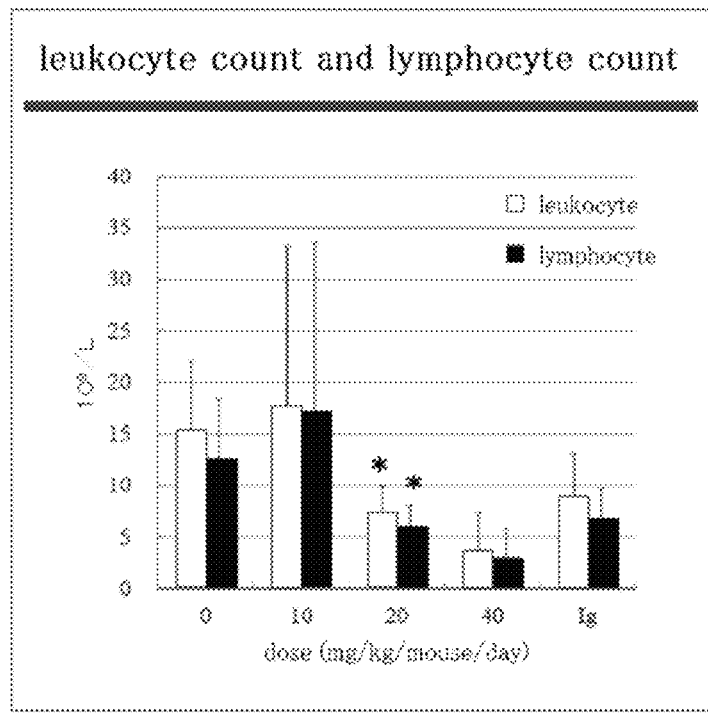
Figure 5-B
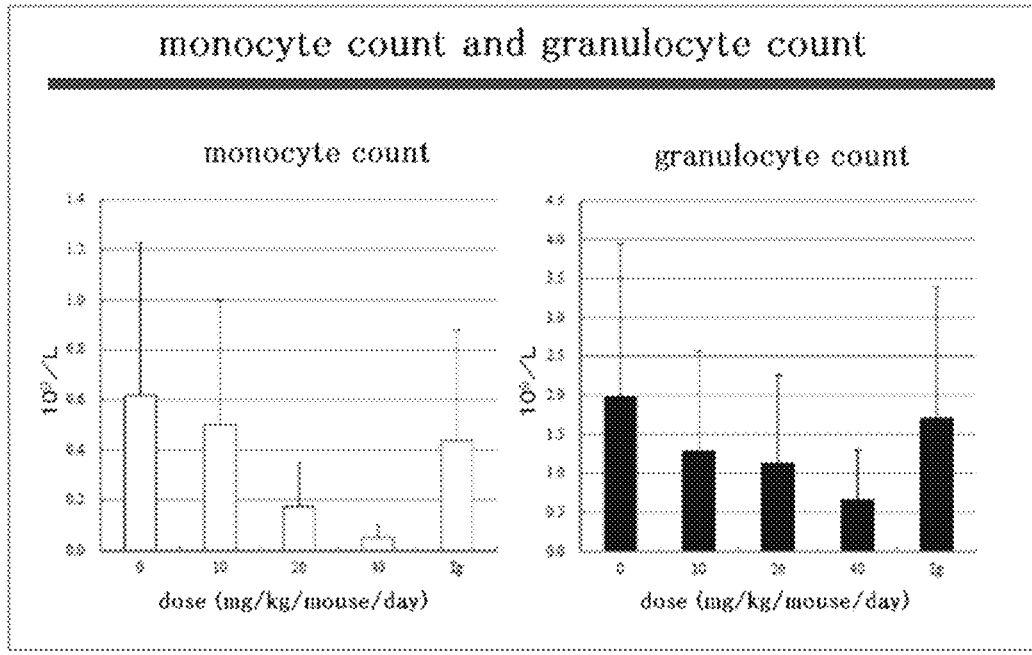

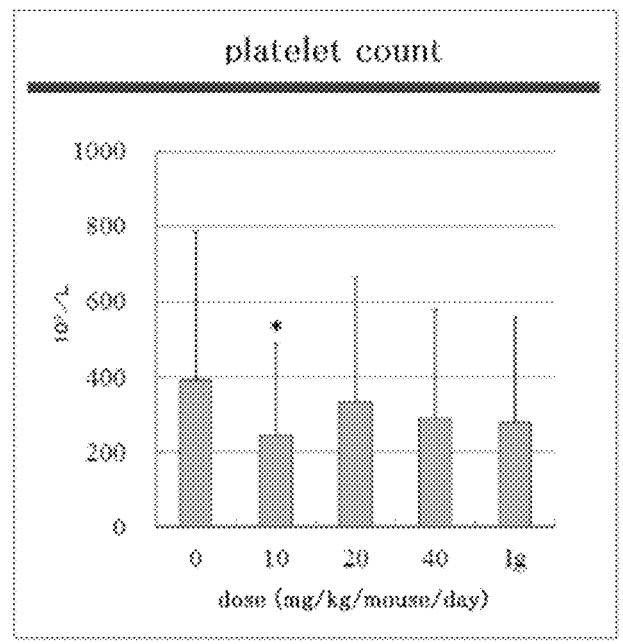

SEQUENCE LISTING

<160> NUMBER OF SEQ ID NOS: 204

<210> SEQ ID NO 1
<211> LENGTH: 275
<212> TYPE: PRT
<213> ORGANISM: homosapiens

<400> SEQUENCE: 1

Met Glu Phe Gly Leu Ser Trp Val Phe Leu Val Ala Ile Phe Glu Gly
1               5                   10                  15

Val Gln Cys Glu Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Ala Met His Trp Val Arg Gln Ala Pro Gly Lys Gly Leu
    50                  55                  60

Glu Trp Val Ala Val Ile Ser Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Asp Val Tyr Gly Asp Asp Gly Pro Leu Gly

```
            115                 120                 125
Tyr Trp Gly Gln Gly Thr Leu Val Thr Val Ser Ser Ala Ser Thr Lys
        130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Val Thr His His His
            260                 265                 270

His His His
        275

<210> SEQ ID NO 2
<211> LENGTH: 280
<212> TYPE: PRT
<213> ORGANISM: homosapiens

<400> SEQUENCE: 2

Met Glu Phe Gly Leu Ser Trp Leu Phe Leu Val Ala Leu Leu Lys Gly
1               5                   10                  15

Val Gln Cys Glu Glu Phe Leu Leu Glu Ser Gly Gly Gly Leu Val Arg
            20                  25                  30

Pro Gly Gly Ser Leu Arg Leu Ser Cys Ala Thr Ser Gly Phe Arg Phe
        35                  40                  45

Arg Asp His Thr Met Ala Trp Val Arg Gln Ala Pro Gly Lys Gly Leu
    50                  55                  60

Glu Trp Ile Ser Val Ser Ser Asp Ala Asp Asn Gly Asn Thr Tyr Tyr
65                  70                  75                  80

Tyr Ala Asp Ser Val Arg Gly Arg Phe Thr Val Ser Arg Asp Asn Ser
                85                  90                  95

Met Asn Thr Val His Leu Gln Met Asp Ile Leu Arg Val Asp Asp Thr
            100                 105                 110

Ala Val Tyr Phe Cys Ala Arg Glu Gly Met Trp Gln Val Gly Tyr Trp
        115                 120                 125

Tyr Phe Asn Leu Trp Gly Arg Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

```
Ser Ser Val Val Thr Val Pro Ser Ser Asn Phe Gly Thr Gln Thr Tyr
    210                 215                 220
Thr Cys Asn Val Asp His Lys Pro Ser Asn Thr Lys Val Asp Lys Thr
225                 230                 235                 240
Val Glu Arg Lys Cys Cys Val Glu Cys Pro Pro Cys Pro Ala Pro Pro
                245                 250                 255
Val Ala Gly Pro Ser Val Phe Leu Phe Pro Pro Lys Pro Lys Asp Thr
            260                 265                 270
His His His His His His His
        275                 280

<210> SEQ ID NO 3
<211> LENGTH: 280
<212> TYPE: PRT
<213> ORGANISM: homosapiens

<400> SEQUENCE: 3

Met Pro Met Glu Phe Gly Leu Ser Trp Val Phe Leu Val Ala Leu Leu
1               5                   10                  15
Arg Gly Val Gln Cys Gln Val Gln Leu Val Glu Ser Gly Gly Gly Val
            20                  25                  30
Val Gln Pro Gly Arg Ser Leu Arg Leu Ser Cys Ala Ala Ser Gly Phe
        35                  40                  45
Ser Phe Ser Thr Tyr Ala Met His Trp Val Arg Gln Ala Pro Gly Met
    50                  55                  60
Gly Leu Glu Trp Val Ala Val Met Ser Tyr Asp Gly Thr Thr Glu Tyr
65                  70                  75                  80
Ile Ala Asp Ser Val Lys Gly Arg Phe Thr Ile Ser Arg Asp Asn Ser
                85                  90                  95
Lys Asn Thr Leu Tyr Met Gln Met Asn Ser Leu Arg Pro Glu Asp Thr
            100                 105                 110
Ala Val Tyr Tyr Cys Ala Arg Asn Gly Val Pro Tyr Tyr Ala Ser Gly
        115                 120                 125
Gly Gly Trp Ile Asp Pro Trp Gly Gln Gly Thr Pro Val Thr Val Ser
    130                 135                 140
Ser Ala Ser Thr Lys Gly Pro Ser Val Phe Pro Leu Ala Pro Cys Ser
145                 150                 155                 160
Arg Ser Thr Ser Glu Ser Thr Ala Ala Leu Gly Cys Leu Val Lys Asp
                165                 170                 175
Tyr Phe Pro Glu Pro Val Thr Val Ser Trp Asn Ser Gly Ala Leu Thr
            180                 185                 190
Ser Gly Val His Thr Phe Pro Ala Val Leu Gln Ser Ser Gly Leu Tyr
        195                 200                 205
Ser Leu Ser Ser Val Val Thr Val Pro Ser Ser Asn Phe Gly Thr Gln
    210                 215                 220
Thr Tyr Thr Cys Asn Val Asp His Lys Pro Ser Asn Thr Lys Val Asp
225                 230                 235                 240
Lys Thr Val Glu Arg Lys Cys Cys Val Glu Cys Pro Pro Cys Pro Ala
                245                 250                 255
Pro Pro Val Ala Gly Pro Ser Val Phe Leu Phe Pro Pro Lys Pro Lys
            260                 265                 270
Asp Thr His His His His His His
        275                 280

<210> SEQ ID NO 4
```

<211> LENGTH: 273
<212> TYPE: PRT
<213> ORGANISM: homosapiens

<400> SEQUENCE: 4

```
Met Glu Phe Gly Leu Ser Trp Val Leu Leu Val Ala Ile Leu Glu Gly
1               5                   10                  15

Val Gln Cys Glu Val Asp Leu Val Glu Ser Gly Gly Gly Leu Val Gln
            20                  25                  30

Pro Gly Gly Ser Leu Arg Leu Ser Cys Val Ala Ser Gly Phe Ser Leu
        35                  40                  45

Ser Val Tyr Asn Met Asn Trp Leu Arg Gln Ala Pro Gly Lys Gly Leu
    50                  55                  60

Glu Trp Val Ala Ser Ile Trp Ser Asp Gly Ser Gln Thr Tyr Tyr Ala
65                  70                  75                  80

Gly Ser Val Arg Gly Arg Phe Thr Ile Ser Lys Asp Asn Ser Gln Asn
                85                  90                  95

Thr Leu Ser Leu Gln Met Asn Arg Leu Arg Gly Glu Asp Thr Ala Leu
            100                 105                 110

Tyr Phe Cys Val Gly Glu Pro Met His Gly Arg Tyr Phe Asn Leu Trp
        115                 120                 125

Gly Arg Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Gln Pro Val Ala Gly Pro Ser
                245                 250                 255

Val Phe Leu Phe Pro Pro Lys Pro Lys Asp Thr His His His His His
            260                 265                 270

His
```

<210> SEQ ID NO 5
<211> LENGTH: 222
<212> TYPE: PRT
<213> ORGANISM: homosapiens

<400> SEQUENCE: 5

```
Met Tyr Trp Val Arg Gln Ala Pro Asp Lys Gly Leu Glu Trp Val Ala
1               5                   10                  15

Val Ile Ser Tyr Asp Ser Ile Asp Lys Arg Tyr Ala Asn Ser Val Lys
            20                  25                  30

Gly Arg Phe Thr Ile Ser Arg Asp Asn Ser Arg Ser Thr Leu Tyr Leu
        35                  40                  45

Gln Met Asn Ser Leu Arg Pro Glu Asp Thr Gly Val Tyr Tyr Cys Gly
    50                  55                  60
```

```
Asp Thr Gly Gly Leu Glu Gln Trp Leu Val Arg Tyr Trp Gly Gln Gly
 65                  70                  75                  80

Thr Pro Val Ile Val Ser Ser Ala Ser Thr Lys Gly Pro Ser Val Phe
             85                  90                  95

Pro Leu Ala Pro Cys Ser Arg Ser Thr Ser Glu Ser Thr Ala Ala Leu
            100                 105                 110

Gly Cys Leu Val Lys Asp Tyr Phe Pro Glu Pro Val Thr Val Ser Trp
        115                 120                 125

Asn Ser Gly Ala Leu Thr Ser Gly Val His Thr Phe Pro Ala Val Leu
    130                 135                 140

Gln Ser Ser Gly Leu Tyr Ser Leu Ser Ser Val Val Thr Val Pro Ser
145                 150                 155                 160

Ser Asn Phe Gly Thr Gln Thr Tyr Thr Cys Asn Val Asp His Lys Pro
                165                 170                 175

Ser Asn Thr Lys Val Asp Lys Thr Val Glu Arg Lys Cys Cys Val Glu
            180                 185                 190

Cys Pro Pro Cys Pro Ala Pro Pro Val Ala Gly Pro Ser Val Phe Leu
        195                 200                 205

Phe Pro Pro Lys Pro Lys Asp Thr His His His His His His
    210                 215                 220

<210> SEQ ID NO 6
<211> LENGTH: 281
<212> TYPE: PRT
<213> ORGANISM: homosapiens

<400> SEQUENCE: 6

Met Glu Phe Gly Leu Ser Trp Leu Phe Leu Val Ala Ile Leu Lys Gly
  1               5                  10                  15

Val Gln Cys Glu Val His Leu Met Glu Ser Gly Gly Gly Leu Gly Gln
             20                  25                  30

Pro Gly Gly Ser Leu Arg Leu Ser Cys Thr Ala Ser Gly Phe Thr Phe
         35                  40                  45

Asn Asn Cys Trp Ile His Trp Val Arg Gln Ala Pro Gly Lys Gly Leu
    50                  55                  60

Val Trp Val Ser Ser Ile Asn Thr Asp Ala Thr Thr Thr Thr Tyr Ala
 65                  70                  75                  80

Asp Ser Val Lys Gly Arg Phe Thr Ile Ser Arg Asp Asn Ala Arg Asn
             85                  90                  95

Thr Val Phe Leu Glu Val Asn Ser Leu Thr Lys Glu Asp Thr Ala Val
            100                 105                 110

Tyr Tyr Cys Ala Arg Asp Arg Cys Met Ser Gly Arg Cys Ser Tyr Asp
        115                 120                 125

Phe Ser Asp Gly Met Asp Val Trp Gly Gln Gly Thr Thr Val Ile Val
    130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
    210                 215                 220
```

```
Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
            245                 250                 255

Ala Pro Pro Val Ala Gly Pro Ser Val Phe Leu Phe Pro Pro Lys Pro
        260                 265                 270

Lys Asp Thr His His His His His His
        275                 280
```

<210> SEQ ID NO 7
<211> LENGTH: 282
<212> TYPE: PRT
<213> ORGANISM: homosapiens

<400> SEQUENCE: 7

```
Met Glu Leu Gly Leu Ser Trp Ile Ser Leu Ala Ile Leu Lys Gly
1               5                   10                  15

Val Gln Cys Glu Val Gln Leu Val Glu Ser Gly Gly Ala Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Val Pro Gly Lys Gly Leu
50                  55                  60

Glu Trp Val Ala Gly Ile Ser Leu Asn Ser Gly Lys Met Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Pro Glu Asp Thr Ala Leu
            100                 105                 110

Tyr Tyr Cys Ala Lys Asp Lys Gly Gly Arg Tyr Gly Ser Gly Thr
        115                 120                 125

Tyr Tyr Ala Glu Tyr Phe Gln His Trp Gly Gln Gly Thr Leu Val Ile
        130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Asn Phe Gly
        210                 215                 220

Thr Gln Thr Tyr Thr Cys Asn Val Asp His Lys Pro Ser Asn Thr Lys
225                 230                 235                 240

Val Asp Lys Thr Val Glu Arg Lys Cys Cys Val Glu Cys Pro Pro Cys
                245                 250                 255

Pro Ala Pro Pro Val Ala Gly Pro Ser Val Phe Leu Phe Pro Pro Lys
            260                 265                 270

Pro Lys Asp Thr His His His His His His
        275                 280
```

<210> SEQ ID NO 8
<211> LENGTH: 313
<212> TYPE: PRT

<213> ORGANISM: homosapiens

<400> SEQUENCE: 8

```
Met Glu Phe Gly Leu Ser Trp Val Phe Leu Val Ala Leu Leu Arg Gly
1               5                   10                  15
Val Gln Cys Gln Val His Leu Val Glu Ser Gly Gly Gly Val Val Gln
            20                  25                  30
Pro Arg Arg Ser Leu Arg Leu Ser Cys Ala Ala Ser Gly Phe Ser Phe
        35                  40                  45
Asn Ile Tyr Ala Met His Trp Val Arg Gln Ala Pro Gly Lys Gly Leu
    50                  55                  60
Glu Trp Val Ala Gly Ile Ser Ser Asp Gly Asp Thr Arg Glu Ala
65                  70                  75                  80
Gly Ser Leu Gln Gly Arg Phe Thr Ile Ser Arg Asp Asn Ser Lys Ser
                85                  90                  95
Ile Val Tyr Leu Gln Met Asn Ser Leu Thr Leu Asp Asp Thr Ala Phe
            100                 105                 110
Tyr Tyr Cys Val Arg Ser Gln Gln Ser Ser Arg Phe Asp Trp Gln Leu
        115                 120                 125
Ser Asp Tyr Trp Gly Gln Gly Thr Leu Val Thr Val Ser Ser Ala Ser
    130                 135                 140
Thr Lys Gly Pro Ser Val Phe Pro Leu Ala Pro Cys Ser Arg Ser Thr
145                 150                 155                 160
Ser Glu Ser Thr Ala Ala Met Gly Cys Leu Val Lys Asp Tyr Phe Pro
                165                 170                 175
Glu Pro Val Thr Val Ser Trp Asn Ser Gly Ala Leu Thr Ser Gly Val
            180                 185                 190
His Thr Phe Pro Ala Val Leu Gln Ser Ser Gly Leu Tyr Ser Leu Ser
        195                 200                 205
Ser Val Val Thr Val Pro Ser Ser Asn Phe Gly Thr Gln Thr Tyr Thr
    210                 215                 220
Cys Asn Val Asn His Lys Pro Ser Asn Thr Lys Val Asp Lys Arg Val
225                 230                 235                 240
Glu Leu Lys Thr Pro Leu Gly Asp Thr Thr His Thr Cys Pro Arg Cys
                245                 250                 255
Pro Glu Pro Lys Ser Cys Asp Thr Pro Pro Phe Pro Arg Cys Pro
            260                 265                 270
Glu Pro Lys Ser Cys Asp Thr Pro Pro Cys Pro Arg Cys Pro Ala
        275                 280                 285
Pro Glu Leu Leu Gly Gly Pro Ser Val Phe Leu Phe Pro Pro Lys Pro
    290                 295                 300
Lys Asp Ala His His His His His
305                 310
```

<210> SEQ ID NO 9
<211> LENGTH: 276
<212> TYPE: PRT
<213> ORGANISM: homosapiens

<400> SEQUENCE: 9

```
Met Glu Phe Gly Leu Ser Trp Val Phe Leu Val Ala Ile Leu Glu Gly
1               5                   10                  15
Val Gln Cys Glu Val Gln Leu Val Glu Ser Gly Gly Gly Leu Val Lys
            20                  25                  30
Pro Gly Gly Ser Leu Arg Leu Ser Cys Ala Ala Ser Gly Ser Arg Phe
```

```
                    35                  40                  45
Ser Tyr Tyr Tyr Met Asn Trp Leu Arg Gln Ala Pro Gly Lys Gly Leu
 50                  55                  60

Glu Trp Val Ser Tyr Ile Gly Tyr Thr Thr Asp Ala Ile Leu Tyr Ser
 65                  70                  75                  80

Asp Ser Val Lys Gly Arg Phe Thr Val Ser Arg Asp Asn Ala Lys Asn
                 85                  90                  95

Ser Leu Tyr Leu Gln Met Asn Ser Leu Lys Ser Glu Asp Thr Ala Val
            100                 105                 110

Tyr Phe Cys Ser Arg Asp Leu Gly Tyr Arg Gly Ser Tyr Thr Ala Phe
            115                 120                 125

Asp Leu Trp Gly Gln Gly Thr Met Val Thr Val Ser Ser Ala Ser Thr
            130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Asn Phe Gly Thr Gln Thr Tyr Thr Cys
            210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr His His
            260                 265                 270

His His His His
        275

<210> SEQ ID NO 10
<211> LENGTH: 282
<212> TYPE: PRT
<213> ORGANISM: homosapiens

<400> SEQUENCE: 10

Met Glu Phe Gly Leu Ser Trp Val Phe Leu Val Ala Leu Leu Arg Gly
 1               5                  10                  15

Val Gln Cys Gln Val Gln Leu Val Glu Ser Gly Gly Gly Val Val Gln
             20                  25                  30

Pro Gly Gly Ser Leu Arg Leu Ser Cys Thr Ala Ser Gly Phe Thr Phe
         35                  40                  45

Ser Asp Tyr Asp Met Tyr Trp Val Arg Gln Ala Pro Arg Lys Gly Leu
 50                  55                  60

Glu Gly Val Ala Leu Ile Ser Ser Asp Glu Ser Asn Lys Tyr Tyr Ala
 65                  70                  75                  80

Glu Ser Val Lys Gly Arg Phe Thr Ile Ser Arg Asp Asn Ser Lys Asn
                 85                  90                  95

Ser Leu Tyr Leu Arg Leu Asn Ser Leu Arg Ala Glu Asp Thr Ala Val
            100                 105                 110

Tyr Tyr Cys Ala Arg Val Glu Thr Ser Tyr Tyr Asp Ile Asp His Tyr
            115                 120                 125
```

```
Tyr Gly His Asp Ala Leu Asp Ile Trp Gly Gln Gly Thr Met Val Thr
    130                 135                 140
Val Ser Ser Ala Ser Thr Lys Gly Pro Ser Val Phe Pro Leu Ala Pro
145                 150                 155                 160
Ser Ser Lys Ser Thr Ser Gly Gly Thr Ala Ala Leu Gly Cys Leu Val
                165                 170                 175
Lys Asp Tyr Phe Pro Glu Pro Val Thr Val Ser Trp Asn Ser Gly Ala
            180                 185                 190
Leu Thr Ser Gly Val His Thr Phe Pro Ala Val Leu Gln Ser Ser Gly
        195                 200                 205
Leu Tyr Ser Leu Ser Ser Val Val Thr Val Pro Ser Ser Ser Leu Gly
    210                 215                 220
Thr Gln Thr Tyr Ile Cys Asn Val Asn His Lys Pro Ser Asn Thr Lys
225                 230                 235                 240
Val Asp Lys Thr Val Glu Arg Lys Cys Cys Val Glu Cys Pro Pro Cys
                245                 250                 255
Pro Ala Pro Pro Val Ala Gly Pro Ser Val Phe Leu Phe Pro Pro Lys
            260                 265                 270
Pro Lys Asp Thr His His His His His His
        275                 280

<210> SEQ ID NO 11
<211> LENGTH: 224
<212> TYPE: PRT
<213> ORGANISM: homosapiens

<400> SEQUENCE: 11

Met His Trp Val Arg Gln Thr Pro Gly Lys Gly Leu Glu Trp Val Ser
1               5                   10                  15
Gly Ile Thr Trp Asn Ser Asp Gly Ile Asp Tyr Ala Asp Ser Val Lys
                20                  25                  30
Gly Arg Phe Thr Ile Ser Arg Asp Asn Pro Lys Asn Ser Leu Phe Leu
            35                  40                  45
Gln Met Asn Gly Leu Arg Thr Glu Asp Thr Ala Leu Tyr Phe Cys Ala
        50                  55                  60
Lys Asp Ile Thr Met Val Arg Gln Trp Arg Ala Leu His Ile Trp Gly
65                  70                  75                  80
Gln Gly Thr Arg Val Thr Val Ser Phe Ala Ser Thr Lys Gly Pro Ser
                85                  90                  95
Val Phe Pro Leu Ala Pro Cys Ser Arg Ser Thr Ser Glu Ser Thr Ala
            100                 105                 110
Ala Leu Gly Cys Leu Val Lys Asp Tyr Phe Pro Glu Pro Val Thr Val
        115                 120                 125
Ser Trp Asn Ser Gly Ala Leu Thr Ser Gly Val His Thr Phe Pro Pro
    130                 135                 140
Val Leu Gln Ser Ser Gly Leu Tyr Ser Leu Ser Ser Val Val Thr Val
145                 150                 155                 160
Pro Ser Ser Asn Phe Gly Thr Gln Thr Tyr Thr Cys Asn Val Asp His
                165                 170                 175
Lys Pro Ser Asn Thr Lys Val Asp Lys Thr Val Glu Arg Lys Cys Cys
            180                 185                 190
Val Glu Cys Pro Pro Cys Pro Ala Pro Pro Val Ala Gly Pro Ser Val
        195                 200                 205
Phe Leu Phe Pro Pro Lys Pro Lys Asp Thr His His His His His His
    210                 215                 220
```

<210> SEQ ID NO 12
<211> LENGTH: 274
<212> TYPE: PRT
<213> ORGANISM: homosapiens

<400> SEQUENCE: 12

Met Glu Phe Gly Leu Ser Trp Ile Phe Leu Ala Ala Ile Leu Lys Gly
1               5                   10                  15

Val Gln Cys Glu Val Gln Leu Leu Glu Ser Gly Gly Asp Leu Val Gln
            20                  25                  30

Pro Gly Gly Ser Leu Arg Leu Ser Cys Ala Ala Ser Gly Phe Thr Phe
        35                  40                  45

Ser Asn Tyr Ala Met Thr Trp Val Arg Gln Ala Pro Gly Lys Gly Leu
    50                  55                  60

Glu Trp Val Ser Thr Thr Ser Gly Ser Gly Ala Asn Thr Tyr Tyr Ala
65                  70                  75                  80

Asp Ser Val Lys Gly Arg Phe Thr Ser Arg Asp Asn Ser Lys Asn
                85                  90                  95

Thr Leu Tyr Leu Gln Met Asn Ser Leu Arg Ala Asp Thr Ala Val
            100                 105                 110

Tyr Phe Cys Ala Lys Met Thr Thr Val Val Leu Glu Ser Ile Asp Ser
        115                 120                 125

Trp Gly Gln Gly Thr Leu Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Val Ala Gly Pro
                245                 250                 255

Ser Val Phe Leu Phe Pro Pro Lys Pro Lys Asp Thr His His His His
            260                 265                 270

His His

<210> SEQ ID NO 13
<211> LENGTH: 278
<212> TYPE: PRT
<213> ORGANISM: homosapiens

<400> SEQUENCE: 13

Met Glu Phe Gly Leu Ser Trp Val Phe Leu Val Ala Ile Phe Lys Gly
1               5                   10                  15

Val Gln Cys Glu Glu Pro Leu Val Glu Ser Gly Gly Gly Leu Val Gln
            20                  25                  30

Pro Gly Gly Ser Leu Arg Leu Ser Cys Val Ala Ser Glu Val Tyr Gly
        35                  40                  45

Phe Thr Phe Ser Gly Ser Gly Met His Trp Val Arg Gln Ala Pro Gly
    50                  55                  60

Lys Gly Leu Glu His Val Ala Ala Ile Ile Ser Tyr Gly Gly Ile Thr
65                  70                  75                  80

Tyr Tyr Ala Asn Ser Val Glu Gly Arg Phe Ile Ile Ser Arg Asp Asn
                85                  90                  95

Ser Lys Asn Ile Leu Tyr Leu Gln Met Gly Ser Leu Arg Pro Glu Asp
                100                 105                 110

Thr Ala Ile Tyr Tyr Cys Ala Arg Asp Gly Pro Gly Ile Trp Gly
                115                 120                 125

Ala Phe Asp Phe Trp Gly Gln Gly Thr Val Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
    195                 200                 205

Ser Ser Val Val Thr Val Pro Ser Ser Asn Phe Gly Thr Gln Thr Tyr
210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Val Thr
                260                 265                 270

His His His His His His
        275

<210> SEQ ID NO 14
<211> LENGTH: 278
<212> TYPE: PRT
<213> ORGANISM: homosapiens

<400> SEQUENCE: 14

Met Glu Phe Glu Leu Ser Trp Val Phe Leu Val Thr Leu Leu Arg Gly
1               5                   10                  15

Val Gln Cys Gln Val Ser Leu Glu Glu Ser Gly Gly Ala Val Val His
                20                  25                  30

Pro Gly Asn Ser Leu Arg Leu Ser Cys Ser Ala Ser Gly Leu Gly Phe
                35                  40                  45

Asn Thr Tyr Ala Met His Trp Ala Arg Gln Ala Pro Gly Arg Gly Pro
    50                  55                  60

Glu Trp Val Ala Gly Ile Ser Phe Asp Glu Phe His Arg Glu Tyr Ala
65                  70                  75                  80

Asp Ala Val Arg Gly Arg Phe Thr Val Ser Arg Gly Ser Ser Lys Asn
                85                  90                  95

Ile Leu Leu Leu Gln Met Glu Gly Leu Thr Ala Glu Asp Thr Ala Val
                100                 105                 110

Tyr Tyr Cys Thr Leu Ser Gln Thr Glu Ser Glu Ser Asp Ile Phe Asn
            115                 120                 125

Gly Leu Asp Tyr Trp Gly Arg Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
            165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Asn Phe Gly Thr Gln Thr Tyr
        210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Gln Pro
                245                 250                 255

Val Ala Gly Pro Ser Val Phe Leu Phe Pro Pro Lys Pro Lys Asp Thr
            260                 265                 270

His His His His His His
            275

<210> SEQ ID NO 15
<211> LENGTH: 276
<212> TYPE: PRT
<213> ORGANISM: homosapiens

<400> SEQUENCE: 15

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
            35                  40                  45

Ser Ser Phe Ala Met Ser Trp Val Arg Gln Ala Pro Ala Lys Gly Leu
    50                  55                  60

Glu Trp Val Ser Ala Ile Ser Gly Ser Gly Gly Thr Thr Ser Tyr Thr
65                  70                  75                  80

Ser Tyr Ala Asp Ser Val Lys Gly Arg Phe Thr Ile Ser Arg Asp Asn
                85                  90                  95

Ser Lys Asn Thr Leu Tyr Val Gln Met Asn Ser Leu Arg Ala Glu Asp
            100                 105                 110

Thr Ala Ile Tyr Tyr Cys Val Lys Glu Ser Ser Gly Gly Thr Thr Leu
            115                 120                 125

Glu Tyr Trp Gly Gln Gly Thr Leu Val Thr Val Ser Ser Ala Ser Thr
        130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Asn Phe Gly Thr Gln Thr Tyr Thr Cys
        210                 215                 220

Asn Val Asp His Lys Pro Ser Asn Thr Lys Val Asp Lys Thr Val Glu

```
                225                 230                 235                 240
Arg Lys Cys Cys Val Glu Cys Pro Pro Cys Pro Ala Pro Pro Val Ala
                    245                 250                 255

Gly Pro Ser Val Phe Leu Phe Pro Pro Lys Pro Lys Asp Thr His His
                260                 265                 270

His His His His
        275

<210> SEQ ID NO 16
<211> LENGTH: 277
<212> TYPE: PRT
<213> ORGANISM: homosapiens

<400> SEQUENCE: 16

Met Asn Phe Gly Leu Ser Trp Val Phe Leu Val Ala Leu Leu Arg Gly
1               5                   10                  15

Val Gln Cys Gln Val Leu Leu Val Gln Ser Gly Gly Gly Val Val Gln
            20                  25                  30

Pro Gly Arg Ser Leu Arg Leu Ser Cys Ala Ala Ser Glu Phe Thr Phe
        35                  40                  45

Ser Asn Tyr Gly Val His Trp Val Arg Gln Ala Pro Gly Lys Gly Leu
    50                  55                  60

Glu Trp Val Ala Gly Ile Ser Ser Asp Gly Thr Asn Arg Ile His Ala
65                  70                  75                  80

Asp Ser Leu Glu Gly Arg Phe Ala Ile Ser Arg Asp Asn Ser Glu Asn
                85                  90                  95

Lys Val Tyr Leu Gln Met Asn Ser Leu Arg Val Gln Asp Thr Ala Val
            100                 105                 110

Tyr Tyr Cys Val Arg Ser Gln Gln Pro Ser Phe Phe Asp Trp Leu Phe
        115                 120                 125

Ser Asp Tyr Trp Gly Gln Gly Thr Leu Val Ala Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Gln
            260                 265                 270

His His His His His
        275

<210> SEQ ID NO 17
<211> LENGTH: 273
<212> TYPE: PRT
<213> ORGANISM: homosapiens
```

<400> SEQUENCE: 17

```
Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ala Leu
        35                  40                  45

Arg Asn Ser His Met His Trp Val Arg Gln Ala Ala Gly Lys Gly Leu
    50                  55                  60

Glu Trp Val Ala His Thr Arg Arg Ala Asp Asp Asn Tyr Ala Thr Met
65                  70                  75                  80

Tyr Val Ala Ser Val Lys Gly Arg Phe Thr Ile Ser Arg Asp Glu Ser
                85                  90                  95

Arg Asn Val Val Tyr Leu Gln Met Asn Arg Leu Thr Gly Glu Asp Thr
            100                 105                 110

Ala Val Tyr Tyr Cys Thr Arg Gln Thr Asn Ser Val His Asp Tyr Trp
        115                 120                 125

Gly Gln Gly Ile Val Val Thr Val Ser Ser Ala Ser Thr Lys Gly Pro
    130                 135                 140

Ser Val Phe Pro Leu Ala Pro Cys Ser Arg Ser Thr Ser Glu Asn Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr His His His His His
            260                 265                 270

His
```

<210> SEQ ID NO 18
<211> LENGTH: 272
<212> TYPE: PRT
<213> ORGANISM: homosapiens

<400> SEQUENCE: 18

```
Met Asp Phe Gly Leu Ser Trp Leu Phe Leu Val Ala Phe Leu Lys Gly
1               5                   10                  15

Val Gln Cys Glu Val Gln Leu Leu Glu Ser Gly Gly Gly Leu Val Gln
            20                  25                  30

Pro Gly Glu Ser Leu Arg Leu Ser Cys Ala Gly Ser Gly Phe Thr Phe
        35                  40                  45

Ser Thr Phe Val Met Thr Trp Val Arg Gln Ala Pro Gly Lys Gly Leu
    50                  55                  60

Glu Trp Val Ser Thr Ile Ser Pro Gly Asn Gly Ile Pro Tyr Tyr Ala
65                  70                  75                  80

Asp Ser Val Lys Gly Arg Phe Thr Ile Ser Arg Asp Asn Arg Lys Asn
```

```
                85                  90                  95
Thr Val Tyr Leu Gln Met Asn Ser Leu Arg Leu Asp Asp Thr Ala Val
            100                 105                 110
Tyr Phe Cys Ala Gly Gly Ser Gly Asp Tyr Phe Glu Gln His Trp Gly
            115                 120                 125
Gln Gly Asn Leu Val Ala Val Ser Ser Ala Ser Thr Lys Gly Pro Ser
        130                 135                 140
Val Phe Pro Leu Ala Pro Cys Ser Arg Ser Thr Ser Glu Asn Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
            195                 200                 205
Pro Ser Ser Asn Phe Gly Thr Gln Thr Tyr Thr Cys Asn Val Asp His
        210                 215                 220
Lys Pro Ser Asn Thr Lys Val Asp Lys Thr Val Glu Arg Lys Cys Cys
225                 230                 235                 240
Val Glu Cys Pro Pro Cys Pro Ala Pro Pro Val Ala Gly Pro Ser Val
                245                 250                 255
Phe Leu Phe Pro Pro Lys Pro Lys Asp Thr His His His His His His
            260                 265                 270

<210> SEQ ID NO 19
<211> LENGTH: 279
<212> TYPE: PRT
<213> ORGANISM: homosapiens

<400> SEQUENCE: 19

Met Glu Phe Gly Leu Ser Trp Leu Phe Leu Val Ala Ile Leu Lys Gly
1               5                   10                  15
Val Gln Cys Glu Val Gln Leu Leu Glu Ser Gly Gly Ala Leu Val Gln
            20                  25                  30
Pro Gly Gly Ser Leu Arg Leu Ser Cys Ala Ala Ser Gly Phe Thr Leu
        35                  40                  45
Ser Ala His Ala Met Ser Trp Val Arg Gln Ala Pro Gly Lys Gly Leu
    50                  55                  60
Glu Trp Val Ser Val Ile Arg Gly Arg Ser Asp Thr Thr His Tyr Ala
65                  70                  75                  80
Asp Ser Val Lys Gly Arg Phe Thr Ile Ser Arg Asp Asp Ser Lys Asn
                85                  90                  95
Thr Leu Tyr Leu Gln Met Asn Ser Leu Arg Ala Glu Asp Thr Ala Leu
            100                 105                 110
Tyr Tyr Cys Ala Lys Asn Asn Pro Tyr Gly Thr Gly Trp Ala Gly Trp
            115                 120                 125
Phe Asp Pro Trp Gly Gln Gly Thr Leu Val Thr Val Ser Ser Ala Ser
        130                 135                 140
Thr Lys Gly Pro Ser Val Phe Pro Leu Ala Pro Cys Ser Arg Ser Thr
145                 150                 155                 160
Ser Glu Ser Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
            180                 185                 190
```

His Thr Phe Pro Ala Val Leu Gln Ser Ser Gly Leu Tyr Ser Leu Ser
            195                 200                 205

Ser Val Val Thr Val Pro Ser Ser Asn Phe Gly Thr Gln Thr Tyr Thr
        210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
            260                 265                 270

His His His His His His His
        275

<210> SEQ ID NO 20
<211> LENGTH: 279
<212> TYPE: PRT
<213> ORGANISM: homosapiens

<400> SEQUENCE: 20

Met Glu Phe Gly Leu Ser Trp Val Phe Leu Val Ala Leu Leu Arg Asp
1               5                   10                  15

Val Gln Cys Gln Val Leu Leu Val Gln Ser Gly Gly Val Val Glu
            20                  25                  30

Pro Gly Arg Ser Leu Arg Leu Ser Cys Val Gly Ser Gly Phe Met Phe
        35                  40                  45

Ser Asn Tyr Gly Val His Trp Val Arg Gln Ala Pro Gly Lys Gly Leu
    50                  55                  60

Glu Trp Val Ala Gly Ile Ser Ala Asp Ala Ile His Lys Val His Ala
65                  70                  75                  80

Gly Ser Leu Glu Gly Arg Phe Ala Ile Ser Arg Asp Asn Val Lys Ser
                85                  90                  95

Thr Val Tyr Leu Gln Met Asn Ser Leu Arg Pro Glu Asp Thr Ala Val
            100                 105                 110

Tyr Tyr Cys Val Arg Ser Lys Gln Ser Ser Asn Phe Asp Trp Leu Phe
        115                 120                 125

Ser Asp Tyr Trp Gly Gln Gly Asn Leu Val Ala Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Gln Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
            260                 265                 270

His His His His His His His
        275

<210> SEQ ID NO 21
<211> LENGTH: 269
<212> TYPE: PRT
<213> ORGANISM: homosapiens

<400> SEQUENCE: 21

Met Val Phe Gly Leu Ser Trp Val Phe Leu Val Ala Ile Leu Lys Gly
1               5                   10                  15

Val Gln Cys Glu Val Gln Leu Val Glu Ser Gly Gly Ala Ser Val Gln
                20                  25                  30

Pro Gly Gly Ser Leu Arg Leu Ser Cys Ala Ala Ser Gly Phe Thr Phe
            35                  40                  45

Ser Asn Tyr Tyr Met His Trp Val Arg Gln Ala Pro Gly Lys Gly Leu
        50                  55                  60

Glu Trp Val Ser Tyr Ser Ser Gly Asp Gly Arg Ile Thr Thr Tyr Ala
65                  70                  75                  80

Gly Ser Val Lys Gly Arg Phe Ile Ile Ser Arg Asp Asn Ala Lys Ser
                85                  90                  95

Thr Leu Tyr Leu Gln Met Asn Ser Leu Arg Ala Glu Asp Thr Ala Val
            100                 105                 110

Tyr Tyr Cys Ala Lys Glu Ser Ala Ser Trp Gly Gln Gly Thr Leu Val
        115                 120                 125

Thr Val Ser Ser Ala Ser Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Asn Phe
        195                 200                 205

Gly Thr Gln Thr Tyr Thr Cys Asn Val Asp His Lys Pro Ser Asn Thr
    210                 215                 220

Lys Val Asp Lys Thr Val Glu Arg Lys Cys Cys Val Glu Cys Pro Pro
225                 230                 235                 240

Cys Pro Ala Pro Pro Val Ala Gly Pro Ser Val Phe Leu Phe Pro Pro
                245                 250                 255

Lys Pro Lys Asp Thr His His His His His His
            260                 265

<210> SEQ ID NO 22
<211> LENGTH: 277
<212> TYPE: PRT
<213> ORGANISM: homosapiens

<400> SEQUENCE: 22

Met Glu Phe Gly Leu Ala Trp Val Phe Leu Val Ala Leu Leu Arg Gly
1               5                   10                  15

Val Gln Cys Gln Val Gln Leu Val Glu Ser Gly Gly Asn Val Val Gln
                20                  25                  30

Pro Gly Arg Ser Leu Arg Leu Ser Cys Val Gly Ser Gly Phe Thr Phe
            35                  40                  45

Gly Asn Tyr Ala Ile His Trp Val Arg Gln Ala Pro Gly Lys Gly Pro
        50                  55                  60

-continued

Glu Trp Val Ala Gly Ile Ser Ser Ala Gly His Leu Lys Tyr Tyr Thr
65                  70                  75                  80

Asp Ser Val Glu Gly Arg Phe Ser Ser Arg Asp Asn Ser Gln Asn
            85                  90                  95

Thr Val Tyr Leu Gln Leu Asn Ser Leu Arg Leu Glu Asp Thr Ala Met
            100                 105                 110

Tyr Tyr Cys Val Lys Ser Gln Gly Pro Thr Ala Phe Asp Trp Leu Phe
            115                 120                 125

Ser Gln Tyr Trp Gly Gln Gly Thr Pro Val Thr Val Ser Leu Ala Ser
            130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
            165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
            195                 200                 205

Ser Val Val Thr Val Pro Ser Ser Asn Phe Gly Thr Gln Thr Tyr Thr
            210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
            245                 250                 255

Ala Gly Pro Ser Val Phe Leu Phe Pro Pro Lys Pro Lys Asp Thr His
            260                 265                 270

His His His His His
            275

<210> SEQ ID NO 23
<211> LENGTH: 284
<212> TYPE: PRT
<213> ORGANISM: homosapiens

<400> SEQUENCE: 23

Met Glu Phe Gly Leu Ser Trp Val Phe Leu Val Ala Ile Leu Glu Gly
1               5                   10                  15

Val Gln Cys Glu Val Gln Leu Val Glu Ser Gly Gly Ala Leu Val Gln
            20                  25                  30

Pro Gly Gly Ser Leu Arg Leu Ser Cys Ala Ala Ser Gly Phe Thr Phe
            35                  40                  45

Ser Ser Tyr Glu Met Asn Trp Val Arg Gln Ala Pro Gly Lys Gly Leu
50                  55                  60

Glu Trp Val Ser Tyr Ile Gly Ser Ser Gly Ser Ala Ile Ser Tyr Ser
65                  70                  75                  80

Asp Ser Val Lys Gly Arg Phe Thr Ile Ser Arg Asp Asn Ala Lys Asn
            85                  90                  95

Ser Leu Tyr Leu Gln Met Asn Ser Leu Arg Ala Glu Asp Thr Ala Val
            100                 105                 110

Tyr Tyr Cys Ala Arg Asp Arg Ser Leu Val Arg Gly Ile Phe Ser Tyr
            115                 120                 125

Phe Tyr Gly Met Asp Val Trp Gly Gln Gly Thr Thr Val Thr Val Ser
            130                 135                 140

Ser Ala Ser Thr Lys Gly Pro Ser Val Phe Pro Leu Ala Pro Ser Ser

```
                145                 150                 155                 160
        Lys Ser Thr Ser Gly Gly Thr Ala Ala Leu Gly Cys Leu Val Lys Asp
                        165                 170                 175

Tyr Phe Pro Glu Pro Val Thr Val Ser Trp Asn Ser Gly Ala Leu Thr
                        180                 185                 190

Ser Gly Val His Thr Phe Pro Ala Val Leu Gln Ser Ser Gly Leu Tyr
                        195                 200                 205

Ser Leu Ser Ser Val Val Thr Val Pro Ser Ser Ser Leu Gly Thr Gln
                210                 215                 220

Thr Tyr Ile Cys Asn Val Asn His Lys Pro Ser Asn Thr Lys Val Asp
        225                 230                 235                 240

Lys Lys Val Glu Pro Lys Ser Cys Asp Lys Thr His Thr Cys Pro Pro
                        245                 250                 255

Cys Pro Ala Pro Glu Leu Leu Gly Gly Pro Ser Val Phe Leu Phe Pro
                        260                 265                 270

Pro Lys Pro Lys Asp Thr His His His His His His
                        275                 280

<210> SEQ ID NO 24
<211> LENGTH: 272
<212> TYPE: PRT
<213> ORGANISM: homosapiens

<400> SEQUENCE: 24

Met Glu Phe Gly Leu Ser Trp Val Phe Leu Val Ala Leu Leu Arg Gly
        1               5                   10                  15

Val Gln Cys Gln Val Arg Leu Val Glu Ser Gly Gly Gly Val Val Gln
                        20                  25                  30

Pro Gly Arg Ser Leu Arg Leu Ser Cys Ala Val Ser Gly Phe Thr Phe
                    35                  40                  45

Lys Asn Tyr Ala Met Leu Trp Val Arg Gln Ala Pro Gly Lys Gly Pro
                50                  55                  60

Glu Trp Leu Ser Leu Met Thr Ala Asp Gly Asn Tyr Arg Ser Tyr Ala
        65                  70                  75                  80

Asp Ser Val Lys Gly Arg Phe Thr Ile Ser Arg Asp Asp Ser Asn Asn
                        85                  90                  95

Ile Leu Ser Leu Gln Met Asp Ser Leu Arg Pro Glu Asp Thr Ala Val
                    100                 105                 110

Tyr Tyr Cys Val Arg Glu Arg Asn Gly Tyr Tyr Pro Ala Asn Trp Gly
                    115                 120                 125

Gln Gly Thr Leu Val Thr Val Ser Ser Ala Ser Thr Lys Gly Pro Ser
                130                 135                 140

Val Phe Pro Leu Ala Pro Cys Ser Arg Ser Thr Ser Glu Ser Thr Ala
        145                 150                 155                 160

Ala Leu Gly Cys Leu Val Lys Asp Tyr Phe Pro Glu Pro Val Thr Val
                        165                 170                 175

Ser Trp Asn Ser Gly Ala Leu Thr Ser Gly Val His Thr Phe Pro Ala
                        180                 185                 190

Val Leu Gln Ser Ser Gly Leu Tyr Ser Leu Ser Ser Val Val Thr Val
                        195                 200                 205

Pro Ser Ser Asn Phe Gly Thr Gln Thr Tyr Thr Cys Asn Val Asp His
                    210                 215                 220

Lys Pro Ser Asn Thr Lys Val Asp Lys Thr Val Glu Arg Lys Cys Cys
        225                 230                 235                 240
```

Val Glu Cys Pro Pro Cys Pro Ala Pro Pro Val Ala Gly Pro Ser Val
            245                 250                 255

Phe Leu Phe Pro Pro Lys Pro Lys Asp Thr His His His His His His
        260                 265                 270

<210> SEQ ID NO 25
<211> LENGTH: 279
<212> TYPE: PRT
<213> ORGANISM: homosapiens

<400> SEQUENCE: 25

Met Glu Phe Gly Leu Ser Trp Ile Phe Leu Val Ala Ile Leu Lys Gly
1               5                   10                  15

Val Leu Cys Glu Val Gln Leu Val Glu Ser Gly Gly Ala Leu Val Gln
            20                  25                  30

Pro Gly Gly Ser Leu Arg Leu Ser Cys Ala Ala Ser Gly Phe Thr Phe
        35                  40                  45

Ser Asn Tyr Ala Met Thr Trp Val Arg Gln Thr Pro Gly Gln Ser Leu
    50                  55                  60

Glu Trp Val Ser Thr Ile Thr Asp Ser Gly Ser His Thr Tyr Tyr Pro
65                  70                  75                  80

Asp Ser Val Arg Gly Arg Phe Thr Ile Ser Arg Asp Asn Ser Lys Asn
                85                  90                  95

Ile Leu Tyr Leu Gln Ile Asn Asn Leu Arg Ala Glu Asp Thr Ala Val
            100                 105                 110

Tyr His Cys Ala Lys Arg Glu Arg Val Ala Val Leu Ala Tyr Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr His His His His His His
        275

<210> SEQ ID NO 26
<211> LENGTH: 277
<212> TYPE: PRT
<213> ORGANISM: homosapiens

<400> SEQUENCE: 26

Met Asp Phe Gly Leu Ser Trp Val Phe Leu Val Val Leu Leu Arg Gly
1               5                   10                  15

Val Gln Cys Gln Val Gln Leu Leu Glu Ser Gly Gly Gly Val Val Gln
            20                  25                  30

Pro Gly Thr Ser Leu Arg Leu Ser Cys Val Gly Ser Gly Tyr Ala Phe
        35                  40                  45

His Ser Tyr Arg Met His Trp Val Arg Gln Pro Gly Lys Gly Leu
    50                  55                  60

Glu Trp Met Ala Ser Ile Thr Tyr Asp Gly Ser Arg Thr Tyr Tyr Ala
65                  70                  75                  80

Asp Ser Glu Arg Gly Arg Leu Thr Ile Ser Arg Asp Asn Ser Lys Asn
                85                  90                  95

Thr Leu Phe Leu Gln Met Asn Thr Leu Arg Pro His Asp Thr Ala Val
            100                 105                 110

Tyr Tyr Cys Ala Arg Glu Gly Glu Gly Asp Val Arg Asn Trp Tyr Ser
        115                 120                 125

Phe Ala Arg Trp Gly Gln Gly Thr Leu Val Ile Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
            260                 265                 270

His His His His His
        275

<210> SEQ ID NO 27
<211> LENGTH: 283
<212> TYPE: PRT
<213> ORGANISM: homosapiens

<400> SEQUENCE: 27

Met Glu Phe Gly Leu Ser Trp Leu Phe Leu Val Ala Ile Leu Lys Gly
1               5                   10                  15

Val Gln Cys Glu Val Gln Val Ser Glu Ser Gly Gly Gly Leu Val Gln
            20                  25                  30

Pro Gly Gly Ser Leu Arg Ile Ser Cys Ala Ala Ser Gly Phe Thr Phe
        35                  40                  45

Arg Asn Tyr Ala Met Ser Trp Val Arg Gln Ala Pro Gly Lys Gly Leu
    50                  55                  60

Glu Trp Val Ser Ala Ile Thr Gly Ser Gly Ala Thr Thr Tyr Phe Ala
65                  70                  75                  80

Asp Ser Val Lys Gly Arg Phe Ser Ile Ser Arg Asp Asn Ser Lys Asn
                85                  90                  95

Ala Leu Tyr Leu Gln Leu Ser Ser Leu Arg Ala Glu Asp Thr Ala Ile
            100                 105                 110

Tyr Tyr Cys Ala Arg Leu Pro Arg Glu Gly Arg Ala Gly Tyr Ser Ser
            115                 120                 125

Gly Trp Gly Asp Asn Trp Phe Asp Pro Trp Gly Gln Gly Thr Leu Val
        130                 135                 140

Thr Val Ser Ser Ala Ser Thr Lys Gly Pro Ser Val Phe Pro Leu Ala
145                 150                 155                 160

Pro Cys Ser Arg Ser Thr Ser Glu Ser Thr Ala Ala Leu Gly Cys Leu
                165                 170                 175

Val Lys Asp Tyr Phe Pro Glu Pro Val Thr Val Ser Trp Asn Ser Gly
                180                 185                 190

Ala Leu Thr Ser Gly Val His Thr Phe Pro Ala Val Leu Gln Ser Ser
            195                 200                 205

Gly Leu Tyr Ser Leu Ser Ser Val Val Thr Val Pro Ser Ser Asn Phe
        210                 215                 220

Gly Thr Gln Thr Tyr Thr Cys Asn Val Asp His Lys Pro Ser Asn Thr
225                 230                 235                 240

Lys Val Asp Lys Thr Val Glu Arg Lys Cys Val Glu Cys Pro Pro
                245                 250                 255

Cys Pro Ala Pro Pro Val Ala Gly Pro Ser Val Phe Leu Phe Pro Pro
            260                 265                 270

Lys Pro Lys Asp Thr His His His His His His
                275                 280

<210> SEQ ID NO 28
<211> LENGTH: 278
<212> TYPE: PRT
<213> ORGANISM: homosapiens

<400> SEQUENCE: 28

Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Ser Val Val Gln
                20                  25                  30

Pro Gly Arg Ser Leu Arg Leu Ser Cys Ala Ala Ser Gly Phe Ala Phe
            35                  40                  45

His Ser Phe Ala Met His Trp Val Arg Gln Ala Pro Gly Lys Gly Leu
        50                  55                  60

Glu Trp Val Ala Leu Ile Ser Tyr Asp Gly Ser Asn Lys Tyr Tyr Ala
65                  70                  75                  80

Asp Ser Val Arg Gly Arg Phe Thr Leu Ser Arg Asp Asn Ser Asn Asn
                85                  90                  95

Ile Val Tyr Leu Gln Met Asp Ser Leu Thr Phe Asp Asp Thr Ala Val
                100                 105                 110

Tyr Tyr Cys Ala Arg Glu Gly Ser Pro His His Gly Thr Ser Trp Tyr
            115                 120                 125

Gly Phe Asp Glu Trp Gly Gln Gly Thr Leu Met Thr Val Ser Ser Ala
        130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu

```
            195                 200                 205
Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

His His His His His His
            275
```

<210> SEQ ID NO 29
<211> LENGTH: 283
<212> TYPE: PRT
<213> ORGANISM: homosapiens

<400> SEQUENCE: 29

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Arg Leu Val Gln
            20                  25                  30

Pro Gly Gly Ser Leu Arg Leu Ser Cys Ala Ala Ser Gly Phe Thr Phe
        35                  40                  45

Arg Ser Ser Trp Met Thr Trp Val Arg Gln Ala Pro Gly Lys Gly Leu
50                  55                  60

Glu Trp Val Gly Phe Val Lys Ser Arg Thr Tyr Gly Gly Thr Arg Asp
65                  70                  75                  80

Tyr Ala Ala Ser Val Lys Gly Arg Phe Thr Ile Ser Arg Asp Asp Ser
                85                  90                  95

Asn Ser Val Val Tyr Leu Gln Met Asn Ser Leu Lys Thr Glu Asp Thr
            100                 105                 110

Ala Val Tyr Tyr Cys Val Arg Thr Ala Arg Tyr Cys Ser Gly Ile Ser
        115                 120                 125

Cys Asn Met Gly Thr Glu Phe Asp Tyr Trp Gly Gln Gly Thr Leu Val
    130                 135                 140

Thr Val Ser Ser Ala Ser Thr Lys Gly Pro Ser Val Phe Pro Leu Ala
145                 150                 155                 160

Pro Cys Ser Arg Ser Thr Ser Glu Ser Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Glu Ser Ser
        195                 200                 205

Gly Leu Tyr Ser Leu Ser Ser Val Val Thr Val Pro Ser Ser Asn Phe
    210                 215                 220

Gly Thr Gln Thr Tyr Thr Cys Asn Val Asp His Lys Pro Ser Asn Thr
225                 230                 235                 240

Lys Val Asp Lys Thr Val Glu Arg Lys Cys Cys Val Glu Cys Pro Pro
                245                 250                 255

Cys Pro Ala Pro Pro Val Ala Gly Pro Ser Val Phe Leu Phe Pro Pro
            260                 265                 270

Lys Pro Lys Asp Thr His His His His His
            275                 280
```

<210> SEQ ID NO 30
<211> LENGTH: 273
<212> TYPE: PRT
<213> ORGANISM: homosapiens

<400> SEQUENCE: 30

Met Glu Phe Gly Leu Ser Trp Val Phe Leu Ala Ala Leu Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Val Ser Gly Phe Ala Leu
        35                  40                  45

Arg Asp Ser Pro Ile His Trp Val Arg Gln Ala Ser Gly Lys Gly Leu
    50                  55                  60

Glu Trp Val Ala His Thr Pro Arg Ser Gly Gly Tyr Phe Ala Ala Thr
65                  70                  75                  80

Tyr Val Ala Ser Val Arg Gly Arg Phe Thr Ile Ser Arg Asp Glu Ser
                85                  90                  95

Arg Asn Ile Val Tyr Leu Gln Met Asn Arg Leu Asn Gly Glu Asp Thr
            100                 105                 110

Ala Val Tyr Tyr Cys Thr Arg Gln Thr Asp Ser Val His Asp Tyr Trp
        115                 120                 125

Gly Gln Gly Ile Val Val Thr Val Ser Ser Ala Ser Thr Lys Gly Pro
    130                 135                 140

Ser Val Phe Pro Leu Ala Pro Cys Ser Arg Ser Thr Ser Glu Asn Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr His His His His His
            260                 265                 270

His

<210> SEQ ID NO 31
<211> LENGTH: 265
<212> TYPE: PRT
<213> ORGANISM: homosapiens

<400> SEQUENCE: 31

Met Asp Phe Gly Leu Ser Trp Ile Phe Leu Val Ala Leu Leu Arg Gly
1               5                   10                  15

Val Gln Cys Gln Val His Leu Val Glu Ser Gly Gly Gly Leu Val Gln
            20                  25                  30

Pro Gly Arg Ser Leu Arg Leu Ser Cys Ala Val Ser Gly Phe Thr Phe
        35                  40                  45

Ala Ser Tyr Ala Met His Trp Val Arg Gln Ala Pro Gly Lys Gly Leu

```
              50                  55                  60
Glu Trp Val Ala Gly Ile Ser Lys Asp Gly Ser Asn Lys Arg His Ala
 65                  70                  75                  80

Asp Ser Leu Glu Gly Arg Phe Thr Ile Ser Arg Asp Asn Ser Lys Asn
                 85                  90                  95

Thr Leu Tyr Leu Gln Val Ser Gly Leu Arg Ala Glu Asp Thr Ala Val
            100                 105                 110

Tyr Tyr Cys Ala Arg Ser Gln Asp Pro Thr Asp Phe Trp Leu Leu
            115                 120                 125

Ser Glu His Trp Gly Gln Gly Thr Leu Val Thr Val Ser Ser Ala Ser
            130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
            195                 200                 205

Ser Val Val Thr Val Pro Ser Ser Asn Phe Gly Thr Gln Thr Tyr Thr
            210                 215                 220

Cys Asn Val Asp His Lys Pro Ser Asn Thr Lys Val Asp Lys Thr Val
225                 230                 235                 240

Ala Pro Pro Val Ala Gly Pro Ser Val Phe Leu Phe Pro Pro Lys Pro
                245                 250                 255

Lys Asp Thr His His His His His His
            260                 265

<210> SEQ ID NO 32
<211> LENGTH: 277
<212> TYPE: PRT
<213> ORGANISM: homosapiens

<400> SEQUENCE: 32

Met Gln Phe Gly Leu Ser Trp Val Phe Leu Val Ala Leu Leu Arg Gly
 1               5                  10                  15

Val Gln Cys Gln Val Gln Leu Val Glu Ser Gly Gly Gly Val Val Gln
                20                  25                  30

Pro Gly Arg Ser Leu Arg Leu Ser Cys Val Gly Ser Gly Phe Thr Phe
            35                  40                  45

Ser Thr Tyr Ala Ile His Trp Val Arg Gln Ala Pro Gly Lys Gly Leu
 50                  55                  60

Glu Trp Val Ala Gly Ile Ser Asp Gly Asp Phe Gln Ile Tyr Ala
 65                  70                  75                  80

Asp Ser Val Gln Gly Arg Phe Thr Ser Ser Arg Asp Asn Ser Lys Asn
                 85                  90                  95

Thr Val His Leu Gln Val Asn Ser Leu Arg Leu Gly Asp Thr Ala Met
            100                 105                 110

Tyr Tyr Cys Val Arg Pro Gln Gln Pro Ser Ser Phe Asp Phe Leu Phe
            115                 120                 125

Ser Asp Tyr Trp Gly Leu Gly Thr Leu Ile Thr Val Ser Ser Ala Ser
            130                 135                 140

Thr Lys Gly Pro Ser Val Phe Pro Leu Ala Pro Cys Ser Arg Ser Thr
145                 150                 155                 160
```

Ser Glu Ser Thr Ala Ala Leu Gly Cys Leu Val Lys Asp Tyr Phe Pro
            165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
            195                 200                 205

Ser Val Val Thr Val Pro Ser Ser Asn Phe Gly Thr Gln Thr Tyr Thr
210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
            245                 250                 255

Ala Gly Pro Ser Val Phe Leu Phe Pro Pro Lys Pro Lys Asp Thr His
            260                 265                 270

His His His His His
        275

<210> SEQ ID NO 33
<211> LENGTH: 273
<212> TYPE: PRT
<213> ORGANISM: homosapiens

<400> SEQUENCE: 33

Met Glu Phe Gly Leu Ser Trp Val Phe Leu Val Ala Val Leu Lys Gly
1               5                   10                  15

Val Gln Ser Asp Val Glu Leu Val Glu Ser Gly Gly Gly Leu Val Arg
            20                  25                  30

Pro Gly Gly Ser Leu Arg Leu Ser Cys Lys Ala Ser Gly Phe Thr Ile
            35                  40                  45

Arg Ser Asn Ser Met Thr Trp Val Arg Gln Ser Val Lys Lys Gly Leu
        50                  55                  60

Glu Trp Val Ser Val Phe Tyr Ser Gly Ala Lys Thr Val Tyr Ser Asp
65                  70                  75                  80

Ser Val Arg Gly Arg Phe Thr Ile Ser Arg Asp Asn Ser Lys Asn Thr
                85                  90                  95

Leu Tyr Pro Gln Met Asn Ser Leu Thr Asn Glu Asp Thr Ala Phe Tyr
            100                 105                 110

Tyr Cys Ala Arg Ala Leu His Gly Asn Ser Trp Tyr Ala Ala Tyr Trp
        115                 120                 125

Gly Gln Gly Thr Leu Val Thr Val Ser Ser Ala Ser Thr Lys Gly Pro
130                 135                 140

Ser Leu Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

```
Val Phe Leu Phe Pro Pro Lys Pro Lys Asp Thr His His His His
            260                 265                 270

His

<210> SEQ ID NO 34
<211> LENGTH: 273
<212> TYPE: PRT
<213> ORGANISM: homosapiens

<400> SEQUENCE: 34

Met Glu Phe Gly Leu Ser Trp Val Phe Leu Val Val Ile Leu Gln Gly
1               5                   10                  15

Ala His Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Ser
        35                  40                  45

Ser Asp His Tyr Met Asp Trp Val Arg Gln Ala Pro Gly Lys Gly Leu
    50                  55                  60

Asp Trp Val Gly Arg Ser Lys Asn Lys Ala Asn Arg Tyr Thr Thr Glu
65                  70                  75                  80

Tyr Ala Ala Ser Val Lys Gly Arg Phe Thr Ile Ser Arg Asp Asp Ser
                85                  90                  95

Lys Asn Ser Met Tyr Leu Gln Met Asn Ser Leu Arg Thr Glu Asp Thr
            100                 105                 110

Ala Val Tyr Tyr Cys Thr Arg Trp Thr Ser Gly Cys Cys Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr His His His His
            260                 265                 270

His

<210> SEQ ID NO 35
<211> LENGTH: 277
<212> TYPE: PRT
<213> ORGANISM: homosapiens

<400> SEQUENCE: 35

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
```

```
            20                  25                  30
Pro Gly Arg Ser Leu Arg Leu Ser Cys Ala Val Ser Gly Phe Thr Phe
            35                  40                  45

Thr Asn Tyr Ala Ile His Trp Val Arg Gln Ala Pro Gly Lys Gly Leu
 50                  55                  60

Glu Trp Val Ala Gly Ile Ser Ser Asp Gly Ser Asn His Ile Tyr Ala
 65                  70                  75                  80

Asp Ser Val Glu Gly Arg Phe Thr Ile Ser Arg Asp Asn Ser Lys Asn
                 85                  90                  95

Thr Leu Phe Leu Gln Val Asn Gly Leu Arg Ala Glu Asp Thr Ala Val
            100                 105                 110

Tyr Phe Cys Val Arg Ser Arg Asp Pro Thr Asp Phe Asp Phe Leu Leu
        115                 120                 125

Cys Asp Tyr Trp Gly Gln Gly Thr Leu Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
            260                 265                 270

His His His His His
            275

<210> SEQ ID NO 36
<211> LENGTH: 273
<212> TYPE: PRT
<213> ORGANISM: homosapiens

<400> SEQUENCE: 36

Met Glu Phe Gly Leu Ser Trp Leu Phe Leu Val Ala Ile Leu Lys Ala
  1               5                  10                  15

Val Gln Cys Glu Val Gln Leu Leu Glu Ser Gly Gly Gly Leu Val Gln
             20                  25                  30

Pro Gly Gly Ser Leu Arg Leu Ser Cys Ala Ala Ser Gly Phe Thr Phe
            35                  40                  45

Ser Ser Tyr Ala Met Arg Trp Val Arg Gln Ala Pro Gly Lys Gly Leu
 50                  55                  60

Glu Trp Val Ser Leu Ile Ser Asp Arg Gly Gly Ser Thr Tyr Tyr Val
 65                  70                  75                  80

Asp Ser Val Lys Gly Arg Phe Thr Ile Tyr Arg Asp Asn Ser Glu Asn
                 85                  90                  95

Thr Leu Tyr Leu Gln Met Asn Ser Leu Arg Ala Glu Asp Thr Ala Val
            100                 105                 110
```

```
Tyr Tyr Cys Ala Lys Asp Pro Asp Asn Asn Thr Pro Val Asp Tyr Trp
            115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
            195                 200                 205

Val Pro Ser Ser Asn Phe Gly Thr Gln Thr Tyr Thr Cys Asn Val Asp
        210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Asn Pro Lys Asp Thr His His His His
                260                 265                 270

His
```

<210> SEQ ID NO 37
<211> LENGTH: 276
<212> TYPE: PRT
<213> ORGANISM: homosapiens

<400> SEQUENCE: 37

```
Met Asp Phe Gly Leu Ser Trp Leu Phe Leu Val Thr Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Phe Ala Met Thr Trp Val Arg Gln Ala Pro Gly Lys Gly Leu
    50                  55                  60

Glu Trp Val Ser Ala Ile Tyr Gly Gly Gly Asp Arg Thr Phe Tyr Ala
65                  70                  75                  80

Gly Ser Val Lys Gly Arg Phe Thr Val Ser Arg Asp Asn Ser Lys Asn
                85                  90                  95

Thr Leu Tyr Leu Gln Met Asn Ser Leu Ser Ala Glu Asp Thr Ala Val
            100                 105                 110

Tyr Phe Cys Ala Lys Asp Pro Ser Tyr Pro Thr Val Thr Thr Ile Ile
        115                 120                 125

Asp Pro Trp Gly Gln Gly Thr Leu Val Ser Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
            195                 200                 205
```

```
Val Val Thr Val Pro Ser Ser Asn Phe Gly Thr Gln Thr Tyr Thr Cys
            210             215                 220
Asn Val Asp His Lys Pro Ser Asn Thr Lys Val Asp Lys Thr Val Glu
225             230                 235                 240
Arg Lys Cys Cys Val Glu Cys Pro Pro Cys Pro Ala Pro Pro Val Ala
                245                 250                 255
Gly Pro Ser Val Phe Leu Phe Pro Pro Lys Pro Lys Asp Thr His His
            260                 265                 270
His His His His
        275

<210> SEQ ID NO 38
<211> LENGTH: 276
<212> TYPE: PRT
<213> ORGANISM: homosapiens

<400> SEQUENCE: 38

Met Glu Phe Gly Leu Ser Trp Val Phe Leu Val Ala Ile Leu Lys Gly
1               5                   10                  15
Ile Gln Cys Glu Met Gln Leu Val Glu Ser Gly Gly Ala Val Val Gln
            20                  25                  30
Pro Gly Gly Ser Leu Arg Leu Ser Cys Ala Ala Ser Gly Phe Thr Phe
        35                  40                  45
Gly His Tyr Ser Met Gln Trp Val Arg Gln Leu Pro Gly Lys Thr Leu
    50                  55                  60
Glu Trp Val Ser Leu Ile Asn Arg Asp Gly Ser Val Thr Tyr Tyr Ala
65                  70                  75                  80
Asp Ser Val Lys Gly Arg Phe Thr Ile Ser Arg Asp Asn Ser Arg Asn
                85                  90                  95
Ser Leu Tyr Leu Gln Met Asn Ser Leu Arg Ile Glu Asp Thr Ala Leu
            100                 105                 110
Tyr Tyr Cys Ala Lys Glu Lys Leu Asp Gly Thr Trp Thr Ala Leu Asp
        115                 120                 125
Tyr Trp Gly Gln Gly Ser Leu Val Thr Val Ser Ser Ala Ser Thr Lys
    130                 135                 140
Gly Pro Ser Val Phe Pro Leu Ala Pro Cys Ser Arg Ser Thr Ser Glu
145                 150                 155                 160
Ser Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
        195                 200                 205
Val Thr Val Pro Ser Ser Leu Gly Thr Lys Thr Tyr Thr Cys Asn
    210                 215                 220
Val Asp His Lys Pro Ser Asn Thr Lys Val Asp Lys Arg Val Glu Ser
225                 230                 235                 240
Lys Tyr Gly Pro Pro Cys Pro Ser Cys Pro Ala Pro Glu Phe Leu Gly
                245                 250                 255
Gly Pro Ser Val Phe Leu Phe Pro Pro Lys Pro Lys Asp Thr His His
            260                 265                 270
His His His His
        275

<210> SEQ ID NO 39
```

<211> LENGTH: 287
<212> TYPE: PRT
<213> ORGANISM: homosapiens

<400> SEQUENCE: 39

Met Glu Phe Gly Leu Ser Trp Val Phe Leu Val Ala Ile Leu Gln Gly
1               5                   10                  15

Val Gln Cys Glu Val His Leu Val Glu Ser Gly Gly Asp Leu Ile Glu
            20                  25                  30

Pro Gly Gly Ser Leu Arg Leu Ser Cys Ala Ala Ser Gly Phe Ile Val
        35                  40                  45

Ser Ser Asn Tyr Met Asp Trp Val Arg Gln Ala Pro Gly Lys Gly Leu
    50                  55                  60

Glu Trp Val Gly Arg Ile Arg Trp Lys Ser Arg Gln Pro Thr Thr
65                  70                  75                  80

Tyr Ala Ala Ser Val Lys Gly Arg Phe Ile Met Ser Arg Asp Asp Ser
                85                  90                  95

Gln Gly Ser Val Tyr Leu Gln Met Asn Ser Leu Lys Ile Glu Asp Ala
            100                 105                 110

Ala Val Tyr Tyr Cys Val Arg Val Asn Phe Phe Asp Thr Ser Gly Tyr
        115                 120                 125

Ser Leu Asp Ala Phe Asp Ile Trp Gly Arg Gly Thr Lys Val Thr Val
    130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
    210                 215                 220

Gln Thr Tyr Thr Cys Asn Val Asp His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr His His His His His His
        275                 280                 285

<210> SEQ ID NO 40
<211> LENGTH: 282
<212> TYPE: PRT
<213> ORGANISM: homosapiens

<400> SEQUENCE: 40

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Glu Ala Ser Gly Phe Thr Phe
        35                  40                  45

Gly Ser Tyr Trp Met His Trp Val Arg Gln Gly Pro Gly Lys Gly Leu
    50                  55                  60

```
Glu Trp Val Ser Arg Thr Asn Ile Asp Gly Leu Ser Thr His Tyr Ala
65                  70                  75                  80

Asp Ser Val Arg Gly Arg Phe Ile Ile Ser Arg Asp Asn Ala Lys Asn
                85                  90                  95

Thr Leu Tyr Leu Glu Met Asn Ser Leu Arg Ala Glu Asp Thr Gly Leu
            100                 105                 110

Tyr Tyr Cys Ala Arg Asp Met Trp Ser Tyr Asn Cys Arg Asp Thr Ser
            115                 120                 125

Cys His Ala Phe Asp Leu Trp Gly Arg Gly Thr Leu Val Thr Val Ser
130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Asn Phe Gly Thr Gln
210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr His His His His His His His His
            275                 280

<210> SEQ ID NO 41
<211> LENGTH: 278
<212> TYPE: PRT
<213> ORGANISM: homosapiens

<400> SEQUENCE: 41

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Ser Thr Phe
            35                  40                  45

Ser Ser Tyr Trp Met His Trp Val Arg Gln Ala Pro Gly Lys Gly Leu
50                  55                  60

Leu Trp Val Ser Arg Ile Asn Ser Asp Gly Ser Ser Thr Ser Tyr Val
65                  70                  75                  80

Asp Ser Val Lys Gly Arg Phe Thr Ile Ser Arg Asp Asn Ala Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Ser Ala Tyr Tyr Ser Ser Arg Ser Tyr Ser
            115                 120                 125

Trp Gly Arg Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
```

```
            145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
                180                 185                 190
Pro Ala Val Leu Gln Ser Ser Gly Leu Tyr Ser Leu Ser Ser Val Val
                195                 200                 205
Thr Val Pro Ser Ser Ser Leu Gly Thr Gln Thr Tyr Ile Cys Asn Val
        210                 215                 220
Asn His Lys Pro Ser Asn Thr Lys Val Asp Lys Lys Val Glu Pro Lys
225                 230                 235                 240
Ser Cys Asp Lys Thr His Thr Cys Pro Pro Cys Pro Ala Pro Glu Leu
                245                 250                 255
Leu Gly Gly Pro Ser Val Phe Leu Phe Pro Pro Lys Pro Lys Asp Thr
                260                 265                 270
His His His His His His
            275

<210> SEQ ID NO 42
<211> LENGTH: 273
<212> TYPE: PRT
<213> ORGANISM: homosapiens

<400> SEQUENCE: 42

Met Glu Phe Gly Leu Ser Trp Leu Phe Leu Val Ala Leu Ile Lys Gly
1               5                   10                  15
Val Gln Cys Glu Val Gln Val Ala Glu Ser Gly Gly Gly Leu Val Lys
                20                  25                  30
Pro Gly Gly Ser Leu Arg Leu Ser Cys Ala Ala Ser Gly Phe Thr Phe
            35                  40                  45
Ser Asn Phe Ala Met Thr Trp Val Arg Gln Thr Pro Glu Lys Gly Leu
        50                  55                  60
Gln Trp Val Ser Ala Leu Thr Gly Arg Gly Asp Lys Thr Tyr Tyr Ala
65                  70                  75                  80
Asp Ser Val Lys Gly Arg Phe Thr Val Ser Arg Asp Asn Ser Lys Asn
                85                  90                  95
Thr Leu Tyr Leu Gln Met Asn Ser Leu Gly Ala Glu Asp Thr Ala Val
                100                 105                 110
Tyr Tyr Cys Ala Lys Trp Lys Ser Gly Tyr Ala Pro Leu Asp Ser Trp
            115                 120                 125
Gly Gln Gly Thr Leu Val Ile Val Ser Ser Ala Ser Thr Lys Gly Pro
        130                 135                 140
Ser Val Phe Pro Leu Ala Pro Cys Ser Arg Ser Thr Ser Glu Ser Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
                180                 185                 190
Ala Val Leu Gln Ser Ser Gly Leu Tyr Ser Leu Ser Ser Val Val Thr
            195                 200                 205
Val Pro Ser Ser Asn Phe Gly Thr Gln Thr Tyr Thr Cys Asn Val Asp
        210                 215                 220
His Lys Pro Ser Asn Thr Lys Val Asp Lys Thr Val Glu Arg Lys Cys
225                 230                 235                 240
```

```
Cys Val Glu Cys Pro Pro Cys Pro Ala Pro Pro Val Ala Gly Pro Ser
            245                 250                 255

Val Phe Leu Phe Pro Pro Lys Pro Lys Asp Thr Asp His His His His
        260                 265                 270

His
```

<210> SEQ ID NO 43
<211> LENGTH: 276
<212> TYPE: PRT
<213> ORGANISM: homosapiens

<400> SEQUENCE: 43

```
Met Glu Phe Gly Leu Ser Trp Val Phe Leu Ala Ala Ile Leu Lys Gly
1               5                   10                  15

Val Gln Cys Glu Ala Gln Leu Val Glu Ser Gly Gly Gly Val Val Arg
            20                  25                  30

Pro Gly Gly Ser Leu Arg Leu Ser Cys Ala Ala Ser Gly Phe Thr Phe
        35                  40                  45

Asp Asp Tyr Gly Met Ser Trp Val Arg Gln Ala Pro Gly Lys Gly Leu
    50                  55                  60

Glu Trp Val Ser Gly Ile Asn Trp Asn Gly Gly Arg Thr Thr Tyr Ala
65                  70                  75                  80

Asp Ser Val Lys Gly Arg Phe Thr Ile Ser Arg Asp Asn Ala Lys Asn
                85                  90                  95

Phe Leu Tyr Leu Glu Met Asn Ser Leu Arg Val Asp Asp Thr Ala Phe
            100                 105                 110

Tyr His Cys Ala Arg Val Arg Met Thr Asn Gly Asn Trp Phe Asp Pro
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Asn
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Asn His His His His
            260                 265                 270

His His His His
        275
```

<210> SEQ ID NO 44
<211> LENGTH: 264
<212> TYPE: PRT
<213> ORGANISM: homosapiens

<400> SEQUENCE: 44

Met Ser Trp Val Arg Gln Ala Pro Gly Lys Gly Leu Glu Trp Val Gly

```
1               5                   10                  15
Arg Ile Lys Ser Lys Thr Asp Gly Gly Thr Thr Asp Tyr Ala Ala Pro
                20                  25                  30

Val Lys Gly Arg Phe Thr Ile Ser Arg Asp Asp Ser Lys Asn Thr Leu
                35                  40                  45

Tyr Leu Gln Met Asn Ser Leu Lys Thr Glu Asp Thr Ala Val Tyr Tyr
                50                  55                  60

Cys Thr Thr Asp Arg Leu Arg Tyr Phe Asp Trp Ser Thr Tyr Tyr Phe
65                  70                  75                  80

Asp Tyr Trp Gly Gln Gly Thr Leu Val Thr Val Ser Ser Ala Ser Thr
                85                  90                  95

Lys Gly Pro Ser Val Phe Pro Leu Ala Pro Cys Ser Arg Ser Thr Ser
                100                 105                 110

Gly Gly Thr Ala Ala Leu Gly Cys Leu Val Lys Asp Tyr Phe Pro Glu
                115                 120                 125

Pro Val Thr Val Ser Trp Asn Ser Gly Ala Leu Thr Ser Gly Val His
                130                 135                 140

Thr Phe Pro Ala Val Leu Gln Ser Ser Gly Leu Tyr Ser Leu Ser Ser
145                 150                 155                 160

Val Val Thr Val Pro Ser Ser Ser Leu Gly Thr Gln Thr Tyr Thr Cys
                165                 170                 175

Asn Val Asn His Lys Pro Ser Asn Thr Lys Val Asp Lys Arg Val Glu
                180                 185                 190

Leu Lys Thr Pro Leu Gly Asp Thr Thr His Thr Cys Pro Arg Cys Pro
                195                 200                 205

Glu Pro Lys Ser Cys Asp Thr Pro Pro Pro Cys Pro Arg Cys Pro Glu
                210                 215                 220

Pro Lys Ser Cys Asp Thr Pro Pro Pro Cys Pro Arg Cys Pro Ala Pro
225                 230                 235                 240

Glu Leu Leu Gly Gly Pro Ser Val Phe Leu Phe Pro Pro Lys Pro Lys
                245                 250                 255

Asp Thr His His His His His His
                260

<210> SEQ ID NO 45
<211> LENGTH: 277
<212> TYPE: PRT
<213> ORGANISM: homosapiens

<400> SEQUENCE: 45

Met Glu Phe Gly Leu Ser Trp Ile Phe Leu Ala Ala Thr Leu Lys Gly
1               5                   10                  15

Val Gln Cys Glu Val Gln Leu Val Glu Ser Gly Gly Gly Leu Val Lys
                20                  25                  30

Pro Ala Gly Ser Leu Lys Leu Ser Cys Glu Ala Ser Gly Phe Ala Phe
                35                  40                  45

Ser Asn Val Trp Met Thr Trp Val Arg Gln Ala Pro Gly Lys Gly Leu
                50                  55                  60

Glu Trp Val Gly Arg Ile Thr Thr Lys Ala Asp Asn Trp Gly Thr Asp
65                  70                  75                  80

Tyr Ala Ala Pro Leu Arg Gly Arg Phe Thr Ile Ser Arg Asp Asp Ser
                85                  90                  95

Lys Asn Thr Leu Tyr Leu Gln Met Asn Ser Leu Lys Thr Glu Asp Thr
                100                 105                 110
```

Ala Ala Tyr Tyr Cys Ala Ile Leu Asn Arg Gly Arg Phe Glu Ser Trp
            115                 120                 125

Gly Gln Gly Thr Leu Val Thr Val Ser Ser Ala Ser Thr Lys Gly Pro
        130                 135                 140

Ser Val Phe Pro Leu Val Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Met Cys Asn Val Asn
        210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr His
            260                 265                 270

His His His His His
        275

<210> SEQ ID NO 46
<211> LENGTH: 269
<212> TYPE: PRT
<213> ORGANISM: homosapiens

<400> SEQUENCE: 46

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Asp Leu Ile Gln
            20                  25                  30

Pro Gly Gly Ser Leu Arg Leu Ser Cys Ile Ala Ser Gly Leu Ser Val
        35                  40                  45

Thr Asn Asn Tyr Met Ser Trp Val Arg Gln Ala Pro Gly Lys Gly Leu
    50                  55                  60

Asp Trp Val Ser Val Ile Phe Gly Gly Gly Asp Thr Tyr Tyr Ala Asp
65                  70                  75                  80

Ser Val Lys Gly Arg Phe Thr Ile Ser Lys Asp Asn Ser Lys Asn Thr
                85                  90                  95

Val Tyr Leu Gln Met Ser Ser Leu Arg Ala Glu Asp Thr Ala Val Tyr
            100                 105                 110

Tyr Cys Ala Lys Asp Asp Gly Ala Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

```
Gly Thr Gln Thr Tyr Thr Cys Asn Val Asp His Lys Pro Ser Asn Thr
        210                 215                 220

Lys Val Asp Lys Thr Val Glu Arg Lys Cys Cys Val Glu Cys Pro Pro
225                 230                 235                 240

Cys Pro Ala Pro Pro Val Ala Gly Pro Ser Val Phe Leu Phe Pro Pro
                245                 250                 255

Lys Pro Lys Asp Thr His His His His His His His
        260                 265
```

<210> SEQ ID NO 47
<211> LENGTH: 279
<212> TYPE: PRT
<213> ORGANISM: homosapiens
<220> FEATURE:
<221> NAME/KEY: MISC_FEATURE
<222> LOCATION: (233)..(233)
<223> OTHER INFORMATION: Xaa is Asn or Lys.

<400> SEQUENCE: 47

```
Met Glu Phe Gly Leu Ser Trp Val Phe Leu Val Ala Val Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Val Ser Gly Phe Thr Phe
        35                  40                  45

Ser Ser His Ser Met Asn Trp Val Arg Gln Ala Pro Gly Lys Gly Leu
    50                  55                  60

Glu Trp Ile Ser Tyr Ile Ser Thr Ser Arg Ser Ser Val Tyr Tyr Ala
65                  70                  75                  80

Asp Ser Val Lys Gly Arg Phe Phe Val Ser Arg Asp Asn Ala Glu Asn
                85                  90                  95

Leu Leu Tyr Leu Gln Met Asp Ser Leu Arg His Asp Asp Thr Ala Val
            100                 105                 110

Tyr Tyr Cys Ala Arg Gly Ser Arg Trp Asp Thr Leu Thr Gly Leu Asp
        115                 120                 125

His Trp Gly Gln Gly Thr Leu Val Thr Val Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Xaa Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr His His His His His His
        275
```

<210> SEQ ID NO 48
<211> LENGTH: 277
<212> TYPE: PRT
<213> ORGANISM: homosapiens

<400> SEQUENCE: 48

Met Glu Phe Gly Leu Ser Trp Val Phe Leu Val Ala Leu Leu Arg Asp
1               5                   10                  15

Val Gln Cys Gln Val Leu Leu Val Gln Ser Gly Gly Gly Val Val Glu
            20                  25                  30

Pro Gly Arg Ser Leu Arg Leu Ser Cys Val Gly Ser Gly Phe Met Phe
        35                  40                  45

Ser Asn Tyr Gly Val His Trp Val Arg Gln Ala Pro Gly Lys Gly Leu
    50                  55                  60

Glu Trp Val Ala Gly Ile Ser Ala Asp Ala Ile His Lys Val His Ala
65                  70                  75                  80

Gly Ser Leu Glu Gly Leu Phe Ala Ile Ser Arg Asp Asn Val Lys Ser
                85                  90                  95

Thr Val Tyr Leu Gln Met Asn Ser Leu Arg Pro Glu Asp Thr Ala Val
            100                 105                 110

Tyr Tyr Cys Val Arg Ser Lys Gln Ser Ser Asn Phe Asp Leu Leu Phe
        115                 120                 125

Ser Asp Tyr Trp Gly Gln Gly Asn Leu Val Ala Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Asn His
            260                 265                 270

His His His His
        275

<210> SEQ ID NO 49
<211> LENGTH: 279
<212> TYPE: PRT
<213> ORGANISM: homosapiens

<400> SEQUENCE: 49

Met Asp Phe Gly Leu Ser Trp Val Phe Leu Val Ala Leu Leu Arg Gly
1               5                   10                  15

Val Gln Cys Gln Val Leu Leu Val Gln Ser Gly Gly Gly Val Val Gln
            20                  25                  30

Pro Gly Arg Ser Leu Arg Ile Ser Cys Ala Ala Ser Glu Phe Thr Phe
        35                  40                  45

```
Ser Asn Tyr Gly Val His Trp Val Arg Gln Ala Pro Gly Lys Gly Leu
 50                  55                  60

Glu Trp Val Ala Gly Ile Ser Ser Asp Gly Thr Asn Arg Ile His Ala
65                  70                  75                  80

Asp Ser Leu Glu Gly Arg Phe Ala Ile Ser Arg Asp Asn Phe Glu Asn
                85                  90                  95

Thr Val Tyr Leu Gln Met Asn Ser Leu Arg Val Glu Asp Thr Ala Val
            100                 105                 110

Tyr Tyr Cys Val Arg Ser Gln Gln Pro Ser Phe Phe Asp Trp Leu Phe
        115                 120                 125

Ser Asp Tyr Trp Gly Gln Gly Thr Leu Val Ala Val Ser Ser Ala Ser
130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
            260                 265                 270

His His His His His His
        275

<210> SEQ ID NO 50
<211> LENGTH: 281
<212> TYPE: PRT
<213> ORGANISM: homosapiens

<400> SEQUENCE: 50

Met Glu Phe Gly Leu Ser Trp Val Phe Val Val Ala Ile Leu Lys Gly
1               5                   10                  15

Val Gln Cys Gln Val Gln Met Val Glu Ser Gly Gly Gly Val Val Gln
            20                  25                  30

Pro Gly Gly Ser Leu Arg Leu Ser Cys Ala Ala Ser Gly Phe Thr Phe
        35                  40                  45

Ser Ser His Gly Met His Trp Val Arg Gln Ala Pro Gly Gln Gly Leu
 50                  55                  60

Glu Trp Val Ala Leu Met Ser Tyr Asp Gly Thr Thr Glu Tyr Tyr Ala
65                  70                  75                  80

Asp Ser Val Lys Gly Arg Phe Thr Ile Ser Arg Asp Asn Ser Lys Asn
                85                  90                  95

Thr Phe Phe Leu Gln Val Asn Thr Leu Thr Ser Glu Asp Thr Ala Val
            100                 105                 110

Tyr Tyr Cys Ala Arg Asp Arg Cys Ile Ser Gly Met Cys Ser Tyr Asp
        115                 120                 125

Phe Ser Asp Gly Met Asp Val Trp Gly Gln Gly Thr Thr Val Ile Val
130                 135                 140
```

```
Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr His His His His His His
            275                 280

<210> SEQ ID NO 51
<211> LENGTH: 275
<212> TYPE: PRT
<213> ORGANISM: homosapiens

<400> SEQUENCE: 51

Met Glu Phe Gly Leu Ser Trp Val Phe Leu Val Ala Ile Leu Lys Gly
1               5                   10                  15

Val Gln Cys Glu Val His Leu Val Glu Ser Gly Gly Gly Leu Val Gln
                20                  25                  30

Pro Gly Gly Ser Leu Arg Leu Ser Cys Ala Ala Ser Gly Phe Val Phe
            35                  40                  45

Ser Ser Tyr Trp Ile His Trp Val Arg Gln Ala Pro Gly Lys Gly Leu
        50                  55                  60

Val Trp Ile Ser Thr Leu Asn Ser Asp Gly Ser Ile Thr Thr Tyr Gly
65                  70                  75                  80

Glu Ser Val Lys Gly Arg Phe Thr Ile Ser Arg Asp Asn Ala Lys Asn
                85                  90                  95

Thr Val Tyr Leu His Met Asn Ser Leu Arg Ala Glu Asp Thr Ala Val
            100                 105                 110

Tyr Tyr Cys Ala Arg Gly Met Tyr Ser Tyr Val Trp Asp Ala Leu Asp
        115                 120                 125

Ile Trp Gly Gln Gly Thr Lys Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
210                 215                 220

Val Asp His Lys Pro Ser Asn Thr Lys Val Asp Lys Thr Val Glu Arg
```

-continued

```
               225                 230                 235                 240
       Lys Cys Cys Val Glu Cys Pro Pro Cys Pro Ala Pro Val Ala Gly
                       245                 250                 255
       Pro Ser Val Phe Leu Phe Pro Pro Lys Pro Lys Asp Thr His His
                       260                 265                 270
       His His His
               275

<210> SEQ ID NO 52
<211> LENGTH: 273
<212> TYPE: PRT
<213> ORGANISM: homosapiens

<400> SEQUENCE: 52

Met Glu Phe Gly Leu Ser Trp Val Phe Leu Val Ala Val Ile Arg Gly
       1               5                   10                  15
       Val Gln Cys Gln Ala Gln Leu Val Glu Ser Gly Gly Gly Leu Val Glu
                       20                  25                  30
       Pro Gly Gly Ser Leu Arg Leu Ser Cys Ser Ala Ser Gly Phe Arg Phe
                       35                  40                  45
       Arg Asp His Tyr Met Thr Trp Ile Arg His Thr Pro Gly Lys Gly Leu
       50                  55                  60
       Glu Trp Ile Ala Tyr Ile Ser Thr Gly Gly Ser Arg Thr Phe Tyr Gly
       65                  70                  75                  80
       Asp Ser Val Thr Gly Arg Phe Thr Ile Ser Arg Asp Asn Ala Lys Asn
                       85                  90                  95
       Ser Val Tyr Leu Gln Met Asn Ser Leu Arg Val Glu Asp Thr Ala Val
                       100                 105                 110
       Tyr Tyr Cys Ala Arg Asp Asp Arg Val Phe Tyr Gly Met Asp Val Trp
                       115                 120                 125
       Gly Gln Gly Thr Thr Val Ala Val Ser Ser Ala Ser Thr Lys Gly Pro
                       130                 135                 140
       Ser Val Phe Pro Leu Ala Pro Cys Ser Arg Ser Thr Ser Glu Ser Thr
       145                 150                 155                 160
       Ala Ala Leu Gly Cys Leu Val Lys Asp Tyr Phe Pro Glu Pro Val Thr
                       165                 170                 175
       Val Ser Trp Asn Ser Gly Ala Leu Thr Ser Gly Val His Thr Phe Pro
                       180                 185                 190
       Ala Val Leu Gln Ser Ser Gly Leu Tyr Ser Leu Ser Ser Val Val Thr
                       195                 200                 205
       Val Pro Ser Ser Asn Phe Gly Thr Gln Thr Tyr Thr Cys Asn Val Asp
                       210                 215                 220
       His Lys Pro Ser Asn Thr Lys Val Asp Lys Thr Val Glu Arg Lys Cys
       225                 230                 235                 240
       Cys Val Glu Cys Pro Pro Cys Pro Ala Pro Pro Val Ala Gly Pro Ser
                       245                 250                 255
       Val Phe Leu Phe Pro Pro Lys Pro Lys Asp Thr His His His His
                       260                 265                 270
       His

<210> SEQ ID NO 53
<211> LENGTH: 275
<212> TYPE: PRT
<213> ORGANISM: homosapiens

<400> SEQUENCE: 53
```

```
Met Glu Phe Gly Leu Ser Trp Ile Val Leu Ala Ala Ile Leu Lys Gly
1               5                   10                  15

Val Gln Cys Glu Val Gln Leu Val Glu Ser Gly Gly Phe Val Lys
            20                  25                  30

Pro Gly Gly Ser Leu Arg Leu Ser Cys Ile Gly Ser Gly Phe Thr Phe
                35                  40                  45

Ser Asn Asn Gly Ile His Trp Val Arg Gln Ala Pro Gly Lys Gly Leu
    50                  55                  60

Glu Trp Val Ala Val Ile Ser Gly Asp Gly Ser Glu His Tyr Ala
65                  70                  75                  80

Asp Ser Leu Lys Gly Arg Phe Thr Ile Ser Arg Asp Asn Ser Lys Asn
                85                  90                  95

Thr Val Phe Leu Gln Met Lys Ser Leu Arg His Glu Asp Thr Ala Met
            100                 105                 110

Tyr His Cys Val Arg Ser Gly Asp Arg Ile Gly Trp Tyr Asp Phe Asp
            115                 120                 125

His Trp Gly Leu Gly Thr Leu Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Asn Phe Gly Thr Gln Thr Tyr Thr Cys Asn
            210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Val Ala Gly
                245                 250                 255

Pro Ser Val Phe Leu Phe Pro Pro Lys Pro Lys Asp Thr His His His
                260                 265                 270

His His His
        275

<210> SEQ ID NO 54
<211> LENGTH: 281
<212> TYPE: PRT
<213> ORGANISM: homosapiens

<400> SEQUENCE: 54

Met Glu Phe Gly Leu Ser Trp Val Phe Leu Val Ala Ile Leu Glu Gly
1               5                   10                  15

Val Gln Cys Glu Val His Leu Val Glu Ser Gly Gly Gly Leu Val Arg
            20                  25                  30

Pro Gly Gly Ser Leu Arg Leu Ser Cys Ala Ala Ser Gly Phe Thr Phe
                35                  40                  45

Ser Ser Tyr Ala Met His Trp Val Arg Gln Ala Pro Gly Lys Gly Leu
    50                  55                  60

Glu Trp Val Ala Val Ile Ala Tyr Asp Gly Lys Asn Lys Tyr Tyr Ala
65                  70                  75                  80

Asp Ser Val Lys Gly Arg Phe Thr Ile Ser Arg Asp Asn Pro Lys Asn
```

```
            85                  90                  95
Thr Val Tyr Leu Gln Met Asp Ser Leu Arg Gly Glu Asp Thr Ala Val
            100                 105                 110

Tyr Tyr Cys Ala Lys Asp Pro Ser Ser Gly Trp Asp Asp Tyr Ser
            115                 120                 125

Ala Met Glu Leu Trp Gly Gln Gly Thr Thr Val Thr Val Ser Ser Ala
130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
            165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Asn Phe Gly Thr Gln Thr Tyr
210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr His His His His His His His His
            275                 280

<210> SEQ ID NO 55
<211> LENGTH: 275
<212> TYPE: PRT
<213> ORGANISM: homosapiens

<400> SEQUENCE: 55

Met Glu Phe Gly Leu Ser Trp Val Phe Leu Val Ala Leu Leu Lys Gly
1               5                   10                  15

Val Gln Cys Glu Val Gln Leu Val Glu Ser Gly Gly Asp Leu Val Gln
            20                  25                  30

Pro Gly Gly Ser Leu Arg Leu Ser Cys Val Gly Ser Gly Phe Pro Phe
        35                  40                  45

Ser Ser His Trp Ile His Trp Val Arg Gln Val Pro Gly Lys Gly Leu
50                  55                  60

Met Trp Val Ser Gln Ile Tyr Asn Asp Gly Ser Arg Ala Ala Tyr Ala
65                  70                  75                  80

Asp Ser Val Lys Gly Arg Phe Thr Ile Ser Arg Asp Asn Ala Arg Asn
            85                  90                  95

Thr Ala Tyr Leu His Met Thr Ser Leu Arg Val Glu Asp Thr Gly Val
            100                 105                 110

Tyr Tyr Cys Thr Arg Ala Pro Ser Glu Val Val Ala Asp Pro Tyr Gln
            115                 120                 125

His Trp Gly Gln Gly Thr Leu Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
            165                 170                 175
```

```
Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
        210                 215                 220

Val Asp His Lys Pro Ser Asn Thr Lys Val Asp Lys Thr Val Glu Arg
225                 230                 235                 240

Lys Cys Cys Val Glu Cys Pro Cys Pro Ala Pro Pro Val Ala Gly
                245                 250                 255

Pro Ser Val Phe Leu Phe Pro Pro Lys Pro Lys Asp Thr His His His
            260                 265                 270

His His His
        275

<210> SEQ ID NO 56
<211> LENGTH: 249
<212> TYPE: PRT
<213> ORGANISM: homosapiens

<400> SEQUENCE: 56

Met Gln Leu Leu Glu Ser Gly Gly Gly Leu Val Gln Pro Gly Gly Ser
1               5                   10                  15

Leu Arg Leu Ser Cys Ala Thr Ser Gly Phe Thr Phe Ser Ser Phe Val
            20                  25                  30

Met Thr Trp Val Arg Gln Ala Pro Gly Lys Gly Leu Glu Trp Val Ser
        35                  40                  45

Thr Ile Ser Asp Gly Thr Gly Asn Thr Tyr Tyr Ala Asp Ser Val Lys
    50                  55                  60

Gly Arg Phe Thr Val Ser Arg Asp Thr Ala Glu Asn Ser Leu Phe Leu
65                  70                  75                  80

Gln Met Asn Ser Leu Arg Ala Ala Asp Thr Ala Val Tyr Tyr Cys Ala
                85                  90                  95

Arg Tyr Val Lys Pro Asp Tyr Trp Gly Gln Gly Ala Leu Val Thr Val
            100                 105                 110

Ser Ser Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Asn Phe Gly Thr
            180                 185                 190

Gln Thr Tyr Thr Cys Asn Val Asp His Lys Pro Ser Asn Thr Lys Val
        195                 200                 205

Asp Lys Thr Val Glu Arg Lys Cys Cys Val Glu Cys Pro Pro Cys Pro
    210                 215                 220

Ala Pro Pro Val Ala Gly Pro Ser Val Phe Leu Phe Pro Pro Lys Pro
225                 230                 235                 240

Lys Asp Thr His His His His His His
                245

<210> SEQ ID NO 57
```

<211> LENGTH: 277
<212> TYPE: PRT
<213> ORGANISM: homosapiens

<400> SEQUENCE: 57

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Ala Met Tyr Trp Val Arg Gln Ala Pro Gly Lys Gly Leu
    50                  55                  60

Glu Trp Val Ala Ala Ile Ser His Asp Gly Ser Asn Arg Asp Tyr Ala
65                  70                  75                  80

Asp Ser Val Thr Gly Arg Phe Thr Ile Ser Arg Asp Asn Ser Lys Asn
                85                  90                  95

Thr Phe Phe Leu Gln Met Asn Asp Leu Arg Pro Glu Thr Ala Leu
            100                 105                 110

Tyr Tyr Cys Ala Ser Arg Pro Pro Ile Gly Glu Thr Leu Arg Gly Pro
        115                 120                 125

Phe Asp Tyr Trp Gly Gln Gly Thr Leu Val Ser Val Ser Pro Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Pro Ser Gly Leu Tyr Ser Leu Ser
        195                 200                 205

Ser Val Val Thr Val Pro Ser Ser Asn Phe Cys Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
            260                 265                 270

His His His His His
        275

<210> SEQ ID NO 58
<211> LENGTH: 279
<212> TYPE: PRT
<213> ORGANISM: homosapiens

<400> SEQUENCE: 58

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Ser Leu
        35                  40                  45

Ser Ser Tyr Trp Met Ser Trp Ile Arg Gln Ser Pro Thr Gly Leu
    50                  55                  60

```
Glu Trp Val Ala Asp Thr Ala Asn Ala Arg Asp Ala Thr Tyr Tyr Val
65                  70                  75                  80

Asp Ser Val Thr Gly Arg Phe Thr Val Ser Arg Asp Asn Ala Lys Asn
                85                  90                  95

Ser Val Phe Leu Gln Met Asn Ser Leu Arg Val Glu Asp Thr Ala Val
            100                 105                 110

Tyr Tyr Cys Val Arg Thr Pro Ala Val Ala Glu Gly Gly Tyr Phe Asp
        115                 120                 125

Tyr Trp Gly Gln Gly Val Leu Val Ala Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr His His His His His His
        275

<210> SEQ ID NO 59
<211> LENGTH: 223
<212> TYPE: PRT
<213> ORGANISM: homosapiens

<400> SEQUENCE: 59

Met Ser Trp Val Arg Gln Ala Pro Gly Lys Gly Leu Glu Trp Val Gly
1               5                   10                  15

Arg Ile Asn Ser Lys Thr Asp Gly Gly Thr Thr Asp Tyr Ala Ala Pro
            20                  25                  30

Val Lys Gly Arg Phe Thr Ile Ser Arg Asp Asp Ser Lys Asn Thr Leu
        35                  40                  45

Tyr Leu Gln Met Asn Ser Leu Lys Thr Glu Asp Thr Ala Val Tyr Tyr
    50                  55                  60

Cys Thr Thr Asp Leu Gly Thr Gly Thr Thr Ala Gly Tyr Trp Gly Gln
65                  70                  75                  80

Gly Thr Leu Val Thr Val Ser Ser Ala Ser Thr Lys Gly Pro Ser Val
                85                  90                  95

Phe Pro Leu Ala Pro Cys Ser Arg Ser Thr Ser Glu Ser Thr Ala Ala
            100                 105                 110

Leu Gly Cys Leu Val Lys Asp Tyr Phe Pro Glu Pro Val Thr Val Ser
        115                 120                 125

Trp Asn Ser Gly Ala Leu Thr Ser Gly Val His Thr Phe Pro Ala Val
    130                 135                 140

Leu Gln Ser Ser Gly Leu Tyr Ser Leu Ser Ser Val Val Thr Val Pro
```

```
145                 150                 155                 160
Ser Ser Asn Phe Gly Thr Gln Thr Tyr Thr Cys Asn Val Asp His Lys
                165                 170                 175

Pro Ser Asn Thr Lys Val Asp Lys Thr Val Glu Arg Lys Cys Cys Val
                180                 185                 190

Glu Cys Pro Pro Cys Pro Val Pro Val Ala Gly Pro Ser Val Phe
                195                 200                 205

Leu Phe Pro Pro Lys Pro Lys Asp Thr His His His His His His
        210                 215                 220

<210> SEQ ID NO 60
<211> LENGTH: 277
<212> TYPE: PRT
<213> ORGANISM: homosapiens

<400> SEQUENCE: 60

Met Glu Phe Gly Leu Ser Trp Val Phe Leu Val Ala Ile Leu Glu Gly
1               5                   10                  15

Val Gln Cys Glu Val Gln Leu Met Glu Ser Gly Gly Gly Val Val Gln
            20                  25                  30

Pro Gly Arg Ser Leu Arg Leu Ser Cys Ala Gly Ser Gly Phe Thr Phe
        35                  40                  45

Ser Ser His Ala Ile His Trp Val Arg Gln Ala Pro Gly Lys Gly Leu
    50                  55                  60

Glu Trp Val Ala Leu Ile Ser Tyr Asp Gly Ser Asp Lys Tyr Tyr Ala
65                  70                  75                  80

Asp Ser Val Lys Gly Arg Phe Thr Ile Ser Arg Asp Asp Ser Lys Asn
                85                  90                  95

Thr Ile Tyr Leu Gln Met Asn Ser Leu Arg Pro Glu Asp Thr Ala Met
            100                 105                 110

Tyr Tyr Cys Val Lys Thr Met Val Arg Gly Ser Phe Tyr Tyr Tyr Gly
        115                 120                 125

Val Asp Val Trp Gly His Gly Thr Thr Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
            260                 265                 270

His His His His His
        275

<210> SEQ ID NO 61
<211> LENGTH: 273
```

<212> TYPE: PRT
<213> ORGANISM: homosapiens

<400> SEQUENCE: 61

```
Met Glu Phe Gly Leu Ser Trp Ile Phe Leu Ala Ala Thr Leu Lys Gly
1               5                   10                  15

Val Lys Cys Glu Val Gln Leu Val Glu Ser Gly Gly Gly Leu Val Lys
            20                  25                  30

Pro Ala Gly Ser Leu Arg Leu Ser Cys Glu Ala Ser Gly Phe Ala Phe
        35                  40                  45

Ser Asn Val Trp Met Thr Trp Val Arg Gln Ala Pro Gly Lys Gly Leu
    50                  55                  60

Glu Trp Val Gly Arg Ile Thr Thr Lys Ala Asp Asn Trp Gly Thr Asp
65                  70                  75                  80

Tyr Ala Ala Pro Leu Arg Gly Arg Phe Thr Ile Ser Arg Asp Asp Ser
                85                  90                  95

Lys Asn Thr Leu Tyr Leu Gln Met Asn Ser Leu Lys Thr Glu Asp Thr
            100                 105                 110

Ala Ala Tyr Tyr Cys Ala Ile Leu Asn Arg Gly Arg Phe Glu Ser Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr His His His His His
            260                 265                 270

His
```

<210> SEQ ID NO 62
<211> LENGTH: 271
<212> TYPE: PRT
<213> ORGANISM: homosapiens

<400> SEQUENCE: 62

```
Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Trp Ser Leu Arg Leu Ser Cys Ala Ala Ser Gly Phe Thr Phe
        35                  40                  45

Ser Asp Tyr Ala Met Asn Trp Val Arg Gln Ala Pro Gly Lys Gly Leu
    50                  55                  60

Asp Leu Val Cys Ser Ile Asp Asp Ser Gly His His Thr Asn Tyr Ala
```

```
                65                  70                  75                  80
Asp Ser Val Lys Gly Arg Phe Thr Ile Ser Arg Asp Asn Ser Lys Asn
                    85                  90                  95

Thr Leu Tyr Leu Gln Met Asn Ser Leu Arg Ala Glu Asp Thr Ala Val
                100                 105                 110

Tyr Tyr Cys Ala Lys Asp Thr Arg Gly Trp Ser Gln Glu Trp Gly Gln
                115                 120                 125

Gly Thr Leu Leu Ile Val Ser Ser Ala Ser Thr Lys Gly Pro Ser Val
                130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
                195                 200                 205

Ser Ser Asn Phe Gly Thr Gln Thr Tyr Thr Cys Asn Val Asp His Lys
                210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr His His His His His His
                260                 265                 270
```

<210> SEQ ID NO 63
<211> LENGTH: 284
<212> TYPE: PRT
<213> ORGANISM: homosapiens

<400> SEQUENCE: 63

```
Met Glu Phe Gly Leu Ser Trp Val Phe Leu Val Ala Ile Leu Glu Gly
1               5                   10                  15

Val Gln Cys Gly Val Gln Leu Val Glu Ser Gly Gly Gly Leu Val Gln
                20                  25                  30

Pro Gly Gly Ser Leu Arg Leu Ser Cys Ala Ala Ser Gly Phe Ala Phe
                35                  40                  45

Ser Thr Tyr Asp Met His Trp Val Arg Gln Val Ser Arg Glu Gly Leu
                50                  55                  60

Glu Trp Val Ser Gly Ile Gly Thr Ala Gly Asp Thr Tyr Tyr Ala Gly
65                  70                  75                  80

Ser Val Lys Gly Arg Phe Thr Ile Ser Arg Glu Asn Ala Lys Asn Ser
                85                  90                  95

Leu Tyr Leu Gln Met Thr Ser Leu Gly Ala Gly Asp Thr Ala Val Tyr
                100                 105                 110

Tyr Cys Val Arg Gly Leu Ser Gly Asp Tyr Gly Gly Leu Asp Tyr Tyr
                115                 120                 125

Tyr Tyr Ala Met Asp Val Trp Gly Gln Gly Thr Thr Val Ile Val Ser
                130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175
```

```
Tyr Phe Pro Glu Pro Val Thr Val Ser Trp Asn Ser Gly Ala Leu Thr
                180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
        210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr His His His His His His
        275                 280
```

<210> SEQ ID NO 64
<211> LENGTH: 229
<212> TYPE: PRT
<213> ORGANISM: homosapiens

<400> SEQUENCE: 64

```
Met Ser Trp Ile Arg Gln Ala Pro Gly Lys Gly Leu Glu Trp Leu Ser
1               5                   10                  15

Tyr Ile Gly Thr Thr Val Ser Ala Ile Tyr Tyr Ala Glu Ser Val Lys
                20                  25                  30

Gly Arg Phe Thr Ile Ser Arg Asp Asn Ala Lys Arg Ser Leu Ser Leu
            35                  40                  45

Gln Met Asn Ser Leu Arg Ala Asp Asp Thr Ala Val Tyr Tyr Cys Ala
        50                  55                  60

Lys Glu Gly Trp Gly Asp Tyr Gly Asp Tyr Tyr Gly Arg Arg Gly Val
65                  70                  75                  80

Phe Asp Ser Trp Gly Gln Gly Thr Leu Val Thr Val Ser Ser Ala Ser
                85                  90                  95

Thr Lys Gly Pro Ser Val Phe Pro Leu Ala Pro Ser Ser Lys Ser Thr
                100                 105                 110

Ser Gly Gly Thr Ala Ala Leu Gly Cys Leu Val Lys Asp Tyr Phe Pro
            115                 120                 125

Glu Pro Val Thr Val Ser Trp Asn Ser Gly Ala Leu Thr Ser Gly Val
        130                 135                 140

His Thr Phe Pro Ala Val Leu Gln Ser Ser Gly Leu Tyr Ser Leu Ser
145                 150                 155                 160

Ser Val Val Thr Val Pro Ser Ser Ser Leu Gly Thr Gln Thr Tyr Ile
                165                 170                 175

Cys Asn Val Asn His Lys Pro Ser Asn Thr Lys Val Asp Lys Thr Val
                180                 185                 190

Glu Arg Lys Cys Cys Val Glu Cys Pro Pro Cys Pro Ala Pro Pro Val
            195                 200                 205

Ala Gly Pro Ser Val Phe Leu Phe Pro Pro Lys Pro Lys Asp Thr His
        210                 215                 220

His His His His His
225
```

<210> SEQ ID NO 65
<211> LENGTH: 284
<212> TYPE: PRT
<213> ORGANISM: homosapiens

<400> SEQUENCE: 65

```
Met Glu Phe Gly Leu Ser Trp Val Phe Leu Val Ala Ile Leu Lys Gly
1               5                   10                  15

Val Gln Cys Glu Met Gln Leu Val Glu Ser Gly Gly Gly Leu Val Gln
            20                  25                  30

Pro Gly Gly Ser Leu Lys Leu Ser Cys Thr Ala Ser Gly Phe Thr Phe
        35                  40                  45

Ser Ala Pro Glu Phe Ile Phe Asn Ala Ser Ala Ile His Trp Val Arg
    50                  55                  60

Gln Ala Pro Gly Lys Gly Leu Glu Trp Leu Ala Phe Ile Ser Tyr Asp
65                  70                  75                  80

Gly Ser Asp Asp Ser Tyr Ala Asp Ser Val Lys Gly Arg Phe Thr Ile
                85                  90                  95

Ser Arg Asp Asn Ser Lys Asn Thr Val Tyr Leu Gln Met Asn Thr Leu
            100                 105                 110

Arg Ala Glu Asp Thr Ala Val Tyr Tyr Cys Ala Arg Val Ser Ala Pro
        115                 120                 125

Asp Leu Asp Ser Tyr Gly Ser Leu Phe Tyr Trp Gly Gln Gly Thr Leu
    130                 135                 140

Val Thr Val Ser Ser Ala Ser Thr Lys Gly Pro Ser Val Phe Pro Leu
145                 150                 155                 160

Ala Pro Cys Ser Arg Ser Thr Ser Glu Ser Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Asn
    210                 215                 220

Phe Gly Thr Gln Thr Tyr Thr Cys Asn Val Asp His Lys Pro Ser Asn
225                 230                 235                 240

Thr Lys Val Asp Lys Thr Val Glu Arg Lys Cys Cys Val Glu Cys Pro
                245                 250                 255

Pro Cys Pro Ala Pro Pro Val Ala Gly Pro Ser Val Phe Leu Phe Pro
            260                 265                 270

Pro Lys Pro Lys Asp Thr His His His His His His
        275                 280
```

<210> SEQ ID NO 66
<211> LENGTH: 275
<212> TYPE: PRT
<213> ORGANISM: homosapiens

<400> SEQUENCE: 66

```
Met Glu Phe Gly Leu Ser Trp Val Leu Leu Val Ala Leu Ile Arg Gly
1               5                   10                  15

Val Gln Cys Gln Val Gln Leu Val Glu Ser Gly Gly Gly Val Val Gln
            20                  25                  30

Pro Gly Thr Ser Leu Arg Leu Ser Cys Ala Ala Ser Gly Phe Ser Phe
        35                  40                  45

Ser Asn Tyr Val Met His Trp Val Arg Gln Ala Pro Gly Lys Gly Leu
    50                  55                  60

Glu Trp Val Ser Ser Ile Trp Phe Asp Gly Ser Gln Lys Trp Tyr Val
65                  70                  75                  80
```

-continued

```
Asp Ser Val Lys Gly Arg Phe Thr Ile Ser Arg Asp Lys Tyr Glu Asn
                85                  90                  95

Thr Val Ser Leu Gln Met Asp Ser Leu Arg Ala Glu Asp Thr Ala Val
            100                 105                 110

Tyr Tyr Cys Ala Arg Glu Gly Pro Gly Ala Gly Thr Gly Gly Phe Asp
        115                 120                 125

Tyr Trp Gly Gln Gly Ile Leu Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr His His His
            260                 265                 270

His His His
        275

<210> SEQ ID NO 67
<211> LENGTH: 228
<212> TYPE: PRT
<213> ORGANISM: homosapiens

<400> SEQUENCE: 67

Met Ser Trp Val Arg Gln Ala Pro Gly Lys Gly Leu Glu Trp Val Ser
1               5                   10                  15

Thr Ile Asn Gly Asp Ala Asp Asn Val Tyr Tyr Thr Asp Ser Val Lys
            20                  25                  30

Gly Arg Phe Ser Ile Ser Arg Asp Asn Ser Lys Asn Thr Leu Tyr Leu
        35                  40                  45

Gln Met Asn Ser Leu Ser Val Glu Asp Thr Ala Ile Tyr Tyr Cys Ala
    50                  55                  60

Lys Asp Ile Val Arg Ala Met Cys His Gly Gly Ser Cys Tyr Pro Phe
65                  70                  75                  80

Asp Tyr Trp Gly Gln Gly Thr Leu Val Thr Val Ser Ser Ala Ser Thr
                85                  90                  95

Lys Gly Pro Ser Val Phe Pro Leu Ala Pro Cys Ser Arg Ser Thr Ser
            100                 105                 110

Glu Ser Thr Ala Ala Leu Gly Cys Leu Val Lys Asp Tyr Phe Pro Glu
        115                 120                 125

Pro Val Thr Val Ser Trp Asn Ser Gly Ala Leu Thr Ser Gly Val His
    130                 135                 140

Thr Phe Pro Ala Val Leu Gln Ser Ser Gly Leu Tyr Ser Leu Ser Ser
145                 150                 155                 160

Val Val Thr Val Pro Ser Ser Asn Phe Gly Thr Gln Thr Tyr Thr Cys
```

```
                    165                 170                 175
Asn Val Asp His Lys Pro Ser Asn Thr Lys Val Asp Lys Thr Val Glu
                180                 185                 190

Arg Lys Cys Cys Val Glu Cys Pro Cys Pro Ala Pro Pro Val Ala
            195                 200                 205

Gly Pro Ser Val Phe Leu Pro Pro Lys Pro Lys Asp Thr His His
        210                 215                 220

His His His His
225

<210> SEQ ID NO 68
<211> LENGTH: 275
<212> TYPE: PRT
<213> ORGANISM: homosapiens

<400> SEQUENCE: 68

Met Glu Phe Gly Leu Ser Trp Val Phe Leu Val Ala Leu Leu Arg Gly
1               5                   10                  15

Val His Cys Gln Val Gln Leu Val Glu Ser Gly Gly Gly Val Val Gln
                20                  25                  30

Pro Gly Gly Ser Leu Arg Leu Ser Cys Ala Ala Ser Gly Phe Asn Phe
            35                  40                  45

Asn Asn Tyr Pro Met His Trp Val Arg Gln Ala Pro Gly Lys Gly Leu
        50                  55                  60

Glu Trp Val Ala Ile Ile Leu Asp Asp Gly Arg Gly Arg Tyr Tyr Ala
65                  70                  75                  80

Asp Ser Val Lys Gly Arg Phe Ile Ile Ser Arg Asp Ile Ser Lys Ser
                85                  90                  95

Thr Leu His Leu Gln Met Asp Ser Leu Arg Pro Asp Asp Ser Ala Met
                100                 105                 110

Tyr Tyr Cys Ala Lys Glu Thr Arg Pro Asn Gly Asp Ser Ala Cys Asp
            115                 120                 125

Ser Trp Gly Gln Gly Thr Arg Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Asn Phe Gly Thr Gln Thr Tyr Thr Cys Asn
        210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Ala Ala Gly
                245                 250                 255

Pro Ser Val Phe Leu Phe Pro Pro Lys Pro Lys Asp Ser His His His
                260                 265                 270

His His His
        275

<210> SEQ ID NO 69
<211> LENGTH: 280
```

<212> TYPE: PRT
<213> ORGANISM: homosapiens

<400> SEQUENCE: 69

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Ala Met Thr Trp Val Arg Gln Ala Pro Gly Lys Gly Leu
    50                  55                  60

Glu Trp Val Ser Gly Ile Ser Gly Ser Gly Val Ala Thr Lys Tyr Ala
65                  70                  75                  80

Tyr Ala Asp Ser Val Lys Gly Arg Phe Thr Ile Ser Arg Asp Asn Ala
                85                  90                  95

Lys Asn Thr Leu Tyr Leu Gln Met Asn Ser Leu Ser Ala Glu Asp Thr
            100                 105                 110

Ala Val Tyr Tyr Cys Ala Lys Val Cys Pro Ile Cys Gly Ser Glu Trp
        115                 120                 125

His Asp Pro Leu Asp Ile Trp Gly Gln Gly Thr Met Val Thr Val Ser
130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr His His His His His His
        275                 280

<210> SEQ ID NO 70
<211> LENGTH: 269
<212> TYPE: PRT
<213> ORGANISM: homosapiens

<400> SEQUENCE: 70

Met Asp Phe Gly Leu Ser Trp Ile Val Leu Ala Ala Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Thr Ser Gly Phe Pro Phe
        35                  40                  45

Ser Asn Thr Trp Met Ser Trp Val Arg Gln Ala Pro Gly Lys Gly Leu
    50                  55                  60

Glu Trp Val Gly Arg Ile His Ser Lys Thr Asp Gly Gly Thr Ile Asp
65                  70                  75                  80

Tyr Ala Ala Val Arg Gly Arg Phe Thr Met Ser Lys Asp Asp Ser
                85                  90                  95

Thr Ser Thr Leu Tyr Leu Gln Met Asn Ser Leu Gln Ile Asp Asp Thr
                100                 105                 110

Ala Val Tyr Tyr Cys Thr Arg Arg Ser Ser Met Gly Gly Gln Gly Thr
                115                 120                 125

Leu Val Ile Val Ser Ser Ala Ser Thr Lys Gly Pro Ser Val Phe Pro
                130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
                180                 185                 190

Ser Ser Gly Leu Tyr Ser Leu Ser Ser Val Val Thr Val Pro Ser Ser
                195                 200                 205

Asn Phe Gly Thr Gln Thr Tyr Thr Cys Asn Val Asp His Lys Pro Ser
                210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Asn His His His His His His
                260                 265

<210> SEQ ID NO 71
<211> LENGTH: 273
<212> TYPE: PRT
<213> ORGANISM: homosapiens

<400> SEQUENCE: 71

Met Leu Phe Gly Leu Ser Trp Val Phe Leu Val Ala Ile Leu Lys Gly
1               5                   10                  15

Val Gln Cys Ala Val Gln Leu Val Glu Ser Gly Gly Gly Val Val Gln
                20                  25                  30

Pro Gly Gly Ser Leu Arg Leu Ser Cys Ala Ala Ser Gly Phe Thr Leu
                35                  40                  45

Asp Asp Tyr Val Ile His Trp Val Arg Gln Ala Pro Arg Lys Gly Leu
                50                  55                  60

Glu Trp Val Ser Ile Arg Gly Val Asp Asp Thr Thr Tyr Tyr Ala
65                  70                  75                  80

Asp Ser Val Arg Gly Arg Phe Thr Val Ser Arg Asp Asn Ser Lys Asn
                85                  90                  95

Ser Leu Tyr Leu Gln Met Asn Asn Leu Arg Ala Asp Asp Thr Ala Ile
                100                 105                 110

Tyr Phe Cys Ala Arg Leu Asn Pro Ala Met Val Glu Phe Asp Tyr Trp
                115                 120                 125

Gly Gln Gly Thr Leu Val Thr Val Ser Ser Ala Ser Thr Lys Gly Pro
                130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

```
Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
            195                 200                 205

Val Pro Ser Ser Asn Phe Gly Thr Gln Thr Tyr Thr Cys Asn Val Asp
            210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
            245                 250                 255

Val Phe Leu Phe Pro Pro Lys Pro Lys Asp Thr His His His His His
            260                 265                 270

His

<210> SEQ ID NO 72
<211> LENGTH: 273
<212> TYPE: PRT
<213> ORGANISM: homosapiens

<400> SEQUENCE: 72

Met Glu Phe Gly Leu Ser Trp Val Phe Leu Val Ala Ile Leu Gln Gly
1               5                   10                  15

Val Gln Cys Glu Val Gln Leu Val Glu Ser Gly Gly Asp Leu Val Arg
            20                  25                  30

Pro Gly Gly Ser Leu Arg Leu Ser Cys Val Gly Ser Gly Phe Thr Phe
            35                  40                  45

Ser Asp His Phe Met Asp Trp Val Arg Gln Ala Thr Gly Lys Gly Leu
50                  55                  60

Glu Trp Val Ala Arg Ile Arg Asn Glu Gly Asn Arg Phe Pro Thr Glu
65                  70                  75                  80

Tyr Ala Ala Ser Val Lys Asp Arg Phe Thr Ile Ser Arg Asp Asp Ser
            85                  90                  95

Lys Thr Ser Val Phe Leu His Met Asn Ser Leu Lys Thr Glu Asp Thr
            100                 105                 110

Ala Val Tyr Tyr Cys Ala Arg Asp Tyr Gln Gly Leu Gly Thr Ser Trp
            115                 120                 125

Gly Gln Gly Thr Leu Val Thr Val Ser Ser Ala Ser Thr Lys Gly Pro
            130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
            165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
            195                 200                 205

Val Pro Ser Ser Asn Phe Gly Thr Gln Thr Tyr Thr Cys Asn Val Asp
            210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
            245                 250                 255

Val Phe Leu Phe Pro Pro Lys Pro Lys Asp Thr His His His His
            260                 265                 270
```

His

<210> SEQ ID NO 73
<211> LENGTH: 267
<212> TYPE: PRT
<213> ORGANISM: homosapiens

<400> SEQUENCE: 73

```
Met Glu Phe Gly Leu Ser Trp Val Phe Leu Val Ala Leu Leu Arg Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser His Trp Met Ser Trp Val Arg Gln Pro Pro Lys Gly Leu
    50                  55                  60

Glu Trp Val Ala Asn Ile Lys Gln Asp Gly Ser Val Lys Gln Tyr Val
65                  70                  75                  80

Asp Ser Val Lys Gly Arg Phe Thr Ile Ser Arg Asp Asn Ala Lys Lys
                85                  90                  95

Ser Val Tyr Leu Gln Met Asn Ser Leu Arg Val Glu Asp Met Ala His
            100                 105                 110

Tyr Tyr Cys Val Arg Glu Trp Gly Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Asn Phe
        195                 200                 205

Gly Thr Gln Thr Tyr Thr Cys Asn Val Asp His Lys Pro Ser Asn Thr
    210                 215                 220

Lys Val Asp Lys Thr Val Glu Arg Lys Cys Cys Val Glu Cys Pro Ala
225                 230                 235                 240

Cys Pro Ala Pro Pro Val Ala Gly Pro Ser Val Phe Leu Phe Pro Pro
                245                 250                 255

Lys Pro Lys Asp Thr His His His His His His
            260                 265
```

<210> SEQ ID NO 74
<211> LENGTH: 279
<212> TYPE: PRT
<213> ORGANISM: homosapiens

<400> SEQUENCE: 74

```
Met Glu Ser Gly Leu Ser Trp Val Phe Leu Val Ala Ile Leu Glu Gly
1               5                   10                  15

Val Gln Cys Ala Val Gln Leu Val Glu Ser Gly Gly Ala Leu Val Gln
            20                  25                  30

Pro Gly Gly Ser Leu Arg Leu Ser Cys Val Gly Ser Gly Phe Thr Leu
        35                  40                  45
```

```
Ser Thr Tyr Trp Met Thr Trp Val Arg Gln Ala Pro Gly Arg Gly Leu
    50                  55                  60

Glu Trp Val Ala Asn Leu Lys Val Asp Gly Ser Val Asp His Tyr Val
65                  70                  75                  80

Asp Ser Val Lys Gly Arg Phe Thr Ile Ser Arg Asp Asn Ala Lys Asn
                85                  90                  95

Ser Leu Tyr Leu Gln Ile Asn Ser Leu Lys Leu Glu Tyr Thr Ala Val
            100                 105                 110

Tyr Tyr Cys Ala Arg Tyr Arg Thr Tyr Cys Asp Gly Pro Val Cys Tyr
            115                 120                 125

Asp Val Phe Asp Ile Trp Gly Gln Gly Thr Met Val Thr Val Ser Ser
130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Asn Phe Gly Thr Gln Thr
210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr His His His His His His
            275

<210> SEQ ID NO 75
<211> LENGTH: 270
<212> TYPE: PRT
<213> ORGANISM: homosapiens

<400> SEQUENCE: 75

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Ala Leu Leu Leu
                20                  25                  30

Pro Gly Gly Ser Leu Thr Leu Ser Cys Glu Val Ser Gly Phe Ser Val
            35                  40                  45

Ser Asp Asn Tyr Met Asn Trp Leu Arg Gln Ala Pro Gly Lys Gly Leu
        50                  55                  60

Glu Trp Val Ala Thr Leu Tyr Thr Gly Gly Asn Thr Tyr Tyr Ser Asp
65                  70                  75                  80

Ser Val Lys Gly Arg Phe Thr Ile Ser Arg Glu Asp Ser Lys Asn Val
                85                  90                  95

Leu Tyr Leu Gln Met Asn Ser Leu Arg Val Glu Glu Thr Ala Arg Tyr
            100                 105                 110

Phe Cys Val Arg Gly Met Arg Gly Ile Ser His Asp Trp Gly Gln Gly
            115                 120                 125

Thr Leu Val Thr Val Ser Ser Ala Ser Thr Lys Gly Pro Ser Val Phe
130                 135                 140
```

```
Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr His His His His His His
                260                 265                 270
```

<210> SEQ ID NO 76
<211> LENGTH: 275
<212> TYPE: PRT
<213> ORGANISM: homosapiens

<400> SEQUENCE: 76

```
Met Glu Phe Gly Leu Ser Trp Val Phe Leu Val Ala Leu Leu Arg Gly
1               5                   10                  15

Val His Cys Gln Val Gln Val Glu Ser Gly Gly Gly Val Val Gln
                20                  25                  30

Pro Gly Lys Ser Leu Thr Leu Ser Cys Ala Ala Ser Thr Phe Thr Phe
            35                  40                  45

Ser Asn Tyr Ala Val His Trp Val Arg Gln Ala Pro Gly Lys Gly Leu
    50                  55                  60

Glu Trp Val Ala Val Ile Ser Tyr Asp Gly Ser Thr Lys Asn Tyr Ala
65                  70                  75                  80

Asp Ser Val Gln Gly Arg Phe Thr Ile Ser Arg Asp Asn Ser Asn Asn
                85                  90                  95

Thr Leu Phe Leu Gln Met Asn Ser Leu Arg Phe Glu Asp Thr Ala Phe
                100                 105                 110

Tyr Tyr Cys Ala Arg Asp Pro Ser Gly Arg Tyr Thr Leu Asp Phe Trp
            115                 120                 125

Gly Gln Gly Thr Leu Val Thr Val Ser Ser Ala Ser Thr Lys Gly Pro
        130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
```

-continued

```
                    245                 250                 255
Val Phe Leu Phe Pro Pro Lys Pro Lys Asp Thr His His His His
            260                 265                 270
His His His
        275

<210> SEQ ID NO 77
<211> LENGTH: 271
<212> TYPE: PRT
<213> ORGANISM: homosapiens

<400> SEQUENCE: 77

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Lys Ser Leu Arg Leu Ser Cys Ala Val Ser Gly Phe Asn Phe
        35                  40                  45

Ser Ala Tyr Gly Met His Trp Val Arg Gln Ala Pro Gly Lys Gly Leu
    50                  55                  60

Glu Trp Val Ala Val Trp His Asp Glu Ile Asn Lys Ile Tyr Ala
65                  70                  75                  80

Asp Ser Val Lys Gly Arg Phe Ser Ile Ser Arg Asp Asn Ser Glu Asn
                85                  90                  95

Val Met Tyr Leu Gln Met Asn Ser Leu Arg Val Glu Asp Thr Gly Leu
            100                 105                 110

Tyr Phe Cys Val Arg Asp Gln Asn Tyr Ile Phe Asp Phe Trp Gly Gln
        115                 120                 125

Gly Thr Val Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
    210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Val Ala Gly Pro Ser Val Phe
                245                 250                 255

Leu Phe Pro Pro Lys Pro Lys Asp Thr His His His His His His
            260                 265                 270

<210> SEQ ID NO 78
<211> LENGTH: 279
<212> TYPE: PRT
<213> ORGANISM: homosapiens

<400> SEQUENCE: 78

Met Glu Phe Gly Leu Ser Trp Val Phe Leu Val Ala Leu Leu Arg Gly
1               5                   10                  15

Val Gln Cys Gln Val Gln Leu Glu Glu Ser Gly Gly Gly Val Val Gln
```

```
            20                  25                  30
Pro Gly Arg Ser Leu Arg Leu Ser Cys Ala Gly Ser Gly Phe Ser Phe
            35                  40                  45

Ser Ser Tyr Ala Ile His Trp Val Arg Gln Ala Pro Gly Lys Gly Leu
    50                  55                  60

Glu Trp Val Gly Val Ile Ser Ser Asp Glu Phe Thr Lys Tyr Tyr Ala
65                  70                  75                  80

Asp Ser Val Lys Gly Arg Phe Thr Ile Ser Arg Asp Asn Ser Lys Asn
                85                  90                  95

Thr Val Tyr Met Gln Leu Asn Ile Leu Arg Thr Glu Asp Thr Ala Val
            100                 105                 110

Tyr Tyr Cys Ala Thr Gly Gly Ile Tyr Gly Ser Gly Pro Arg Val Asp
            115                 120                 125

Tyr Trp Gly Gln Gly Thr Leu Leu Thr Val Ser Ala Ser Thr Lys
            130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
            210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Asn His His His His His
            275

<210> SEQ ID NO 79
<211> LENGTH: 278
<212> TYPE: PRT
<213> ORGANISM: homosapiens

<400> SEQUENCE: 79

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Glu
            20                  25                  30

Pro Gly Gly Ser Leu Arg Leu Ser Cys Ala Ala Ser Gly Phe Thr Phe
            35                  40                  45

Ser Ser Tyr Val Met Ser Trp Val Arg Gln Ala Pro Gly Lys Gly Leu
    50                  55                  60

Glu Trp Val Ser Gly Met Ser Gly Gly Ala Arg Gly Ile Tyr Tyr Ala
65                  70                  75                  80

Asp Ser Val Gln Gly Arg Phe Thr Ile Ser Arg Asp Asn Ser Lys Asn
                85                  90                  95

Thr Leu Tyr Leu Gln Met Ser Ser Leu Arg Ala Glu Asp Thr Ala Val
            100                 105                 110
```

Tyr Tyr Cys Thr Arg Asp Gln Phe Gly Ser Gly Trp Ser Ala Asp Tyr
            115                 120                 125

Cys Phe Asp Phe Trp Gly Gln Gly Thr Val Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
            165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
            245                 250                 255

Val Ala Gly Pro Ser Val Phe Val Phe Pro Pro Lys Pro Lys Asp Thr
            260                 265                 270

His His His His His His
            275

<210> SEQ ID NO 80
<211> LENGTH: 279
<212> TYPE: PRT
<213> ORGANISM: homosapiens

<400> SEQUENCE: 80

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Val Val Gln
            20                  25                  30

Pro Gly Gly Ser Leu Arg Leu Ser Cys Thr Ala Ser Gly Phe Thr Phe
            35                  40                  45

Ala Asp Tyr Ala Met His Trp Val Arg Gln Ala Pro Gly Lys Gly Leu
    50                  55                  60

Glu Trp Leu Ser Leu Ile Ser Gly Lys Asp Gly Ser Thr Tyr Tyr Ala
65                  70                  75                  80

Ala Ser Val Arg Gly Arg Phe Thr Ile Ser Arg Asp Asn Ser Lys Asn
            85                  90                  95

Ser Leu Tyr Leu Glu Met Ser Ser Leu Arg Thr Asp Asp Thr Ala Phe
            100                 105                 110

Tyr Tyr Cys Ala Lys Asp Lys Asp Asp Ser Arg Arg Gln Ala Pro Pro
            115                 120                 125

Asp Ala Phe Asp Gln Trp Gly Gln Gly Thr Leu Val Thr Val Ser Ser
    130                 135                 140

Thr Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
            165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
            195                 200                 205

```
Leu Ser Ser Val Val Thr Val Pro Ser Ser Asn Phe Gly Thr Gln Thr
    210                 215                 220
Tyr Thr Cys Asn Val Asp His Lys Pro Ser Asn Thr Lys Val Asp Lys
225                 230                 235                 240
Thr Val Glu Arg Lys Cys Cys Val Glu Cys Pro Pro Cys Pro Ala Pro
                245                 250                 255
Pro Val Ala Gly Pro Ser Val Phe Leu Phe Pro Pro Lys Pro Lys Asp
                260                 265                 270
Thr His His His His His His
    275
```

<210> SEQ ID NO 81
<211> LENGTH: 271
<212> TYPE: PRT
<213> ORGANISM: homosapiens

<400> SEQUENCE: 81

```
Met Glu Phe Gly Leu Ser Trp Ile Phe Leu Val Ala Ile Leu Lys Gly
1               5                   10                  15
Val Arg Cys Glu Val Gln Leu Val Gly Ser Gly Gly Gly Leu Val Lys
            20                  25                  30
Pro Gly Glu Ser Leu Arg Leu Ser Cys Ala Ala Ser Glu Phe Thr Phe
        35                  40                  45
Ser Asn Ala Trp Met Asn Trp Val Arg Gln Ala Pro Gly Lys Gly Leu
    50                  55                  60
Glu Trp Val Gly Arg Ile Lys Ser Arg Ala Asp Gly Gly Thr Thr Val
65                  70                  75                  80
Tyr Ala Ala Pro Val Lys Gly Arg Phe Thr Ile Ser Arg Asp Asp Ser
                85                  90                  95
Lys Asn Thr Leu Tyr Leu Gln Met Asn Ser Leu Lys Thr Glu Asp Thr
            100                 105                 110
Gly Met Tyr Tyr Cys Thr Asn Asn Gly Leu Pro Gln Tyr Trp Gly Gln
        115                 120                 125
Gly Thr Gln Val Thr Val Ser Ser Ala Ser Thr Lys Gly Pro Ser Val
    130                 135                 140
Phe Pro Leu Ala Pro Cys Ser Arg Ser Thr Ser Glu Ser Thr Ala Ala
145                 150                 155                 160
Leu Gly Cys Leu Val Lys Asp Tyr Phe Pro Glu Pro Val Thr Val Ser
                165                 170                 175
Trp Asn Ser Gly Ala Leu Thr Ser Gly Val His Thr Phe Pro Ala Val
            180                 185                 190
Leu Gln Ser Ser Gly Leu Tyr Ser Leu Ser Ser Val Val Thr Val Pro
        195                 200                 205
Ser Ser Asn Phe Gly Thr Gln Thr Tyr Ser Cys Asn Val Asp His Lys
    210                 215                 220
Pro Ser Asn Thr Lys Val Asp Lys Thr Val Glu Arg Lys Cys Cys Val
225                 230                 235                 240
Glu Cys Pro Pro Cys Pro Ala Pro Pro Val Ala Gly Pro Ser Val Phe
                245                 250                 255
Leu Phe Pro Pro Lys Pro Lys Asp Ile His His His His His His
            260                 265                 270
```

<210> SEQ ID NO 82
<211> LENGTH: 274
<212> TYPE: PRT

<213> ORGANISM: homosapiens

<400> SEQUENCE: 82

Met Lys Phe Gly Leu Ser Trp Val Phe Leu Val Ala Phe Leu Glu Gly
1               5                   10                  15

Val Pro Cys Glu Val Gln Leu Val Glu Ser Gly Gly Gly Leu Val Gln
            20                  25                  30

Pro Gly Gly Ser Leu Arg Leu Ser Cys Glu Gly Ser Gly Leu Ser Leu
        35                  40                  45

Ser Ser Tyr Glu Met Asn Trp Val Arg Gln Ala Pro Gly Lys Gly Leu
    50                  55                  60

Glu Trp Val Ser Tyr Ile Gly Thr Ser Asp Val Ser Val Asn Tyr Val
65                  70                  75                  80

Asp Ser Val Trp Gly Arg Phe Thr Thr Ser Arg Asp Asn Ala Lys Asn
                85                  90                  95

Ile Val Tyr Leu Gln Met Ser Ser Leu Arg Val Glu Asp Thr Ala Val
            100                 105                 110

Tyr Tyr Cys Ala Ser Asp Ser His Gly Ser Cys Asp Phe Trp Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr His His His His
            260                 265                 270

His His

<210> SEQ ID NO 83
<211> LENGTH: 279
<212> TYPE: PRT
<213> ORGANISM: homosapiens

<400> SEQUENCE: 83

Met Lys Phe Gly Leu Ser Trp Val Phe Leu Ala Ala Leu Leu Arg Gly
1               5                   10                  15

Val Gln Cys Gln Glu Gln Leu Met Glu Ser Gly Gly Gly Val Val Gln
            20                  25                  30

Pro Gly Arg Ser Leu Arg Leu Ser Cys Ala Ala Ser Gly Phe Ile Leu
        35                  40                  45

Ser Asp Tyr Ala Leu His Trp Ala Arg Gln Ala Pro Gly Lys Arg Pro
    50                  55                  60

Glu Ser Leu Ala Val Met Ser Tyr Asp Glu Thr Asn Thr Tyr Tyr Ala
65                  70                  75                  80

```
Asp Ser Val Met Gly Arg Phe Thr Ile Ser Arg Asp Ser Ser Lys Asn
                85                  90                  95

Thr Leu Tyr Leu His Met Asn Ser Leu Thr Ser Glu Asp Thr Ala Val
            100                 105                 110

Tyr Tyr Cys Ala Arg Gly Gly Tyr His Asp Val Thr Gly Tyr His Tyr
        115                 120                 125

Thr Asp Phe Trp Gly Gln Gly Thr Leu Val Thr Val Ser Ser Ala Ser
130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
            165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
            195                 200                 205

Ser Val Val Thr Val Pro Ser Ser Asn Phe Gly Thr Gln Thr Tyr Thr
        210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Pro Val Phe Leu Phe Pro Pro Lys Pro Lys Asp Thr His
            260                 265                 270

His His His His His His
            275

<210> SEQ ID NO 84
<211> LENGTH: 277
<212> TYPE: PRT
<213> ORGANISM: homosapiens

<400> SEQUENCE: 84

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Lys Ser Leu Arg Leu Ser Cys Ala Gly Thr Gly Tyr Ile Phe
        35                  40                  45

Arg Ser Tyr Arg Met His Trp Val Arg Gln Ala Pro Gly Lys Gly Leu
    50                  55                  60

Glu Trp Leu Thr Thr Ile Thr Tyr Asp Gly Leu Asn Thr Asp Tyr Ala
65                  70                  75                  80

Asp Ser Val Lys Gly Arg Leu Thr Val Ser Arg Asp Asn Ser Gln Asn
                85                  90                  95

Thr Leu Phe Leu Gln Met Asn Ser Leu Arg Pro Asp Asp Thr Ala Val
            100                 105                 110

Tyr Tyr Cys Ala Arg Glu Ala Glu Tyr Glu Gly Arg Gly Trp Tyr Tyr
        115                 120                 125

Phe Ala His Trp Gly Gln Gly Thr Leu Val Thr Val Ser Ser Ala Ser
130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
```

```
                    165                 170                 175
Glu Pro Val Thr Val Ser Trp Asn Ser Gly Ala Leu Thr Ser Gly Val
                180                 185                 190
His Thr Phe Pro Ala Val Leu Gln Ser Ser Gly Leu Tyr Ser Leu Ser
                195                 200                 205
Ser Val Val Thr Val Ser Ser Asn Phe Gly Thr Gln Thr Tyr Thr
                210                 215                 220
Cys Asn Val Asp His Lys Pro Ser Asn Thr Lys Val Asp Lys Thr Val
225                 230                 235                 240
Glu Arg Lys Cys Cys Val Glu Cys Pro Pro Cys Pro Ala Pro Pro Val
                245                 250                 255
Ala Gly Pro Ser Val Phe Leu Phe Pro Pro Lys Pro Lys Asp Thr His
                260                 265                 270
His His His His His
                275

<210> SEQ ID NO 85
<211> LENGTH: 273
<212> TYPE: PRT
<213> ORGANISM: homosapiens

<400> SEQUENCE: 85

Met Glu Phe Gly Leu Ser Trp Val Phe Leu Val Ala Leu Leu Arg Gly
1               5                   10                  15
Val Gln Cys Gln Met Gln Leu Val Asp Ser Gly Gly Gly Val Val Gln
                20                  25                  30
Pro Gly Gly Ser Leu Arg Val Ser Cys Ala Ala Ser Gly Phe Ser Phe
                35                  40                  45
Ser Asn Tyr Trp Met Ser Trp Val Arg Gln Ala Pro Gly Lys Gly Leu
            50                  55                  60
Glu Trp Val Ala Asn Ile Asn Gln Asp Gly Ser Glu Lys His Tyr Val
65                  70                  75                  80
Ala Ser Val Glu Gly Arg Phe Thr Ile Ser Arg Asp Asn Ala Lys Asn
                85                  90                  95
Ser Leu Tyr Leu Gln Met Asn Ser Leu Arg Ala Glu Asp Thr Ala Val
                100                 105                 110
Tyr Tyr Cys Ser Arg Ile Ile Asp Ala Tyr Asp Thr Ile Asp Tyr Trp
                115                 120                 125
Gly Gln Gly Thr Leu Val Thr Val Ser Ser Ala Ser Thr Lys Gly Pro
            130                 135                 140
Ser Val Phe Pro Leu Ala Pro Cys Ser Arg Ser Thr Ser Glu Ser Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
                180                 185                 190
Ala Val Leu Gln Ser Ser Gly Leu Tyr Ser Leu Ser Ser Val Val Thr
                195                 200                 205
Val Pro Ser Ser Asn Phe Gly Thr Gln Thr Tyr Thr Cys Asn Val Asp
                210                 215                 220
His Lys Pro Ser Asn Thr Lys Val Asp Lys Thr Val Glu Arg Lys Cys
225                 230                 235                 240
Cys Val Glu Cys Pro Pro Cys Pro Ala Pro Pro Val Ala Gly Pro Ser
                245                 250                 255
```

```
Val Phe Leu Phe Pro Pro Lys Pro Lys Asp Thr His His His His
            260             265             270

His

<210> SEQ ID NO 86
<211> LENGTH: 279
<212> TYPE: PRT
<213> ORGANISM: homosapiens

<400> SEQUENCE: 86

Met Glu Phe Gly Leu Ser Trp Val Phe Leu Val Ala Phe Leu Lys Gly
1               5                   10                  15

Val Gln Cys Glu Val Leu Leu Ala Glu Ser Gly Gly Gly Val Val Gln
            20                  25                  30

Pro Gly Gly Ser Leu Arg Leu Ser Cys Ala Ala Ser Glu Phe Asn Phe
        35                  40                  45

Val Glu Tyr Thr Met Asn Trp Val Arg Gln Ala Pro Gly Lys Gly Leu
    50                  55                  60

Glu Trp Val Ala Phe Ile Arg Val Thr Gly Asp Thr Ala Tyr Gly Gly
65                  70                  75                  80

His Pro Tyr Tyr Ala Ala Ser Val Glu Gly Arg Phe Val Ile Ser Arg
                85                  90                  95

Asp Asp Ser Lys Lys Thr Leu Tyr Leu Gln Met Asn Ser Leu Arg Ser
            100                 105                 110

Gly Asp Thr Ala Ile Tyr Tyr Cys Ala Arg Gly Ser Arg Arg Arg Trp
        115                 120                 125

Glu Val Leu Asp Tyr Trp Gly Gln Gly Ala Leu Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr His His Asn His His His
        275

<210> SEQ ID NO 87
<211> LENGTH: 279
<212> TYPE: PRT
<213> ORGANISM: homosapiens

<400> SEQUENCE: 87

Met Glu Phe Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
```

```
            20                  25                  30
Pro Gly Arg Ser Leu Arg Leu Ser Cys Ala Ala Ser Gly Phe Thr Phe
        35                  40                  45
Asp Ala Tyr Ala Met His Trp Val Arg Gln Ala Pro Gly Arg Gly Leu
    50                  55                  60
Glu Trp Val Ser Gly Ile Ser Trp Asn Ser Gly Asp Ile Asp Tyr Ala
65                  70                  75                  80
Asp Ser Val Lys Gly Arg Phe Ser Ile Ser Arg Asp Asn Ala Lys His
                85                  90                  95
Ser Leu Tyr Leu Gln Met Asn Ser Leu Arg Thr Glu Asp Thr Ala Leu
            100                 105                 110
Tyr Tyr Cys Thr Lys Asp Ala Ile Arg Tyr Gly Ser Gly Asn His Pro
        115                 120                 125
Phe Phe Phe Asp Asn Trp Gly Gln Gly Thr Leu Val Thr Val Ser Ser
    130                 135                 140
Ala Ser Thr Lys Gly Pro Ser Val Phe Pro Leu Ala Pro Ser Ser Lys
145                 150                 155                 160
Ser Thr Ser Gly Gly Thr Ala Ala Leu Gly Cys Leu Val Lys Asp Tyr
                165                 170                 175
Phe Pro Glu Pro Val Thr Val Ser Trp Asn Ser Gly Ala Leu Thr Ser
            180                 185                 190
Gly Val His Thr Phe Pro Ala Val Leu Gln Ser Ser Gly Leu Tyr Ser
        195                 200                 205
Leu Ser Ser Val Val Thr Val Pro Ser Ser Asn Phe Gly Thr Gln Thr
    210                 215                 220
Tyr Thr Cys Asn Val Asp His Lys Pro Ser Asn Thr Lys Val Asp Lys
225                 230                 235                 240
Thr Val Glu Arg Lys Cys Cys Val Glu Cys Pro Pro Cys Pro Ala Pro
                245                 250                 255
Pro Val Ala Gly Pro Ser Val Phe Leu Phe Pro Pro Lys Pro Lys Asp
            260                 265                 270
Thr His His His His His His
        275

<210> SEQ ID NO 88
<211> LENGTH: 279
<212> TYPE: PRT
<213> ORGANISM: homosapiens

<400> SEQUENCE: 88

Met Glu Phe Gly Leu Ser Trp Val Phe Leu Val Ala Leu Leu Arg Gly
1               5                   10                  15
Val Gln Cys Gln Val Gln Leu Val Glu Ser Gly Gly Gly Leu Val Gln
            20                  25                  30
Pro Gly Arg Ser Leu Arg Leu Ser Cys Ala Val Ser Gly Phe Thr Phe
        35                  40                  45
Thr Ser Tyr Ala Met His Trp Val Arg Gln Ala Pro Gly Lys Gly Pro
    50                  55                  60
Glu Trp Val Ala Gly Ile Ser Lys Asp Gly Ser Asn Lys Arg His Ala
65                  70                  75                  80
Asp Ser Val Glu Gly Arg Phe Thr Ile Ser Arg Asp Asn Ser Lys Asn
                85                  90                  95
Thr Leu Tyr Leu Gln Leu Ser Gly Leu Arg Ala Glu Asp Thr Ala Val
            100                 105                 110
```

```
Tyr Tyr Cys Ala Arg Ser Gln Asp Pro Ser Asp Phe Asp Trp Leu Leu
            115                 120                 125

Ser Gln His Trp Gly Gln Gly Thr Leu Val Thr Val Ser Ser Ala Ser
        130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Ser
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
            260                 265                 270

His His His His His His
        275

<210> SEQ ID NO 89
<211> LENGTH: 276
<212> TYPE: PRT
<213> ORGANISM: homosapiens

<400> SEQUENCE: 89

Met Glu Phe Gly Leu Ser Trp Val Phe Leu Val Ala Ile Leu Lys Gly
1               5                   10                  15

Val Gln Cys Glu Met Gln Leu Val Glu Ser Gly Gly Gly Val Val Gln
            20                  25                  30

Pro Gly Gly Ser Leu Arg Leu Ser Cys Val Ala Ser Gly Phe Ser Phe
        35                  40                  45

Asp Asp Cys Val Met His Trp Val Arg Gln Val Pro Gly Lys Gly Leu
50                  55                  60

Glu Trp Val Ser Leu Ile Asn Gly Asn Gly Gly Thr Thr Lys Tyr Ala
65                  70                  75                  80

Asp Ser Val Lys Gly Arg Phe Thr Ile Ser Arg Asp Asn Ser Lys Asn
                85                  90                  95

Ser Leu Tyr Leu Glu Met Asn Asn Leu Arg Ile Glu Asp Thr Ala Leu
            100                 105                 110

Tyr Tyr Cys Gly Arg Gly Pro Arg Thr Thr Ala Trp Gln Asp Ser Phe
        115                 120                 125

Asn Val Trp Gly Gln Gly Thr Met Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205
```

```
Val Val Thr Val Pro Ser Ser Asn Phe Gly Thr Gln Thr Tyr Thr Cys
        210             215                 220
Asn Val Asp His Lys Pro Ser Asn Thr Lys Val Asp Lys Thr Val Glu
225             230                 235                 240
Arg Lys Cys Cys Val Glu Cys Pro Pro Cys Pro Ala Pro Pro Val Ala
            245                 250                 255
Gly Pro Ser Val Phe Leu Phe Pro Pro Lys Pro Lys Asp Thr His His
        260                 265                 270
His His His His
        275

<210> SEQ ID NO 90
<211> LENGTH: 278
<212> TYPE: PRT
<213> ORGANISM: homosapiens
<220> FEATURE:
<221> NAME/KEY: MISC_FEATURE
<222> LOCATION: (235)..(235)
<223> OTHER INFORMATION: Xaa is Asn or Lys.

<400> SEQUENCE: 90

Met Glu Phe Gly Leu Ser Trp Val Phe Leu Val Ala Leu Leu Arg Gly
1               5                   10                  15
Val Gln Cys Gln Gly Gln Leu Val Gln Ser Gly Gly Gly Val Val Gln
            20                  25                  30
Thr Gly Gly Ser Met Thr Leu Ser Cys Ala Ala Ser Gly Phe Thr Phe
        35                  40                  45
Ser Asn Tyr Gly Val His Trp Val Arg Gln Ala Pro Gly Lys Gly Leu
    50                  55                  60
Glu Trp Val Ala Gly Ile Ser Ser Asp Gly Ser Asn Arg Ile His Ala
65                  70                  75                  80
Asp Ser Leu Glu Gly Arg Phe Ala Ile Ser Arg Asp Asn Phe Glu Asn
            85                  90                  95
Thr Val Tyr Leu Gln Met Asn Ser Leu Arg Val Glu Asp Thr Ala Val
        100                 105                 110
Tyr Tyr Cys Val Arg Ser Gln Gln Pro Ser Phe Phe Asp Trp Leu Phe
    115                 120                 125
Ser Asp Tyr Trp Gly Gln Gly Thr Leu Val Ala Val Ser Ser Ala Ser
130                 135                 140
Thr Lys Gly Pro Ser Val Phe Pro Leu Ala Pro Cys Ser Arg Ser Thr
145                 150                 155                 160
Ser Glu Ser Thr Ala Ala Leu Gly Cys Leu Val Lys Asp Tyr Phe His
            165                 170                 175
Glu Pro Val Thr Val Ser Trp Asn Ser Gly Ala Leu Thr Ser Gly Val
        180                 185                 190
His Thr Phe Pro Ala Val Leu Gln Ser Ser Gly Leu Tyr Ser Leu Ser
    195                 200                 205
Ser Val Val Thr Val Pro Ser Ser Asn Phe Gly Thr Gln Thr Tyr Thr
        210                 215                 220
Cys Asn Val Asp His Lys Pro Ser Asn Thr Xaa Val Asp Lys Thr Val
225                 230                 235                 240
Glu Arg Lys Cys Cys Val Glu Cys Pro Pro Cys Pro Ala Pro Glu Leu
            245                 250                 255
Leu Gly Gly Pro Ser Val Phe Leu Phe Pro Pro Lys Pro Lys Asp Thr
        260                 265                 270
```

His His His His His His
        275

<210> SEQ ID NO 91
<211> LENGTH: 275
<212> TYPE: PRT
<213> ORGANISM: homosapiens

<400> SEQUENCE: 91

Met Glu Phe Gly Leu Ser Trp Ile Val Leu Ala Ala Ile Leu Lys Gly
1               5                   10                  15

Val Gln Cys Glu Val Gln Leu Val Glu Ser Gly Gly Gly Phe Val Lys
            20                  25                  30

Pro Gly Gly Ser Leu Arg Leu Ser Cys Ile Gly Ser Gly Phe Thr Phe
        35                  40                  45

Ser Asn Asn Gly Ile His Trp Val Arg Gln Ala Pro Gly Lys Gly Leu
    50                  55                  60

Glu Trp Val Ala Val Ile Ser Gly Asp Gly Ser Glu Glu His Tyr Ala
65                  70                  75                  80

Asp Ser Leu Lys Gly Arg Phe Thr Ile Ser Arg Asp Asn Ser Lys Asn
                85                  90                  95

Thr Val Phe Leu Gln Met Lys Ser Leu Arg His Glu Asp Thr Ala Met
            100                 105                 110

Tyr His Cys Val Arg Ser Gly Asp Arg Ile Gly Trp Tyr Asp Phe Asp
        115                 120                 125

His Trp Gly Leu Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Val Ala Gly
                245                 250                 255

Pro Ser Val Phe Leu Phe Pro Pro Lys Pro Lys Asp Thr His His His
            260                 265                 270

His His His
        275

<210> SEQ ID NO 92
<211> LENGTH: 278
<212> TYPE: PRT
<213> ORGANISM: homosapiens

<400> SEQUENCE: 92

Met Glu Phe Gly Leu Ser Trp Val Phe Leu Val Ala Ile Leu Glu Gly
1               5                   10                  15

Val Gln Cys Glu Val Gln Met Val Glu Ser Gly Gly Gly Leu Val Gln
            20                  25                  30

```
Pro Gly Gly Ser Leu Arg Leu Ser Cys Glu Ala Ser Gly Phe Thr Phe
            35                  40                  45

Ser Ser Tyr Trp Met Ser Trp Val Arg Gln Ala Pro Gly Lys Gly Leu
    50                  55                  60

Glu Trp Val Ala Asn Ile Lys Gln Asp Gly Ser Glu Lys Tyr Ser Val
65                  70                  75                  80

Asp Ser Val Lys Gly Arg Phe Thr Ile Ser Arg Asp Asn Ala Lys Lys
                85                  90                  95

Ser Leu Tyr Leu Gln Met Asn Ser Leu Arg Ala Glu Asp Thr Ala Val
                100                 105                 110

Tyr Tyr Cys Ala Arg Asp Gly Ser Gly Trp Pro Thr Gly Thr Ser Ser
            115                 120                 125

Tyr Phe Asp Tyr Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
            195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
                260                 265                 270

His His His His His His
            275

<210> SEQ ID NO 93
<211> LENGTH: 281
<212> TYPE: PRT
<213> ORGANISM: homosapiens

<400> SEQUENCE: 93

Met Glu Phe Gly Leu Ser Trp Leu Phe Leu Val Ala Ile Leu Lys Gly
1               5                   10                  15

Val Gln Cys Asp Met Arg Leu Ser Glu Thr Gly Gly Gly Arg Ile Gln
                20                  25                  30

Pro Gly Gly Ser Leu Arg Leu Ser Cys Ala Ala Ser Gly Phe Thr Phe
            35                  40                  45

Ser Asp Phe Ala Met Ala Trp Val Arg Gln Ala Pro Gly Lys Gly Leu
    50                  55                  60

Gln Trp Val Ser Asp Ile Ser Ala Thr Gly Gly Arg Ala His Thr Ala
65                  70                  75                  80

Asp Ser Val Arg Gly Arg Phe Thr Ile Ser Arg Asp Asn Ala Lys Asn
                85                  90                  95

Ile Leu Tyr Leu Gln Met Asp Ser Leu Arg Ala Glu Asp Thr Ala Thr
                100                 105                 110

Tyr Tyr Cys Ala Lys Asp Lys Gly Phe Cys Tyr Gly Asp Ser Cys Tyr
            115                 120                 125
```

```
Pro Ala Tyr Gly Leu Asp Val Trp Gly Pro Gly Thr Thr Val Thr Val
            130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Ala Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
    210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr His His His His His His
        275                 280

<210> SEQ ID NO 94
<211> LENGTH: 278
<212> TYPE: PRT
<213> ORGANISM: homosapiens

<400> SEQUENCE: 94

Met Glu Phe Gly Leu Ser Trp Ile Phe Leu Leu Ala Thr Leu Lys Gly
1               5                   10                  15

Val Gln Cys Glu Val Gln Leu Val Glu Ser Gly Gly Gly Leu Ala Gln
                20                  25                  30

Pro Gly Gly Ser Leu Arg Leu Ser Cys Ala Val Ser Gly Phe Asn Phe
            35                  40                  45

Gly Asp His Asp Met His Trp Val Arg Gln Pro Pro Gly Lys Gly Leu
50                  55                  60

Gln Trp Val Ala Ser Ile Ser Glu Asn Gly Tyr Thr Ile Lys Tyr Ser
65                  70                  75                  80

Asp Ser Val Lys Gly Arg Phe Thr Ile Ser Arg Asp Asn Ala Met Asn
                85                  90                  95

Ser Leu Tyr Leu His Leu Asn Ser Leu Arg Ser Glu Asp Thr Ala Ser
            100                 105                 110

Tyr Tyr Cys Ala Lys Ile Pro Tyr Gly Ser Glu Asn Phe Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
```

```
                210                 215                 220
Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
                260                 265                 270

His His His His His His
            275

<210> SEQ ID NO 95
<211> LENGTH: 277
<212> TYPE: PRT
<213> ORGANISM: homosapiens

<400> SEQUENCE: 95

Met Glu Phe Gly Leu Ser Trp Val Phe Leu Val Ala Ile Leu Glu Gly
1               5                   10                  15

Val Gln Cys Gln Val His Leu Val Glu Ser Gly Gly Gly Leu Val Gln
                20                  25                  30

Pro Gly Arg Ser Leu Arg Leu Ser Cys Ala Val Ser Gly Phe Thr Phe
            35                  40                  45

Ala Ser Tyr Ala Met His Trp Val Arg Gln Ala Pro Gly Lys Gly Leu
50                  55                  60

Glu Trp Val Ala Gly Ile Ser Lys Asp Gly Ser Asn Lys Arg His Ala
65                  70                  75                  80

Asp Ser Leu Glu Gly Arg Phe Thr Ile Ser Arg Asp Asn Ser Lys Asn
                85                  90                  95

Thr Leu Tyr Leu Gln Val Ser Gly Leu Arg Ala Glu Asp Thr Ala Val
            100                 105                 110

Tyr Tyr Cys Ala Arg Ser Gln Asp Pro Thr Asp Phe Asp Trp Leu Leu
        115                 120                 125

Ser Glu His Trp Gly Gln Gly Thr Leu Val Thr Val Ser Pro Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
            260                 265                 270

His His His His His
        275

<210> SEQ ID NO 96
<211> LENGTH: 277
```

```
<212> TYPE: PRT
<213> ORGANISM: homosapiens

<400> SEQUENCE: 96

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Asn Val Val Gln
            20                  25                  30

Pro Gly Arg Ser Leu Arg Leu Ser Cys Val Gly Ser Gly Phe Thr Phe
        35                  40                  45

Gly Asn Tyr Ala Ile His Trp Val Arg Gln Ala Pro Gly Lys Gly Pro
    50                  55                  60

Glu Trp Val Ala Gly Ile Ser Ser Ala Gly His Leu Lys Tyr Tyr Thr
65              70                  75                  80

Asp Ser Val Glu Gly Arg Phe Ser Ser Arg Asp Asn Ser Gln Asn
                85                  90                  95

Thr Val Tyr Leu Gln Leu Asn Ser Leu Arg Leu Glu Asp Thr Ala Met
            100                 105                 110

Tyr Tyr Cys Val Lys Ser Gln Gly Pro Thr Ala Phe Asp Trp Leu Phe
            115                 120                 125

Ser Gln Tyr Trp Gly Gln Gly Thr Pro Val Thr Val Ser Leu Ala Ser
        130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
            165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
        210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
            245                 250                 255

Ala Gly Pro Ser Val Phe Leu Phe Pro Pro Lys Pro Lys Asp Thr His
            260                 265                 270

His His His His His
        275

<210> SEQ ID NO 97
<211> LENGTH: 278
<212> TYPE: PRT
<213> ORGANISM: homosapiens

<400> SEQUENCE: 97

Met Glu Phe Gly Leu Ser Trp Leu Phe Leu Val Ala Ile Leu Lys Gly
1               5                   10                  15

Val Gln Ser Glu Val Gln Leu Leu Asp Ser Gly Gly Gly Leu Val Gln
            20                  25                  30

Pro Gly Gly Ser Leu Arg Leu Ser Cys Ser Ala Ser Gly Phe Thr Phe
        35                  40                  45

Arg Asn Tyr Ala Met Ala Trp Val Arg Gln Thr Pro Gly Gly Gly Leu
    50                  55                  60
```

```
Gln Trp Val Ser Thr Val Thr Gly Ser Gly Gly His Thr Val Tyr Ala
 65                  70                  75                  80

Asp Ser Val Lys Gly Arg Phe Thr Ile Ser Arg Asp Asn Ser Lys Asn
                 85                  90                  95

Thr Val Asp Leu Gln Met Asn Ser Leu Arg Val Asp Thr Ala Leu
            100                 105                 110

Tyr Tyr Cys Val Lys Phe Arg Gly Ala Cys Thr Asp Gly Arg Cys Tyr
            115                 120                 125

Trp Met Asp Val Trp Gly Gln Gly Thr Ala Val Thr Val Ser Ser Ala
130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
            195                 200                 205

Ser Ser Val Val Thr Val Pro Ser Ser Asn Phe Gly Thr Gln Thr Tyr
210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
                260                 265                 270

His His His His His His
            275

<210> SEQ ID NO 98
<211> LENGTH: 276
<212> TYPE: PRT
<213> ORGANISM: homosapiens

<400> SEQUENCE: 98

Met Glu Phe Gly Leu Ser Trp Val Phe Leu Val Ala Leu Leu Arg Gly
 1                   5                  10                  15

Val Gln Cys Gln Val Gln Leu Val Glu Ser Gly Gly Gly Val Val Gln
                 20                  25                  30

Pro Gly Lys Ser Leu Arg Leu Ser Cys Ala Ala Ser Gly Phe Thr Phe
            35                  40                  45

Ser Arg Tyr Ala Met His Trp Val Arg Gln Ala Pro Gly Lys Gly Leu
 50                  55                  60

Glu Trp Val Ala Leu Ile Ser Tyr Asp Gly Asp Asn Lys Tyr Tyr Ala
 65                  70                  75                  80

Asp Ser Val Lys Gly Arg Phe Thr Ile Ser Arg Asp Thr Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp His Ser Val Ser Thr Ile Glu Ser Pro Glu
            115                 120                 125

Gln Tyr Trp Gly His Gly Thr Glu Val Thr Val Ser Ser Ala Ser Thr
130                 135                 140

Lys Gly Pro Ser Val Phe Pro Leu Ala Pro Cys Ser Arg Ser Thr Ser
145                 150                 155                 160
```

```
Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr His His
            260                 265                 270

His His His His
        275

<210> SEQ ID NO 99
<211> LENGTH: 276
<212> TYPE: PRT
<213> ORGANISM: homosapiens

<400> SEQUENCE: 99

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Asp Phe Val Gln
                20                  25                  30

Pro Gly Gly Ser Leu Arg Leu Ser Cys Ala Val Ser Gly Phe Thr Phe
            35                  40                  45

Ser Asn Tyr Ala Met Asn Trp Val Arg Gln Ala Pro Gly Lys Gly Leu
    50                  55                  60

Glu Trp Val Ser Ser Ile Ile Asn Ser Gly Asp Asn Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Val Glu Asp Thr Ala Ile
            100                 105                 110

Tyr Tyr Cys Ala Lys Ala Ala Arg His Ser Leu Thr Thr Leu Arg Phe
        115                 120                 125

Asp Asn Trp Gly Gln Gly Thr Leu Val Thr Val Ser Ser Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
```

```
                    245                 250                 255
Gly Pro Ser Val Phe Leu Phe Pro Pro Lys Pro Lys Asp Thr His His
                260                 265                 270
His His His His
            275

<210> SEQ ID NO 100
<211> LENGTH: 277
<212> TYPE: PRT
<213> ORGANISM: homosapiens

<400> SEQUENCE: 100

Met Gly Phe Gly Leu Ser Trp Val Phe Leu Val Ala Leu Leu Arg Gly
1               5                   10                  15

Val Gln Cys Gln Val Leu Leu Val Glu Ser Gly Gly Gly Val Val Gln
            20                  25                  30

Pro Gly Arg Ser Leu Arg Leu Ser Cys Ala Ala Ser Gly Phe Ser Leu
        35                  40                  45

Ser Asn Arg Ala Met His Trp Val Arg Gln Ala Pro Gly Lys Gly Leu
    50                  55                  60

Glu Trp Val Ala Val Ile Ser Tyr Asp Gly Ser Glu Gln His Tyr Val
65                  70                  75                  80

Asp Ser Val Lys Gly Arg Phe Thr Ile Ser Ser Asp Thr Ser Lys Asn
                85                  90                  95

Thr Leu Tyr Leu Gln Met Asp Ser Leu Gly Val Glu Asp Thr Ala Val
            100                 105                 110

Tyr Tyr Cys Ala Arg Ala Asp Tyr Tyr Gly Ser Gly Ser Tyr Tyr Gln
        115                 120                 125

Met Asp Val Trp Gly Gln Gly Thr Thr Val Thr Val Ser Ser Thr Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
            260                 265                 270

His His His His His
        275

<210> SEQ ID NO 101
<211> LENGTH: 285
<212> TYPE: PRT
<213> ORGANISM: homosapiens

<400> SEQUENCE: 101

Met Glu Phe Gly Leu Ser Trp Val Phe Leu Val Ala Ile Ile Lys Gly
```

```
            1               5                   10                  15
            Val Gln Cys Gln Val Gln Leu Val Glu Ser Gly Gly Gly Leu Val Lys
                            20                  25                  30
            Pro Gly Gly Ser Leu Arg Leu Ser Cys Ala Ala Ser Gly Phe Ser Phe
                            35                  40                  45
            Ser Asp Asn Tyr Met Ser Trp Ile Arg Gln Ala Pro Gly Lys Gly Leu
                            50                  55                  60
            Glu Trp Leu Ser Tyr Ile Gly Thr Thr Val Ile Ala Ile Tyr Tyr Ala
            65                  70                  75                  80
            Glu Ser Val Lys Gly Arg Phe Thr Ile Ser Arg Asp Asn Ala Lys Arg
                            85                  90                  95
            Ser Leu Tyr Leu Gln Met Asn Ser Leu Arg Ala Asp Asp Thr Ala Val
                            100                 105                 110
            Tyr Tyr Cys Ala Arg Glu Gly Trp Gly Asp Tyr Gly Asp Tyr Tyr Gly
                            115                 120                 125
            Arg Ser Gly Val Phe Asp Ser Trp Gly Gln Gly Thr Leu Val Thr Val
                            130                 135                 140
            Ser Ser Ala Ser Thr Lys Gly Pro Ser Val Phe Pro Leu Ala Pro Ser
            145                 150                 155                 160
            Ser Lys Ser Thr Ser Gly Gly Thr Ala Ala Leu Gly Cys Leu Val Lys
                            165                 170                 175
            Asp Tyr Phe Pro Glu Pro Val Thr Val Ser Trp Asn Ser Gly Ala Leu
                            180                 185                 190
            Thr Ser Gly Val His Thr Phe Pro Ala Val Leu Gln Ser Ser Gly Leu
                            195                 200                 205
            Tyr Ser Leu Ser Ser Val Val Thr Val Pro Ser Ser Ser Leu Gly Thr
                            210                 215                 220
            Gln Thr Tyr Ile Cys Asn Val Asn His Lys Pro Ser Asn Thr Lys Val
            225                 230                 235                 240
            Asp Lys Lys Val Glu Pro Lys Ser Cys Asp Lys Thr His Thr Cys Pro
                            245                 250                 255
            Pro Cys Pro Ala Pro Glu Leu Leu Gly Gly Pro Ser Val Phe Leu Phe
                            260                 265                 270
            Pro Pro Lys Pro Lys Asp Thr His His His His His
                            275                 280                 285

<210> SEQ ID NO 102
<211> LENGTH: 273
<212> TYPE: PRT
<213> ORGANISM: homosapiens

<400> SEQUENCE: 102

Met Glu Phe Gly Leu Ser Trp Val Phe Leu Val Ala Leu Leu Arg Gly
            1               5                   10                  15
            Val Gln Cys Gln Val Gln Leu Val Glu Ser Gly Gly Gly Val Val Gln
                            20                  25                  30
            Pro Gly Gly Ser Leu Arg Leu Ser Cys Ala Ala Ser Gly Phe Thr Phe
                            35                  40                  45
            Ser Arg Ser Ser Met His Trp Val Arg Gln Ala Pro Gly Lys Gly Leu
                            50                  55                  60
            Glu Trp Val Ala Ile Ile Ser Ser Asp Gly Ser Lys Ile Tyr Tyr Ala
            65                  70                  75                  80
            Asp Ser Val Glu Gly Arg Phe Phe Ile Ser Arg Asp Asn Ser Arg Asn
                            85                  90                  95
```

```
Thr Leu Tyr Leu Gln Met Ser Ser Leu Arg Pro Glu Asp Thr Ala Leu
            100                 105                 110

Tyr His Cys Ala Lys Asp Trp Gln Trp Leu Val Asp Ser Trp Gly Gln
        115                 120                 125

Gly Thr Leu Val Ala Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr His His His His His His His
                260                 265                 270

His

<210> SEQ ID NO 103
<211> LENGTH: 274
<212> TYPE: PRT
<213> ORGANISM: homosapiens

<400> SEQUENCE: 103

Met Glu Phe Gly Leu Ser Trp Val Phe Leu Val Ala Ile Phe Gln Gly
1               5                   10                  15

Val Gln Cys Glu Val Gln Leu Val Glu Ser Gly Gly Gly Leu Val Gln
                20                  25                  30

Ala Gly Gly Ser Leu Arg Leu Ser Cys Val Gly Ser Gly Phe Ser Met
            35                  40                  45

Ser His Tyr Tyr Met Asp Trp Val Arg Gln Ala Pro Gly Lys Gly Leu
        50                  55                  60

Glu Trp Ile Gly Gln Thr Arg Lys Lys Asp Asn Ser Glu Ile Thr Glu
65                  70                  75                  80

Tyr Ala Ala Ser Val Lys Gly Arg Phe Thr Ile Ser Arg Asp Asp Ser
                85                  90                  95

Lys Asn Ser Val Tyr Leu Gln Met Asn Ser Leu Lys Thr Glu Asp Thr
            100                 105                 110

Ala Val Tyr Phe Cys Ala Ala Asp His Gly Ser Ser Gly Cys Leu Arg
        115                 120                 125

Trp Gly Arg Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190
```

```
Pro Ala Val Leu Gln Ser Ser Gly Leu Tyr Ser Leu Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Cys Pro Ala Pro Pro Val Ala Gly Pro
                245             250                 255

Ser Val Phe Leu Phe Pro Pro Lys Pro Lys Asp Thr Gln His His
            260                 265                 270

His His

<210> SEQ ID NO 104
<211> LENGTH: 276
<212> TYPE: PRT
<213> ORGANISM: homosapiens

<400> SEQUENCE: 104

Met Glu Phe Glu Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Phe Ala Met Gly Trp Val Arg Gln Ala Pro Gly Lys Gly Leu
    50                  55                  60

Glu Trp Val Ser Thr Ile His Gly Gly Asp Gly Pro Thr His Tyr Ala
65                  70                  75                  80

Glu Ser Val Arg Gly Arg Phe Ser Ile Ser Arg Asp Asn Ser Glu Asn
                85                  90                  95

Thr Leu Tyr Leu Gln Met Asp Ser Leu Arg Val Asp Asp Thr Ala Val
            100                 105                 110

Tyr His Cys Ala Lys Leu Glu Gly His Pro Leu Thr Glu Trp His Phe
        115                 120                 125

Asp Tyr Trp Gly Gln Gly Thr Pro Val Ile Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr His His
            260                 265                 270

His His His His
        275
```

<210> SEQ ID NO 105
<211> LENGTH: 281
<212> TYPE: PRT
<213> ORGANISM: homosapiens

<400> SEQUENCE: 105

Met Glu Phe Gly Leu Ser Trp Val Phe Leu Val Ala Leu Leu Arg Gly
1               5                   10                  15

Ile Gln Cys Gln Val Gln Leu Val Glu Ser Gly Gly Gly Leu Val Gln
            20                  25                  30

Pro Gly Arg Ser Leu Arg Leu Ser Cys Val Gly Ser Gly Phe Val Phe
        35                  40                  45

Thr Asn Tyr Asp Leu His Trp Val Arg Gln Ala Pro Gly Lys Gly Leu
    50                  55                  60

Glu Trp Leu Ala Val Thr Ser Ile Asp Gly Gly Leu Lys Phe Tyr Gly
65                  70                  75                  80

Asp Ser Val Ala Gly Arg Phe Thr Ile Ser Arg Asp Asn Ser Lys Ser
                85                  90                  95

Thr Leu Tyr Leu Asp Met Phe Ser Leu Lys Pro Glu Asp Thr Ala Val
            100                 105                 110

Tyr Tyr Cys Ala Arg Asp Gly Glu Leu Gly Thr Pro Asp Tyr Leu Asp
        115                 120                 125

His Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr His His His His His His His His
        275                 280

<210> SEQ ID NO 106
<211> LENGTH: 278
<212> TYPE: PRT
<213> ORGANISM: homosapiens

<400> SEQUENCE: 106

Met Glu Phe Gly Leu Ser Trp Val Leu Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Glu Ala Ser Gly Leu Met Phe
        35                  40                  45

```
Ser Ser Tyr Trp Val Thr Trp Val Arg Gln Ala Pro Gly Lys Gly Leu
    50                  55                  60

Glu Trp Val Ala Asn Ile Lys Glu Asp Gly Ser Glu Lys Tyr Tyr Leu
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Gly Val Asp Asp Thr Ala Leu
            100                 105                 110

Tyr Tyr Cys Ala Arg Gly Arg Tyr Lys Ser Gly Ile Asp Phe Asp Leu
            115                 120                 125

Trp Gly Gln Gly Thr Arg Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

His His His His His His
            275

<210> SEQ ID NO 107
<211> LENGTH: 281
<212> TYPE: PRT
<213> ORGANISM: homosapiens

<400> SEQUENCE: 107

Met Glu Phe Gly Leu Ser Trp Leu Phe Leu Val Ala Ile Leu Lys Gly
 1               5                  10                  15

Val Gln Cys Glu Val Gln Leu Leu Glu Ser Gly Gly Gly Leu Val Gln
                 20                  25                  30

Pro Gly Gly Ser Leu Arg Leu Ser Cys Ala Ala Ser Gly Phe Thr Phe
             35                  40                  45

Ser Arg Phe Ala Met Ser Trp Val Arg Gln Ala Pro Gly Lys Gly Leu
    50                  55                  60

Glu Trp Val Ser Gly Ile Ser Gly Ser Gly Gly Ser Thr Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Gly Asp Thr Ala Val
            100                 105                 110

Tyr Tyr Cys Ala Arg Ile Ser Gly Arg Gly Gly Phe Asp Ser Gly Asp
            115                 120                 125

Phe Glu Tyr Trp Gly Gln Gly Thr Leu Val Thr Val Ser Ser Ala Ser
130                 135                 140
```

```
Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Gln Thr Tyr Ile
210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr His His His His His His
            275                 280

<210> SEQ ID NO 108
<211> LENGTH: 280
<212> TYPE: PRT
<213> ORGANISM: homosapiens

<400> SEQUENCE: 108

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Ser Phe
        35                  40                  45

Ser Ile Tyr Asp Met His Trp Val Arg Gln Ala Pro Gly Lys Gly Leu
    50                  55                  60

Glu Trp Val Ala Val Ile Ser Tyr Asp Gly Asn Lys Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Ile Asp Ser Leu Arg Ala Glu Asp Met Ala Val
            100                 105                 110

Tyr Tyr Cys Ala Arg Asp Arg Thr Val Gly Phe Gly Val Val Val Ala
        115                 120                 125

Ala Arg Ala Phe Asp Ile Trp Gly Gln Gly Thr Met Val Thr Val Ser
130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Phe Leu Gln Ser Ser Gly Leu Tyr
        195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
```

```
225                 230                 235                 240
Lys Thr Val Glu Arg Lys Cys Cys Val Glu Cys Pro Pro Cys Pro Ala
                245                 250                 255
Pro Pro Val Ala Gly Pro Ser Val Phe Leu Phe Pro Pro Lys Pro Lys
                260                 265                 270
Asp Thr His His His His His His
                275                 280

<210> SEQ ID NO 109
<211> LENGTH: 277
<212> TYPE: PRT
<213> ORGANISM: homosapiens

<400> SEQUENCE: 109

Met Glu Phe Gly Leu Ser Trp Val Phe Leu Val Ala Leu Leu Arg Gly
1               5                   10                  15

Val Gln Cys Gln Val Leu Leu Val Gln Ser Gly Gly Gly Val Phe Gln
                20                  25                  30

Pro Gly Arg Ser Leu Arg Leu Ser Cys Ala Ala Ser Glu Phe Thr Phe
                35                  40                  45

Ser Asn Tyr Gly Val His Trp Val Arg Gln Ala Pro Gly Lys Gly Leu
    50                  55                  60

Glu Trp Val Ala Gly Ile Ser Ser Asp Gly Thr Asn Arg Ile His Ala
65                  70                  75                  80

Asp Ser Leu Glu Gly Arg Phe Ala Ile Ser Arg Asp Asn Ser Glu Asn
                85                  90                  95

Lys Val Tyr Leu Gln Met Asn Ser Leu Ile Val Gln Asp Thr Ala Val
                100                 105                 110

Tyr Tyr Cys Val Arg Ser Gln Gln Pro Ser Phe Phe Asp Trp Leu Phe
                115                 120                 125

Ser Asp Tyr Trp Gly Gln Gly Thr Leu Val Ala Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
                195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
                260                 265                 270

His His His His His
    275

<210> SEQ ID NO 110
<211> LENGTH: 285
<212> TYPE: PRT
<213> ORGANISM: homosapiens
```

```
<400> SEQUENCE: 110

Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Ser Phe
        35                  40                  45

Ser Asp Asn Tyr Met Ser Trp Ile Arg Gln Ala Pro Gly Lys Gly Leu
    50                  55                  60

Glu Trp Leu Ser Tyr Ile Gly Thr Thr Val Ser Ala Ile Tyr Tyr Ala
65                  70                  75                  80

Glu Ser Val Lys Gly Arg Phe Thr Ile Ser Arg Asp Asn Ala Lys Arg
                85                  90                  95

Ser Leu Tyr Leu Gln Met Asn Ser Leu Arg Ala Asp Thr Ala Val
            100                 105                 110

Tyr Tyr Cys Val Arg Glu Gly Trp Gly Asp Tyr Gly Asp Tyr Tyr Gly
        115                 120                 125

Arg Arg Gly Val Phe Asp Ser Trp Gly Gln Gly Thr Leu Val Thr Val
130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr His His His His His His
            275                 280                 285

<210> SEQ ID NO 111
<211> LENGTH: 269
<212> TYPE: PRT
<213> ORGANISM: homosapiens

<400> SEQUENCE: 111

Met Glu Phe Gly Leu Ser Trp Val Phe Leu Val Gly Leu Leu Arg Gly
1               5                   10                  15

Val Gln Cys Gln Val Gln Leu Val Glu Ser Gly Gly Asp Leu Val Gln
            20                  25                  30

Pro Gly Gly Ser Leu Arg Leu Ser Cys Ala Ala Ser Gly Phe Thr Phe
        35                  40                  45

Ser Ser Tyr Glu Met Asn Trp Phe Arg Gln Ala Pro Gly Arg Gly Leu
    50                  55                  60

Glu Trp Ile Ser Tyr Ile Ser Ser Gly Ile His Leu Asn Tyr Ala
65                  70                  75                  80
```

```
Asp Ser Val Arg Gly Arg Phe Thr Ile Ser Arg Asp Asp Ala Glu Tyr
            85                  90                  95

Ser Leu Tyr Leu Gln Met Asn Ser Leu Arg Ala Glu Asp Thr Gly Ile
        100                 105                 110

Tyr Tyr Cys Ala Thr Gly Asn Pro Val Pro His Trp Gly Gln Gly Thr
        115                 120                 125

Leu Val Thr Val Thr Ser Ala Ser Thr Lys Gly Pro Ser Val Phe Pro
        130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr His His His His His His
                260                 265

<210> SEQ ID NO 112
<211> LENGTH: 269
<212> TYPE: PRT
<213> ORGANISM: homosapiens

<400> SEQUENCE: 112

Met Glu Phe Gly Leu Ser Trp Leu Phe Leu Val Thr Ile Leu Lys Gly
1               5                   10                  15

Val Gln Cys Glu Val Gln Leu Leu Glu Ser Gly Gly Gly Ser Val Gln
            20                  25                  30

Pro Gly Gly Ser Leu Arg Leu Ser Cys Ala Thr Ser Gly Phe Thr Phe
        35                  40                  45

Thr Arg Gln Asp Met Asn Trp Val Arg Gln Ala Pro Gly Lys Gly Leu
    50                  55                  60

Glu Trp Val Ala Tyr Ile Thr Gly Ser Gly Asp Ala Thr Tyr Tyr Ala
65                  70                  75                  80

Asp Ser Val Arg Gly Arg Phe Thr Ile Ser Asp Ile Tyr Arg Asn
            85                  90                  95

Thr Leu Tyr Leu Gln Met Ser Ser Leu Arg Ala Glu Asp Thr Ala Ile
        100                 105                 110

Tyr Phe Cys Ala Arg Asn Ala Gly Leu Asp Tyr Trp Gly Gln Gly Thr
        115                 120                 125

Leu Val Thr Phe Ser Ser Ala Ser Thr Lys Gly Pro Ser Val Phe Pro
        130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190
```

```
Ser Ser Gly Leu Tyr Ser Leu Ser Ser Val Val Thr Val Pro Ser Ser
            195                 200                 205

Asn Phe Gly Thr Gln Thr Tyr Thr Cys Asn Val Asp His Lys Pro Ser
        210                 215                 220

Asn Thr Lys Val Asp Lys Thr Val Glu Arg Lys Cys Cys Val Glu Cys
225                 230                 235                 240

Pro Pro Cys Pro Ala Pro Val Ala Gly Pro Ser Val Phe Leu Phe
                245                 250                 255

Pro Pro Lys Pro Lys Asp Thr His His His His His His
            260                 265

<210> SEQ ID NO 113
<211> LENGTH: 280
<212> TYPE: PRT
<213> ORGANISM: homosapiens

<400> SEQUENCE: 113

Met Glu Phe Gly Leu Ser Trp Ala Phe Leu Val Ala Phe Leu Glu Gly
1               5                   10                  15

Val Gln Cys Glu Gly Gln Leu Val Glu Ser Gly Gly Gly Leu Ala Gln
            20                  25                  30

Pro Gly Gly Ser Leu Arg Leu Ser Cys Ala Ala Ser Gly Phe Thr Phe
        35                  40                  45

Ser Phe Tyr Glu Met Asn Trp Val Arg Gln Ala Pro Gly Lys Gly Leu
    50                  55                  60

Glu Trp Ile Ser Tyr Thr Trp Thr Ile Gly Thr Thr Met Tyr Tyr Ala
65                  70                  75                  80

Asp Ser Val Arg Gly Arg Phe Thr Val Ser Arg Asp Asn Thr Lys Asp
                85                  90                  95

Leu Leu Tyr Leu Gln Met Asn Ser Leu Arg Val Asp Asp Thr Ala Val
            100                 105                 110

Tyr Tyr Cys Ala Arg Gly Ser Leu Arg Gly Asn Glu Arg Gln Gly Val
        115                 120                 125

Trp Tyr Gly Met Asp Leu Trp Gly Arg Gly Thr Thr Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr His His His His His His
        275                 280
```

-continued

<210> SEQ ID NO 114
<211> LENGTH: 274
<212> TYPE: PRT
<213> ORGANISM: homosapiens

<400> SEQUENCE: 114

Met Glu Phe Gly Leu Ser Trp Val Phe Leu Val Ile Leu Glu Gly
1               5                   10                  15

Val Gln Cys Glu Val Gln Leu Val Glu Ser Gly Gly Leu Ala Gln
                20                  25                  30

Pro Gly Gly Ser Leu Arg Leu Ser Cys Ala Ala Ser Gly Phe Ser Val
            35                  40                  45

Ser Lys Tyr Glu Met Ser Trp Val Arg Gln Ala Pro Gly Lys Gly Leu
    50                  55                  60

Glu Trp Ile Ser Tyr Ile Ser His Arg Asp Gly Thr Thr Phe Tyr Ala
65                  70                  75                  80

Asp Ser Val Lys Gly Arg Phe Thr Ile Ser Arg Asp Ser Thr Lys Asn
                85                  90                  95

Ser Leu Ser Leu His Met Asn Ser Leu Arg Ile Asp Asp Thr Ala Ile
            100                 105                 110

Tyr Tyr Cys Met Arg Asp Gln Ser Asn Trp Gly Asp Cys Leu Asp Val
        115                 120                 125

Trp Gly Pro Gly Thr Thr Val Thr Val Ser Pro Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Val Ala Gly Pro
                245                 250                 255

Ser Val Phe Leu Phe Pro Pro Lys Pro Lys Asp Thr His His His His
            260                 265                 270

His His

<210> SEQ ID NO 115
<211> LENGTH: 275
<212> TYPE: PRT
<213> ORGANISM: homosapiens

<400> SEQUENCE: 115

Met Val Phe Gly Leu Ser Trp Val Phe Leu Val Thr Leu Leu Arg Gly
1               5                   10                  15

Val Gln Cys Leu Val Gln Val Val Glu Ser Gly Gly Gly Val Val Gln
                20                  25                  30

Pro Gly Arg Pro Leu Arg Leu Ser Cys Thr Ala Ser Gly Phe Thr Phe
            35                  40                  45

Ser Asp Tyr Pro Met His Trp Val Arg Gln Ala Ser Gly Lys Gly Leu
    50                  55                  60

Glu Trp Val Ala Val Ile Ser Lys Asp Gly Ser Asn Lys Tyr Ile Ala
65                  70                  75                  80

Asp Ser Val Lys Gly Arg Phe Thr Ile Ser Arg Glu Asn Phe Lys Asn
            85                  90                  95

Met Phe Tyr Leu His Met Asn Ser Leu Arg Pro Glu Asp Thr Ala Val
            100                 105                 110

Tyr Tyr Cys Ala Arg Pro Val Met Gly Ala Ser Gly Ser Tyr Tyr Ser
            115                 120                 125

Pro Trp Gly Gln Gly Thr Leu Val Thr Val Ser Ser Ala Ser Thr Lys
            130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Asn Phe Gly Thr Gln Thr Tyr Ser Cys Asn
            210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Val Ala Gly
            245                 250                 255

Pro Ser Val Phe Leu Phe Pro Pro Lys Pro Lys Val Thr His His
            260                 265                 270

His His His
        275

<210> SEQ ID NO 116
<211> LENGTH: 275
<212> TYPE: PRT
<213> ORGANISM: homosapiens

<400> SEQUENCE: 116

Met Glu Phe Gly Leu Ser Trp Ile Phe Leu Val Ala Ile Leu Lys Gly
1               5                   10                  15

Val His Ser Asp Val Gln Leu Leu Glu Ser Gly Gly Gly Leu Val Lys
            20                  25                  30

Pro Arg Gly Thr Leu Arg Leu Ser Cys Ala Ala Ser Gly Phe Thr Phe
            35                  40                  45

Thr Asn Thr Trp Met Ser Trp Val Arg Gln Ala Pro Gly Lys Gly Leu
            50                  55                  60

Glu Trp Leu Gly Arg Ile Lys Asn Lys Ile Asp Gly Gly Thr Ile Asp
65                  70                  75                  80

Tyr Ala Ala Pro Val Arg Gly Arg Phe Thr Ile Ser Arg Asp Asp Ser
            85                  90                  95

Leu Lys Thr Met Tyr Leu Glu Met Asn Asp Leu Glu Thr Glu Asp Thr
            100                 105                 110

Gly Ile Tyr Tyr Cys Val Thr Asp Asp Phe Arg Pro Leu Lys Asp Trp
            115                 120                 125

Gly Gln Gly Thr Leu Val Thr Val Ser Ser Ala Ser Thr Lys Gly Pro
            130                 135                 140

Ser Val Phe Pro Leu Ala Pro Cys Ser Arg Ser Thr Ser Glu Ser Thr

-continued

```
                145                 150                 155                 160
        Ala Ala Leu Gly Cys Leu Val Lys Asp Tyr Phe Pro Glu Pro Val Thr
                        165                 170                 175

Val Ser Trp Asn Ser Gly Ala Leu Thr Ser Gly Val His Thr Phe Pro
                        180                 185                 190

Ala Val Leu Gln Ser Ser Gly Leu Tyr Ser Leu Ser Ser Val Val Thr
                        195                 200                 205

Val Pro Ser Ser Asn Phe Gly Thr Gln Thr Tyr Thr Cys Asn Val Asp
                        210                 215                 220

His Lys Pro Ser Asn Thr Lys Val Asp Lys Thr Val Glu Arg Lys Cys
        225                 230                 235                 240

Cys Val Glu Cys Pro Pro Cys Pro Ala Pro Pro Val Ala Gly Pro Ser
                        245                 250                 255

Val Phe Leu Phe Pro Pro Lys Pro Lys Asp Thr His His His His
                        260                 265                 270

His Arg Val
                275

<210> SEQ ID NO 117
<211> LENGTH: 287
<212> TYPE: PRT
<213> ORGANISM: homosapiens

<400> SEQUENCE: 117

Met Glu Ser Gly Leu Ser Trp Val Phe Leu Ala Ala Leu Leu Arg Gly
        1               5                   10                  15

Val Gln Cys Gln Gly Gln Met Val Glu Ser Gly Gly Gly Val Val Gln
                        20                  25                  30

Pro Gly Lys Ser Leu Arg Leu Ser Cys Lys Val Ser Gly Phe Ala Leu
                        35                  40                  45

Asn Arg Tyr Ala Val His Trp Val Arg Gln Ala Pro Gly Lys Gly Leu
                        50                  55                  60

Glu Trp Val Ala Leu Ile Ser Tyr Asp Gly Asn Asn Gln Leu Tyr Ala
        65                  70                  75                  80

Glu Ser Val Lys Gly Arg Phe Thr Ile Ser Arg Gly Asn Ser Asp Asn
                        85                  90                  95

Thr Leu Tyr Leu His Met Lys Asn Leu Arg Val Asp Asp Thr Ala Val
                        100                 105                 110

Tyr Phe Cys Ala Arg Asp Val Ala Ser Val Ile Glu Gly Val Asp Tyr
                        115                 120                 125

Tyr Phe Tyr Gly Val Asp Val Trp Gly Gln Gly Thr Thr Val Ile Val
                        130                 135                 140

Ser Ser Ala Ser Thr Lys Gly Pro Ser Val Phe Pro Leu Ala Pro Ser
        145                 150                 155                 160

Ser Lys Ser Thr Ser Gly Gly Thr Ala Ala Leu Gly Cys Leu Val Lys
                        165                 170                 175

Asp Tyr Phe Pro Glu Pro Val Thr Val Ser Trp Asn Ser Gly Ala Leu
                        180                 185                 190

Thr Ser Gly Val His Thr Phe Pro Ala Val Leu Gln Ser Ser Gly Leu
                        195                 200                 205

Tyr Ser Leu Ser Ser Val Val Thr Val Pro Ser Ser Ser Leu Gly Thr
                        210                 215                 220

Gln Thr Tyr Ile Cys Asn Val Asn His Lys Pro Ser Asn Thr Lys Val
        225                 230                 235                 240
```

```
Asp Lys Lys Val Glu Pro Lys Ser Cys Asp Lys Thr His Thr Cys Pro
            245                 250                 255
Pro Cys Pro Ala Pro Glu Leu Leu Gly Gly Pro Ser Val Phe Leu Phe
        260                 265                 270
Pro Pro Lys Pro Lys Asp Thr His His His His His His His
        275                 280                 285
```

<210> SEQ ID NO 118
<211> LENGTH: 278
<212> TYPE: PRT
<213> ORGANISM: homosapiens

<400> SEQUENCE: 118

```
Met Glu Phe Gly Leu Ser Trp Val Phe Leu Val Ala Leu Leu Arg Gly
1               5                   10                  15
Val Gln Cys Gln Val Gln Leu Val Glu Ser Gly Gly Gly Val Val Gln
            20                  25                  30
Pro Gly Arg Ser Leu Arg Val Ser Cys Ala Ala Ser Gly Phe Thr Phe
        35                  40                  45
Ser Ser Phe Thr Met His Trp Val Arg Gln Ala Pro Gly Lys Gly Leu
    50                  55                  60
Glu Trp Val Ala Val Ile Leu Tyr Asn Gly Val Glu Lys Phe Tyr Ala
65                  70                  75                  80
Glu Ser Val Lys Gly Arg Phe Thr Val Ser Arg Asp Asn Ser Lys Asn
                85                  90                  95
Thr Leu Tyr Leu Glu Met Asp Ser Leu Lys Phe Asp Asp Thr Ala Ile
            100                 105                 110
Tyr Tyr Cys Thr Arg Glu Gly Ser Pro Ser His Gly Thr Ser Trp Tyr
        115                 120                 125
Gly Phe Glu Glu Trp Gly Gln Gly Thr Leu Val Thr Val Ser Ser Ala
    130                 135                 140
Ser Thr Lys Gly Pro Ser Val Phe Pro Leu Ala Pro Cys Ser Arg Ser
145                 150                 155                 160
Thr Ser Glu Ser Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Asn Phe Gly Thr Gln Thr Tyr
    210                 215                 220
Thr Cys Asn Val Asp His Lys Pro Ser Asn Thr Lys Val Asp Lys Thr
225                 230                 235                 240
Val Glu Arg Lys Cys Cys Val Glu Cys Pro Pro Cys Pro Ala Pro Pro
                245                 250                 255
Val Ala Gly Pro Ser Val Phe Leu Phe Pro Pro Lys Pro Lys Asp Thr
            260                 265                 270
His His His His His His
        275
```

<210> SEQ ID NO 119
<211> LENGTH: 278
<212> TYPE: PRT
<213> ORGANISM: homosapiens

<400> SEQUENCE: 119

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Lys
            20                  25                  30

Pro Gly Gly Ser Leu Thr Leu Ser Cys Ala Ala Ser Gly Phe Ser Phe
            35                  40                  45

Gly Asn Tyr Ala Met Asn Trp Val Arg Gln Ala Pro Gly Lys Gly Leu
            50                  55                  60

Glu Trp Val Ser Gly Ile Val Gly Ile Gly Ile Ser Lys Tyr Tyr Ala
65                  70                  75                  80

Asp Ser Val Lys Gly Arg Phe Thr Ile Ser Arg Asp Asn Leu Asn Asn
            85                  90                  95

Thr Leu Tyr Leu Glu Met Asn Ser Leu Arg Ala Glu Asp Thr Ala Val
            100                 105                 110

Tyr Tyr Cys Val Lys Val Cys Pro Arg Cys Gly Arg Glu Trp His Asp
            115                 120                 125

Ala Leu Asp Ile Trp Gly Gln Gly Thr Met Val Thr Val Ser Ser Ala
            130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
            165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Asn Phe Gly Thr Gln Thr Tyr
210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
            245                 250                 255

Val Ala Gly Pro Ser Val Phe Leu Phe Pro Pro Lys Pro Lys Asp Thr
            260                 265                 270

His His His His His His
            275

<210> SEQ ID NO 120
<211> LENGTH: 279
<212> TYPE: PRT
<213> ORGANISM: homosapiens

<400> SEQUENCE: 120

Met Glu Phe Gly Leu Ser Trp Val Val Leu Val Ala Phe Leu Lys Gly
1               5                   10                  15

Val Gln Cys Glu Val Leu Leu Val Glu Ser Gly Gly Gly Val Val Gln
            20                  25                  30

Pro Gly Gly Ser Leu Arg Leu Ser Cys Val Gly Ser Glu Phe Ser Phe
            35                  40                  45

Gly Asp Tyr Thr Met Asp Trp Val Arg Gln Val Pro Lys Gly Leu
            50                  55                  60

Glu Trp Val Ser Phe Ile Arg Ala Asp Pro Asp Thr Thr Tyr Gly
65                  70                  75                  80

Ser Pro Tyr Tyr Ala Ala Ser Val Arg Gly Arg Phe Ile Ile Ser Arg
            85                  90                  95

```
Asp Asn Thr Lys Asn Ser Leu Tyr Leu Gln Met Asn Ser Leu Thr Val
            100                 105                 110

Glu Asp Thr Ala Phe Tyr Tyr Cys Ala Arg Gly Ser Arg His Arg Trp
        115                 120                 125

Glu Val Leu Asp Leu Trp Gly Arg Gly Thr Leu Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr His His His His His His
        275

<210> SEQ ID NO 121
<211> LENGTH: 276
<212> TYPE: PRT
<213> ORGANISM: homosapiens

<400> SEQUENCE: 121

Met Asp Phe Gly Leu Ser Trp Val Phe Leu Val Ala Leu Leu Arg Gly
1               5                   10                  15

Ala Gln Cys Gln Val His Leu Val Glu Ser Gly Gly Ala Val Val Gln
            20                  25                  30

Pro Gly Thr Ser Leu Arg Leu Ser Cys Ala Ala Ser Gly Phe Thr Phe
        35                  40                  45

Ser Asn Tyr Val Met His Trp Val Arg Gln Ser Pro Gly Lys Gly Leu
    50                  55                  60

Glu Trp Val Gly Leu Ile Ser His Asp Gly Ser Asn Thr Tyr Tyr Arg
65                  70                  75                  80

Asp Ser Val Lys Gly Arg Phe Thr Ile Ser Arg Asp Asn Ser Gln Ser
                85                  90                  95

Val Ser Tyr Leu Gln Met Asn Ser Leu Arg Ala Glu Asp Thr Ala Val
            100                 105                 110

Phe Tyr Cys Ala Arg Glu Arg Leu Ser Met Tyr Thr Gly Tyr Gly Met
        115                 120                 125

Asp Val Trp Gly Gln Gly Thr Thr Val Thr Val Ser Pro Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
```

```
                        180                 185                 190
Thr Phe Pro Ala Val Leu Gln Ser Ser Gly Leu Tyr Ser Leu Ser Ser
            195                 200                 205

Val Val Thr Val Pro Ser Ser Asn Phe Gly Thr Gln Thr Tyr Thr Cys
            210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
            245                 250                 255

Gly Pro Ser Val Phe Leu Phe Pro Pro Lys Pro Lys Asp Thr Arg His
            260                 265                 270

His His His His
        275

<210> SEQ ID NO 122
<211> LENGTH: 277
<212> TYPE: PRT
<213> ORGANISM: homosapiens

<400> SEQUENCE: 122

Met Glu Phe Gly Leu Ser Trp Val Phe Leu Ala Ala Leu Leu Arg Gly
1               5                   10                  15

Val Gln Cys Gln Glu Gln Leu Met Glu Ser Gly Gly Gly Val Val Gln
            20                  25                  30

Pro Gly Arg Ser Leu Arg Leu Ser Cys Ala Ala Ser Gly Phe Ser Leu
            35                  40                  45

Ser Asp Tyr Ala Leu His Trp Ala Arg Gln Ala Pro Gly Lys Arg Pro
    50                  55                  60

Glu Ser Leu Ala Val Met Ser Tyr Asp Glu Thr Asn Thr Tyr Tyr Ala
65                  70                  75                  80

Asp Ser Val Arg Gly Arg Phe Thr Ile Ser Arg Asp Ser Ser Lys Asn
            85                  90                  95

Thr Leu Tyr Leu His Met Asn Ser Leu Thr Ser Glu Asp Thr Ala Val
            100                 105                 110

Tyr Tyr Cys Ala Arg Gly Gly Tyr His Asp Gly Thr Gly Tyr His Asp
            115                 120                 125

Thr Asp Phe Trp Gly Gln Gly Thr Leu Val Thr Val Ser Ser Ala Ser
130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
            165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
            195                 200                 205

Ser Val Val Thr Val Pro Ser Ser Asn Phe Gly Thr Gln Thr Tyr Thr
            210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
            245                 250                 255

Ala Gly Pro Ser Val Phe Leu Phe Pro Pro Lys Pro Lys Asp Thr His
            260                 265                 270
```

```
His His His His His
            275

<210> SEQ ID NO 123
<211> LENGTH: 285
<212> TYPE: PRT
<213> ORGANISM: homosapiens

<400> SEQUENCE: 123

Met Glu Phe Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Thr Ser Gly Phe Thr Phe
        35                  40                  45

Asp Ala Tyr Ala Ile His Trp Val Arg Gln Ala Pro Gly Lys Gly Leu
    50                  55                  60

Glu Trp Val Ser Gly Ile Ser Arg Ser Ser Thr His Ile Gly Tyr Ala
65                  70                  75                  80

Asp Ser Val Lys Gly Arg Phe Thr Ile Ser Arg Asp Asn Ala Lys Asn
                85                  90                  95

Ser Leu Phe Leu Gln Met Asn Ser Leu Arg Pro Glu Asp Thr Ala Leu
            100                 105                 110

Tyr Phe Cys Val Lys Asp Lys Glu Glu Asp Arg Ile Ala Ser Ala Arg
        115                 120                 125

Gly Gly Asp Tyr Gln Val Met Asp Val Trp Gly Gln Gly Thr Thr Val
    130                 135                 140

Thr Val Ser Ser Ala Ser Thr Lys Gly Pro Ser Val Phe Pro Leu Ala
145                 150                 155                 160

Pro Cys Ser Arg Ser Thr Ser Glu Ser Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Asn Phe
    210                 215                 220

Gly Thr Gln Thr Tyr Thr Cys Asn Val Asp His Lys Pro Ser Asn Thr
225                 230                 235                 240

Lys Val Asp Lys Thr Val Glu Arg Lys Cys Cys Val Glu Cys Pro Pro
                245                 250                 255

Cys Pro Ala Pro Pro Val Ala Gly Pro Ser Val Phe Leu Phe Pro Pro
            260                 265                 270

Lys Pro Lys Asp Thr His His His His His His
        275                 280                 285

<210> SEQ ID NO 124
<211> LENGTH: 277
<212> TYPE: PRT
<213> ORGANISM: homosapiens

<400> SEQUENCE: 124

Met Gln Phe Gly Leu Ser Trp Val Phe Leu Val Ala Leu Leu Arg Gly
1               5                   10                  15

Val Gln Cys Gln Val Gln Leu Val Glu Ser Glu Gly Gly Val Val Gln
            20                  25                  30
```

Pro Gly Arg Ser Leu Arg Leu Ser Cys Ala Ala Ser Gly Phe Ile Phe
        35                  40                  45

Ser Ser Tyr Ala Met His Trp Val Arg Gln Ala Pro Gly Lys Gly Leu
 50                  55                  60

Glu Trp Val Ala Val Ile Ser Phe Asp Gly Asn Asp Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Asp Thr Ala Val
            100                 105                 110

Tyr Tyr Cys Ala Arg Val Thr Thr Thr Ile Val Glu Val Lys Gly Asn
            115                 120                 125

Phe Asp Asn Trp Gly Pro Gly Thr Leu Val Ser Val Ser Ser Ala Ser
130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
            260                 265                 270

His His His His His
            275

<210> SEQ ID NO 125
<211> LENGTH: 275
<212> TYPE: PRT
<213> ORGANISM: homosapiens

<400> SEQUENCE: 125

Met Glu Phe Gly Leu Ser Trp Val Phe Leu Val Val Ile Leu Gln Gly
1               5                   10                  15

Val Gln Cys Glu Val Gln Leu Val Glu Ser Gly Gly Asp Leu Val Gln
                20                  25                  30

Ser Gly Gly Ser Leu Arg Leu Ser Cys Val Ala Ser Gly Phe Thr Phe
            35                  40                  45

Ser Asp Thr Tyr Met Asp Trp Val Arg Gln Ala Pro Gly Lys Gly Leu
 50                  55                  60

Glu Trp Val Ala Arg Val Arg Ser Lys Ala Ser Thr Tyr Ile Thr Glu
65                  70                  75                  80

Tyr Ala Ala Ser Val Lys Gly Arg Phe Thr Val Ser Arg Asp Asp Ser
                85                  90                  95

Lys Thr Ser Val Phe Leu Gln Met Asn Ser Leu Lys Gly Asp Asp Thr
            100                 105                 110

Ala Val Tyr Tyr Cys Val Lys Asp Tyr Leu Gly Thr Gly Asp Ser Trp
        115                 120                 125

```
Gly Gln Gly Thr Leu Val Thr Val Ser Ser Ala Ser Thr Lys Gly Pro
        130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr His His His His
            260                 265                 270

His His His
        275

<210> SEQ ID NO 126
<211> LENGTH: 277
<212> TYPE: PRT
<213> ORGANISM: homosapiens

<400> SEQUENCE: 126

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Pro Arg Leu Ser Cys Ala Ala Ser Gly Phe Thr Phe
            35                  40                  45

Ser Ser Tyr Asp Ile His Trp Val Arg Gln Ala Pro Gly Lys Gly Leu
    50                  55                  60

Glu Trp Val Ala Val Ile Trp Ser Asp Gly Ser Lys Thr Tyr Tyr Pro
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Gly Leu
            100                 105                 110

Tyr Tyr Cys Ala Arg Asp Arg Glu Ser Gly Gly Pro Thr Tyr Trp Tyr
        115                 120                 125

Phe Asp Leu Trp Gly Arg Gly Thr Leu Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
```

```
            210                 215                 220
Cys Asn Val Asn His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
                260                 265                 270

His His His His His
            275

<210> SEQ ID NO 127
<211> LENGTH: 281
<212> TYPE: PRT
<213> ORGANISM: homosapiens

<400> SEQUENCE: 127

Met Glu Phe Glu Leu Ser Trp Val Phe Leu Val Val Ile Leu Gln Gly
1               5                   10                  15

Val Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Phe Ala Phe
            35                  40                  45

Ser Asp Tyr Tyr Met Asp Trp Val Arg Gln Ala Pro Gly Lys Gly Leu
50                  55                  60

Gln Trp Val Gly Arg Ile Arg Arg Lys Ala Asn Asn Tyr Ser Thr Thr
65                  70                  75                  80

Tyr Ala Ala Ser Val Lys Gly Arg Phe Thr Ile Ser Arg Asp Asp Ser
                85                  90                  95

Lys Asp Ser Leu Tyr Leu Gln Met Asn Ser Leu Lys Thr Glu Asp Thr
            100                 105                 110

Ala Ile Tyr Tyr Cys Val Arg Val Asn Tyr Phe Asp Gly Ser Gly Tyr
        115                 120                 125

Ser Leu Asp Ala Phe Asp Val Trp Gly Gln Gly Thr Val Val Thr Val
130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr His His His His His His
        275                 280

<210> SEQ ID NO 128
<211> LENGTH: 275
```

```
<212> TYPE: PRT
<213> ORGANISM: homosapiens

<400> SEQUENCE: 128

Met Gly Phe Gly Leu Ser Trp Val Phe Leu Val Thr Leu Leu Arg Gly
1               5                   10                  15

Val Gln Cys Leu Val Gln Val Glu Ser Gly Gly Val Val Gln
            20                  25                  30

Pro Gly Arg Pro Leu Arg Leu Ser Cys Thr Ala Ser Gly Phe Thr Phe
        35                  40                  45

Ser Asp Tyr Pro Met His Trp Val Arg Gln Ala Ser Gly Lys Gly Leu
    50                  55                  60

Glu Trp Val Ala Val Ile Ser Lys Asp Gly Ser Asn Lys Tyr Ile Ala
65                  70                  75                  80

Asp Ser Val Lys Gly Arg Phe Thr Ile Ser Arg Glu Asn Phe Lys Asn
                85                  90                  95

Met Phe Tyr Leu His Met Asn Ser Leu Arg Pro Glu Asp Thr Ala Val
            100                 105                 110

Tyr Tyr Cys Ala Arg Pro Val Met Gly Ala Ser Gly Ser Tyr Tyr Ser
        115                 120                 125

Pro Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Ser Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Val Ala Gly
                245                 250                 255

Pro Ser Val Phe Leu Phe Pro Pro Lys Pro Lys Val Thr His His His
            260                 265                 270

His His His
        275

<210> SEQ ID NO 129
<211> LENGTH: 275
<212> TYPE: PRT
<213> ORGANISM: homosapiens

<400> SEQUENCE: 129

Met Glu Phe Gly Leu Ser Trp Val Phe Leu Val Ala Ile Leu Glu Gly
1               5                   10                  15

Val Gln Cys Glu Val Gln Leu Val Glu Ser Gly Gly Ile Leu Val Gln
            20                  25                  30

Pro Gly Gly Ser Leu Arg Leu Ser Cys Ala Ala Ser Gly Phe Thr Phe
        35                  40                  45

Ser Asp Tyr Trp Met Asn Trp Val Arg Gln Ala Pro Gly Lys Gly Leu
    50                  55                  60
```

```
Glu Trp Val Ala Asn Ile Asn Gln Gly Gly Val Glu Lys His Tyr Val
 65                  70                  75                  80

Asp Ser Val Arg Gly Arg Phe Thr Ile Ser Arg Asp Asn Ala Lys Asn
                 85                  90                  95

Ser Met Asp Leu Glu Met Asn Ser Leu Arg Asp Glu Asp Thr Ala Val
            100                 105                 110

Tyr Tyr Cys Val Arg Gly Pro Pro Gly Thr Asn Ala Gly Arg Leu Gly
            115                 120                 125

Pro Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Asn Phe Gly Thr Gln Thr Tyr Thr Cys Asn
210                 215                 220

Val Asp His Lys Pro Ser Asn Thr Lys Val Asp Lys Thr Val Glu Arg
225                 230                 235                 240

Lys Cys Tyr Val Glu Cys Pro Pro Cys Pro Ala Pro Pro Val Ala Gly
                245                 250                 255

Pro Ser Val Phe Leu Phe Pro Pro Lys Pro Lys Asp Thr His His His
            260                 265                 270

His His His
        275

<210> SEQ ID NO 130
<211> LENGTH: 233
<212> TYPE: PRT
<213> ORGANISM: homosapiens

<400> SEQUENCE: 130

Met Ser Trp Ile Arg Gln Ala Pro Gly Lys Gly Leu Glu Trp Leu Ser
 1               5                  10                  15

Tyr Ile Gly Thr Thr Val Ser Ala Ile Tyr Tyr Ala Glu Ser Val Lys
                20                  25                  30

Gly Arg Phe Thr Ile Ser Arg Asp Asn Ala Lys Arg Ser Leu Tyr Leu
            35                  40                  45

Gln Met Asn Ser Leu Arg Ala Asp Asp Thr Ala Val Tyr Tyr Cys Ala
 50                  55                  60

Arg Glu Gly Trp Gly Asp Tyr Gly Asp Tyr Tyr Gly Arg Arg Gly Val
 65                  70                  75                  80

Phe Asp Ser Trp Gly Gln Gly Thr Leu Val Thr Val Ser Ser Ala Ser
                85                  90                  95

Thr Lys Gly Pro Ser Val Phe Pro Leu Ala Pro Ser Ser Lys Ser Thr
            100                 105                 110

Ser Gly Gly Thr Ala Ala Leu Gly Cys Leu Val Lys Asp Tyr Phe Pro
            115                 120                 125

Glu Pro Val Thr Val Ser Trp Asn Ser Gly Ala Leu Thr Ser Gly Val
130                 135                 140

His Thr Phe Pro Ala Val Leu Gln Ser Ser Gly Leu Tyr Ser Leu Ser
145                 150                 155                 160
```

```
Ser Val Val Thr Val Pro Ser Ser Leu Gly Thr Gln Thr Tyr Ile
                165                 170                 175

Cys Asn Val Asn His Lys Pro Ser Asn Thr Lys Val Asp Lys Val
                180                 185                 190

Glu Pro Lys Ser Cys Asp Lys Thr His Thr Cys Pro Pro Cys Pro Ala
        195                 200                 205

Pro Glu Leu Leu Gly Gly Pro Ser Val Phe Leu Phe Pro Pro Lys Pro
    210                 215                 220

Lys Asp Ala His His His His His His
225                 230
```

<210> SEQ ID NO 131
<211> LENGTH: 274
<212> TYPE: PRT
<213> ORGANISM: homosapiens

<400> SEQUENCE: 131

```
Met Glu Phe Gly Leu Ser Trp Val Phe Leu Val Ala Val Leu Arg Gly
1               5                   10                  15

Val Gln Cys Gln Val His Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Ala Met Ala Trp Ile Arg Gln Ser Pro Gly Lys Gly Leu
        50                  55                  60

Glu Trp Val Ser Ala Ile Thr Gly Asn Gly Gly Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Asp Asp Thr Ala Val
                100                 105                 110

Tyr Phe Cys Ala Lys Ala Leu Arg Pro Ser Gly Gly Pro Arg Asp Tyr
            115                 120                 125

Trp Gly Gln Gly Thr Leu Val Thr Val Ser Ser Ala Ser Thr Lys Gly
        130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Val Ala Gly Pro
                245                 250                 255

Ser Val Phe Leu Phe Pro Pro Lys Pro Lys Asp Thr His His His His
            260                 265                 270

His His
```

<210> SEQ ID NO 132

<211> LENGTH: 276
<212> TYPE: PRT
<213> ORGANISM: homosapiens

<400> SEQUENCE: 132

Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Ser Tyr
        35                  40                  45

Ser Asp His Tyr Met Tyr Trp Ile Arg Gln Ala Pro Gly Lys Gly Leu
    50                  55                  60

Glu Trp Ile Ser Tyr Ile Ser Arg Ser Gly Ser Pro Ile Asn Tyr Ala
65                  70                  75                  80

Asp Ser Val Lys Gly Arg Phe Thr Ile Ser Arg Asp Asn Ala Arg Lys
                85                  90                  95

Ser Leu Tyr Leu Gln Met Asn Ser Leu Arg Val Glu Asp Thr Ala Val
            100                 105                 110

Tyr Tyr Cys Ala Arg Leu Gly Gln Tyr Tyr Asp Gly Ser Val Glu Leu
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr His His
            260                 265                 270

His His His His
        275

<210> SEQ ID NO 133
<211> LENGTH: 285
<212> TYPE: PRT
<213> ORGANISM: homosapiens

<400> SEQUENCE: 133

Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Ser Phe
        35                  40                  45

Ser Asp Asn Tyr Met Ser Trp Ile Arg Gln Ala Pro Gly Lys Gly Leu
    50                  55                  60

```
Glu Trp Leu Ser Tyr Ile Gly Thr Thr Val Ser Ala Ile Tyr Tyr Ala
 65                  70                  75                  80

Glu Ser Val Lys Gly Arg Phe Thr Ile Ser Arg Asp Asn Ala Lys Arg
                 85                  90                  95

Ser Leu Tyr Leu Gln Met Asn Ser Leu Arg Ala Asp Asp Thr Ala Val
            100                 105                 110

Tyr Tyr Cys Ala Arg Glu Gly Trp Gly Asp Tyr Gly Asp Tyr Tyr Gly
            115                 120                 125

Arg Arg Gly Val Phe Asp Ser Trp Gly Gln Gly Thr Leu Val Thr Val
        130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Leu Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Leu Gly Thr
210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr His His His His His His
        275                 280                 285

<210> SEQ ID NO 134
<211> LENGTH: 279
<212> TYPE: PRT
<213> ORGANISM: homosapiens

<400> SEQUENCE: 134

Met Glu Phe Gly Leu Ser Trp Leu Phe Leu Val Ala Thr Leu Lys Gly
1               5                   10                  15

Val Gln Cys Glu Val Gln Leu Leu Glu Ser Gly Gly Asp Leu Val Gln
                20                  25                  30

Pro Gly Gly Ser Leu Arg Leu Ser Cys Ala Ala Ser Gly Phe Thr Phe
            35                  40                  45

Asn Asn Tyr Ala Met Val Trp Val Arg Gln Ala Pro Gly Lys Arg Leu
        50                  55                  60

Glu Leu Val Ser Ile Ile Thr Gly Asp Gly Ile Asn Thr Tyr Tyr Pro
65                  70                  75                  80

Gly Ser Val Arg Asp Arg Phe Thr Ile Ser Arg Asp Asn Ser His Asn
                85                  90                  95

Thr Leu Tyr Leu Gln Met Ser Ser Leu Arg Ala Glu Asp Ser Ala Ile
            100                 105                 110

Tyr Phe Cys Ala Arg Gly Thr Leu Gly Ser Cys Ser Gly Pro Arg Cys
            115                 120                 125

Tyr Pro Leu Asp Ser Trp Gly Gln Gly Thr Leu Val Thr Val Ser Ser
        130                 135                 140

Ala Ser Thr Lys Gly Pro Ser Val Phe Pro Leu Ala Pro Cys Ser Arg
```

```
                145                 150                 155                 160
        Ser Thr Ser Glu Ser Thr Ala Ala Leu Gly Cys Leu Val Lys Asp Tyr
                        165                 170                 175

Phe Pro Glu Pro Val Thr Val Ser Trp Asn Ser Gly Ala Leu Thr Ser
                        180                 185                 190

Gly Val His Thr Phe Pro Ala Val Leu Gln Ser Ser Gly Leu Tyr Ser
                        195                 200                 205

Leu Ser Ser Val Val Thr Val Pro Ser Ser Asn Phe Gly Thr Gln Thr
                210                 215                 220

Tyr Thr Cys Asn Val Asp His Lys Pro Ser Asn Thr Lys Val Asp Lys
        225                 230                 235                 240

Thr Val Glu Arg Lys Cys Cys Val Glu Cys Pro Pro Cys Pro Glu Pro
                        245                 250                 255

Pro Val Ala Gly Pro Ser Val Phe Leu Phe Pro Pro Asn Pro Lys Asp
                        260                 265                 270

Thr Asp His His His His His
                        275

<210> SEQ ID NO 135
<211> LENGTH: 271
<212> TYPE: PRT
<213> ORGANISM: homosapiens

<400> SEQUENCE: 135

Met Glu Phe Gly Leu Ser Trp Ile Leu Leu Val Ala Ile Leu Lys Gly
        1               5                   10                  15

Val Gln Cys Glu Val Gln Leu Val Glu Ser Gly Gly Gly Leu Val Lys
                        20                  25                  30

Pro Gly Glu Ser Leu Arg Leu Ser Cys Ala Ala Ser Gly Phe Ser Val
                        35                  40                  45

Gly Asp Val Trp Met Ser Trp Val Arg Gln Ala Pro Gly Lys Gly Leu
                    50                  55                  60

Glu Trp Val Gly Arg Ile His Ser Lys Ala Asp Ala Gly Thr Ile Asp
        65                  70                  75                  80

Tyr Asn Thr Pro Val Lys Gly Arg Phe Thr Met Ser Arg Asp Asp Ser
                        85                  90                  95

Thr Asn Thr Leu Tyr Leu Gln Met Asn Ser Leu Lys Ser Glu Asp Thr
                        100                 105                 110

Gly Val Tyr Tyr Cys Thr Arg Arg Ser Ser Met Gly Gly Gln Gly Thr
                        115                 120                 125

Leu Val Thr Val Ser Ser Ala Ser Thr Lys Gly Pro Ser Val Phe Pro
                130                 135                 140

Leu Ala Pro Cys Ser Arg Ser Thr Ser Glu Ser Thr Ala Ala Leu Gly
        145                 150                 155                 160

Cys Leu Val Lys Asp Tyr Phe Pro Glu Pro Val Thr Val Ser Trp Asn
                        165                 170                 175

Ser Gly Ala Leu Thr Ser Gly Val His Thr Phe Pro Ala Val Leu Gln
                        180                 185                 190

Ser Ser Gly Leu Tyr Ser Leu Ser Ser Val Val Thr Val Pro Ser Ser
                        195                 200                 205

Asn Phe Gly Thr Gln Thr Tyr Thr Cys Asn Val Asp His Lys Pro Ser
                        210                 215                 220

Asn Thr Lys Val Asp Lys Thr Val Glu Arg Lys Cys Cys Val Glu Cys
        225                 230                 235                 240
```

```
Pro Pro Cys Pro Ala Pro Val Ala Gly Pro Ser Val Phe Leu Phe
                245                 250                 255

Pro Pro Lys Pro Lys Asp Pro His His His His His His His His
            260                 265                 270

<210> SEQ ID NO 136
<211> LENGTH: 280
<212> TYPE: PRT
<213> ORGANISM: homosapiens

<400> SEQUENCE: 136

Met Glu Phe Gly Leu Ser Trp Val Phe Leu Val Ala Ile Leu Glu Gly
1               5                   10                  15

Val Gln Cys Glu Ala Gln Leu Val Glu Ser Gly Gly Gly Leu Val His
            20                  25                  30

Pro Gly Gly Ser Leu Arg Leu Ser Cys Ala Thr Ser Gly Phe Thr Phe
        35                  40                  45

Arg Ser Tyr Glu Met Asn Trp Val Arg Gln Ala Pro Gly Lys Gly Pro
    50                  55                  60

Glu Trp Val Ser Tyr Ile Ser Arg Ser Ala Thr Thr Ile Tyr Tyr Ala
65                  70                  75                  80

Asp Ser Val Lys Gly Arg Phe Thr Ile Ser Arg Asp Asp Ala His His
                85                  90                  95

Ser Leu His Leu Gln Met Asp Ser Leu Arg Val Glu Asp Thr Ala Val
            100                 105                 110

Tyr Tyr Cys Ala Arg Gly Ser Ser Ile Val Glu Asp Pro Gly Trp Phe
        115                 120                 125

Asp Pro Trp Gly Gln Gly Thr Leu Val Ile Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Ile Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr His His His His His His
        275                 280

<210> SEQ ID NO 137
<211> LENGTH: 281
<212> TYPE: PRT
<213> ORGANISM: homosapiens

<400> SEQUENCE: 137

Met Lys Phe Gly Leu Ser Trp Val Phe Leu Val Ala Ile Leu Glu Gly
1               5                   10                  15
```

Val His Cys Glu Val Gln Leu Ala Gln Ser Gly Gly Gly Leu Val Gln
              20                  25                  30

Pro Gly Gly Ser Leu Arg Leu Ser Cys Ala Ala Ser Gly Phe Thr Phe
          35                  40                  45

Arg Ser Tyr Trp Met Asn Trp Val Arg Gln Ala Pro Gly Lys Gly Leu
    50                  55                  60

Glu Trp Val Ala Asn Ile Lys Glu Asp Gly Ser Glu Thr His Tyr Val
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Thr Glu Asp Thr Ala Leu
            100                 105                 110

Tyr Tyr Cys Ala Arg Ile Gln Thr Asn Ser Trp Ser Tyr Tyr Gln Tyr
        115                 120                 125

Tyr Gly Leu Asp Val Trp Gly Gln Gly Thr Thr Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr His His His His His His His
        275                 280

<210> SEQ ID NO 138
<211> LENGTH: 274
<212> TYPE: PRT
<213> ORGANISM: homosapiens

<400> SEQUENCE: 138

Met Glu Phe Gly Leu Ser Trp Val Phe Leu Val Val Ile Leu Gln Gly
1               5                   10                  15

Val Gln Cys Glu Asp Gln Leu Val Glu Ser Gly Gly Gly Leu Val Gln
              20                  25                  30

Pro Gly Gly Ser Leu Arg Leu Ser Cys Ala Ala Ser Gly Phe Ile Phe
          35                  40                  45

Ser Asp His His Met Asp Trp Val Arg Gln Ala Pro Gly Lys Gly Leu
    50                  55                  60

Glu Cys Val Ala Arg Ser Lys Arg Ala Gly Asp Arg Tyr Ile Pro Glu
65                  70                  75                  80

Tyr Ala Ala Ser Ala Glu Gly Arg Phe Thr Ile Ser Arg Asp Asp Ser
                85                  90                  95

Lys Asn Ser Leu Tyr Leu Gln Met Asn Asn Leu Gln Thr Glu Asp Thr
            100                 105                 110

Ala Val Tyr Tyr Cys Thr Arg Asp Ser Met Lys Tyr Ala Phe Asp Leu
            115                 120                 125

Trp Gly Gln Gly Thr Lys Val Thr Val Ser Ser Ala Ser Thr Lys Gly
        130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr His His His His
            260                 265                 270

His His

<210> SEQ ID NO 139
<211> LENGTH: 278
<212> TYPE: PRT
<213> ORGANISM: homosapiens

<400> SEQUENCE: 139

Met Val Phe Gly Leu Ser Trp Leu Phe Leu Val Ala Ile Leu Lys Gly
1               5                   10                  15

Val Gln Cys Glu Val Leu Leu Leu Glu Ser Gly Gly Gly Leu Val Gln
            20                  25                  30

Pro Gly Gly Ser Leu Arg Leu Ser Cys Ala Ala Ser Gly Phe Met Phe
        35                  40                  45

Gly Ser Tyr Ala Met Ser Trp Val Arg Gln Ala Pro Gly Lys Gly Leu
    50                  55                  60

Glu Trp Val Ser Ala Leu Ser Gly Gly Gly Ala Thr Thr His Tyr Ala
65                  70                  75                  80

Ala Ser Val Lys Gly Arg Phe Thr Ile Ser Arg Asp Asn Ser Asn Asn
                85                  90                  95

Thr Leu Phe Leu Gln Met Asn Ser Leu Arg Ala Glu Asp Thr Ala Val
            100                 105                 110

Tyr Tyr Cys Ala Lys Ser Gly Arg Leu Trp Phe Gly Glu Leu Phe Asp
        115                 120                 125

Trp Phe Asp Pro Trp Gly Gln Gly Thr Leu Val Ile Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

```
Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

His His His His His His
            275

<210> SEQ ID NO 140
<211> LENGTH: 277
<212> TYPE: PRT
<213> ORGANISM: homosapiens

<400> SEQUENCE: 140

Met Asp Phe Gly Leu Ser Trp Val Phe Leu Val Ala Leu Leu Arg Gly
1               5                   10                  15

Val Gln Cys Gln Val Leu Leu Val Glu Ser Gly Gly Gly Val Val Gln
                20                  25                  30

Pro Gly Arg Ser Leu Arg Leu Ser Cys Ala Ala Ser Gly Phe Ser Leu
            35                  40                  45

Ser Asn Arg Ala Met His Trp Val Arg Gln Ala Pro Gly Lys Gly Leu
        50                  55                  60

Glu Trp Val Ala Val Ile Ser Tyr Asp Gly Ser Glu Gln His Tyr Val
65                  70                  75                  80

Asp Ser Val Lys Gly Arg Phe Thr Ile Ser Ser Asp Thr Ser Lys Asn
                85                  90                  95

Thr Leu Tyr Leu Gln Met Asp Ser Leu Gly Val Glu Asp Thr Ala Val
            100                 105                 110

Tyr Tyr Cys Ala Arg Ala Asp Tyr Tyr Gly Ser Gly Ser Tyr Tyr Gln
        115                 120                 125

Met Asp Val Trp Gly Gln Gly Thr Thr Val Thr Val Ser Ser Thr Ser
130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
            260                 265                 270

His His His His His
        275
```

<210> SEQ ID NO 141
<211> LENGTH: 274
<212> TYPE: PRT
<213> ORGANISM: homosapiens

<400> SEQUENCE: 141

Met Glu Leu Gly Leu Ser Trp Ile Ser Leu Ala Ile Leu Lys Gly
1               5                   10                  15

Val Gln Cys Glu Val Gln Leu Val Glu Ser Gly Gly Ala Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Val Pro Gly Lys Gly Leu
    50                  55                  60

Glu Trp Val Ala Gly Ile Ser Leu Asn Ser Gly Lys Met Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Pro Glu Asp Thr Ala Leu
            100                 105                 110

Tyr Tyr Cys Ala Lys Asp Lys Gly Gly Arg Tyr Gly Ser Gly Thr
        115                 120                 125

Tyr Tyr Ala Glu Tyr Phe Gln His Trp Gly Gln Gly Thr Leu Val Ile
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Asn Phe Gly
    210                 215                 220

Thr Gln Thr Tyr Thr Cys Asn Val Asp His Lys Pro Ser Asn Thr Lys
225                 230                 235                 240

Val Asp Lys Thr Val Glu Arg Lys Cys Cys Val Glu Cys Pro Pro Cys
                245                 250                 255

Pro Ala Pro Pro Val Ala Gly Pro Ser Val Phe Leu Phe Pro Pro Lys
            260                 265                 270

Pro Lys

<210> SEQ ID NO 142
<211> LENGTH: 271
<212> TYPE: PRT
<213> ORGANISM: homosapiens

<400> SEQUENCE: 142

Met Glu Phe Gly Leu Ser Trp Val Leu Leu Val Ala Ile Leu Lys Gly
1               5                   10                  15

Val Gln Cys Glu Val Gln Leu Val Glu Ser Gly Gly Thr Leu Val Gln
            20                  25                  30

Pro Gly Arg Ser Leu Arg Leu Ser Cys Thr Val Tyr Glu Phe Pro Phe
        35                  40                  45

Gly Asp Tyr Thr Met Ser Trp Val Arg Gln Ala Pro Gly Lys Gly Leu
    50                  55                  60

Glu Trp Ile Ser Gly Leu Ser Arg Ser Asp Ile Ala Tyr Ala Asp Ser
65                  70                  75                  80

Val Lys Gly Arg Phe Thr Val Ser Arg Asp Asn Thr Lys Asn Ser Val
                85                  90                  95

His Leu Glu Met Thr Ser Leu Thr Thr Asp Asp Thr Val Tyr Tyr
                100                 105                 110

Cys Ala Lys Gly Glu Ala Ile Gln Leu Pro Phe Gln Tyr Trp Gly Gln
            115                 120                 125

Gly Thr Leu Val Thr Val Ser Ser Ala Ser Thr Lys Gly Pro Ser Val
        130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
            195                 200                 205

Ser Ser Asn Phe Gly Thr Gln Thr Tyr Thr Cys Asn Val Asp His Lys
        210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr His His His His His His
                260                 265                 270

<210> SEQ ID NO 143
<211> LENGTH: 275
<212> TYPE: PRT
<213> ORGANISM: homosapiens

<400> SEQUENCE: 143

Met Glu Phe Gly Leu Ser Trp Val Phe Leu Ile Ala Ile Ile Lys Gly
1               5                   10                  15

Val Gln Cys Gln Val Gln Leu Val Gln Ser Gly Gly Gly Leu Val Arg
            20                  25                  30

Pro Gly Gly Ser Leu Arg Leu Ala Cys Ala Thr Ser Gly Phe Thr Phe
        35                  40                  45

Asp Ala His Tyr Met Ser Trp Ile Arg Gln Ala Pro Gly Lys Gly Leu
    50                  55                  60

Glu Trp Ile Ser Tyr Ile Asn Pro Ser Gly Ser Thr Ile Tyr Tyr Glu
65                  70                  75                  80

Asp Ser Val Arg Gly Arg Phe Thr Val Ser Arg Asp Asn Pro Gln Ser
                85                  90                  95

Ser Leu Ser Leu Gln Met Ser Ser Leu Arg Ala Glu Thr Ala Val
                100                 105                 110

Tyr Tyr Cys Ala Arg Asp Arg Gly Gly Ser Gly Ser Tyr Ile Phe Asp
            115                 120                 125

His Trp Gly Gln Gly Val Leu Val Thr Val Ser Ser Ala Ser Thr Lys
        130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro

```
                     165                 170                 175
Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Asn Phe Gly Thr Gln Thr Tyr Thr Cys Asn
        210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr His His His
            260                 265                 270

His His His
        275

<210> SEQ ID NO 144
<211> LENGTH: 280
<212> TYPE: PRT
<213> ORGANISM: homosapiens

<400> SEQUENCE: 144

Met Glu Phe Gly Leu Ser Trp Ile Phe Leu Leu Ala Ile Leu Lys Gly
1               5                   10                  15

Val Gln Cys Glu Val Gln Leu Val Glu Ser Gly Gly Asp Leu Val Gln
            20                  25                  30

Pro Gly Arg Ser Leu Arg Leu Ser Cys Thr Ala Ser Gly Phe Thr Phe
        35                  40                  45

Asp Asn Tyr Ala Met His Trp Val Arg Gln Ala Pro Gly Lys Gly Leu
    50                  55                  60

Glu Trp Val Ser Gly Ile Ser Trp Asn Ser Gly Asp Ile Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Val Ala Asp Thr Ala Leu
            100                 105                 110

Tyr Tyr Cys Ala Lys Asp Gly Ile Pro Val Arg Tyr Gly Ser Thr Trp
        115                 120                 125

Tyr Asn Trp Phe Asp Ser Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255
```

```
Pro Pro Val Ala Gly Pro Ser Val Phe Leu Phe Pro Pro Lys
            260                 265                 270

Asp Thr His His His His His His
            275                 280
```

<210> SEQ ID NO 145
<211> LENGTH: 273
<212> TYPE: PRT
<213> ORGANISM: homosapiens

<400> SEQUENCE: 145

```
Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Ser His Tyr Trp Met His Trp Val Arg Gln Leu Pro Gly Gln Ser Pro
    50                  55                  60

Val Trp Val Ala Arg Thr Asn Pro Asp Gly Ser Tyr Leu Ser Tyr Ala
65                  70                  75                  80

Asp Ala Val Lys Gly Arg Phe Thr Ile Ser Arg Asp Asn Ala Lys Asn
                85                  90                  95

Thr Leu Phe Leu Gln Met Asn Ser Leu Ser Pro Glu Asp Thr Ala Val
            100                 105                 110

Tyr Tyr Cys Val Arg Asp Met Ser Gly Gly Trp Phe Thr Asp Cys Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Thr Lys Pro Lys Asp Thr His His His His
            260                 265                 270

His
```

<210> SEQ ID NO 146
<211> LENGTH: 271
<212> TYPE: PRT
<213> ORGANISM: homosapiens

<400> SEQUENCE: 146

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
```

```
            20                  25                  30
Pro Gly Gly Ser Leu Arg Leu Ser Cys Ala Ala Ser Gly Phe Thr Phe
            35                  40                  45
Ser Arg Ser Met His Trp Val Arg Gln Ala Pro Gly Lys Gly Leu
    50                  55                  60
Glu Trp Val Ala Ile Ile Ser Ser Asp Gly Ser Lys Ile Tyr Tyr Ala
65                  70                  75                  80
Asp Ser Val Glu Gly Arg Phe Ile Ile Ser Arg Asp Asn Ser Arg Asn
                85                  90                  95
Thr Leu Tyr Leu Gln Met Ser Ser Leu Arg Pro Glu Asp Thr Ala Leu
            100                 105                 110
Tyr His Cys Ala Lys Asp Trp Gln Trp Leu Val Asp Ser Trp Gly Gln
            115                 120                 125
Gly Thr Leu Val Ala Val Ser Ser Ala Ser Thr Lys Gly Pro Ser Val
            130                 135                 140
Phe Pro Leu Ala Pro Cys Ser Arg Ser Thr Ser Glu Ser Thr Ala Ala
145                 150                 155                 160
Leu Gly Cys Leu Val Lys Asp Tyr Phe Pro Glu Pro Val Thr Val Ser
                165                 170                 175
Trp Asn Ser Gly Ala Leu Thr Ser Gly Val His Thr Phe Pro Ala Val
                180                 185                 190
Leu Gln Ser Ser Gly Leu Tyr Ser Leu Ser Ser Val Val Thr Val Pro
            195                 200                 205
Ser Ser Asn Phe Gly Thr Gln Thr Tyr Thr Cys Asn Val Asp His Lys
            210                 215                 220
Pro Ser Asn Thr Lys Val Asp Lys Thr Val Glu Arg Lys Cys Cys Val
225                 230                 235                 240
Glu Cys Pro Pro Cys Pro Ala Pro Val Ala Gly Pro Ser Val Phe
                245                 250                 255
Leu Phe Pro Pro Lys Pro Lys Asp Thr His His His His His His
            260                 265                 270

<210> SEQ ID NO 147
<211> LENGTH: 261
<212> TYPE: PRT
<213> ORGANISM: homosapiens

<400> SEQUENCE: 147

Met Gln Cys Glu Glu Gln Leu Glu Glu Ser Gly Gly Gly Leu Val Gln
1               5                   10                  15
Pro Gly Gly Ser Leu Arg Leu Ser Cys Val Ala Ser Gly Phe Gly Phe
            20                  25                  30
Gly Ile Tyr Glu Met Asn Trp Val Arg Gln Thr Pro Gly Lys Gly Leu
            35                  40                  45
Glu Trp Val Ser Tyr Ile Ser Thr Gly Gly Thr Ile Tyr Asp Ala
    50                  55                  60
Asp Ser Val Lys Gly Arg Phe Thr Ile Ser Arg Asp Asn Ala Glu Asn
65                  70                  75                  80
Ser Leu His Leu Gln Met Lys Ser Leu Arg Ala Glu Asp Thr Ala Ile
                85                  90                  95
Tyr Tyr Cys Ala Arg Arg Gly Arg Asn Gly Tyr Asp Arg Val His Gly
            100                 105                 110
Met Asp Leu Trp Gly Gln Gly Thr Thr Val Ile Val Ser Ser Ala Ser
            115                 120                 125
```

```
Thr Lys Gly Pro Ser Val Phe Pro Leu Ala Pro Cys Ser Arg Ser Thr
            130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
                195                 200                 205

Cys Asn Val Asp His Lys Pro Ser Asn Thr Lys Val Asp Lys Thr Val
210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr His
                245                 250                 255

His His His His His
            260

<210> SEQ ID NO 148
<211> LENGTH: 279
<212> TYPE: PRT
<213> ORGANISM: homosapiens

<400> SEQUENCE: 148

Met Glu Phe Gly Leu Ser Trp Leu Phe Leu Val Ala Ile Val Lys Gly
1               5                   10                  15

Val Gln Cys Ala Val Gln Leu Val Glu Ser Gly Gly Gly Leu Val Gln
                20                  25                  30

Pro Gly Gly Ser Leu Arg Leu Ser Cys Ala Ala Ser Gly Phe Thr Val
            35                  40                  45

Ser Asn Thr Tyr Met Ala Trp Val Arg Gln Ala Pro Gly Lys Gly Leu
        50                  55                  60

Glu Trp Val Ser Val Leu Tyr Ala Gly Ala Tyr Thr Glu Tyr Arg Asp
65                  70                  75                  80

Ser Val Lys Gly Arg Phe Thr Ile Ser Arg Asp Asn Pro Lys Asn Thr
                85                  90                  95

Val His Leu Gln Met Asn Arg Leu Arg Asp Glu Asp Thr Ala Val Tyr
            100                 105                 110

Tyr Cys Ala Arg Gly Ser Asn Pro Cys Ser Gly Ala Cys Phe Ser Asp
        115                 120                 125

Tyr Trp Gly Gln Gly Ile Leu Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240
```

```
Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr His His His His His His
        275
```

<210> SEQ ID NO 149
<211> LENGTH: 279
<212> TYPE: PRT
<213> ORGANISM: homosapiens

<400> SEQUENCE: 149

```
Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Asp Leu Val Gln
            20                  25                  30

Pro Gly Gly Ser Leu Arg Leu Ser Cys Val Ala Ser Gly Phe Ile Leu
        35                  40                  45

Ser Asp Tyr Ala Met Asn Trp Val Arg Gln Ala Pro Gly Lys Gly Leu
    50                  55                  60

Glu Trp Val Ser Ala Leu Thr Gly Ser Gly Asp Ser Thr His Tyr Ala
65                  70                  75                  80

Asp Ser Val Lys Gly Arg Phe Thr Ile Ser Arg Asp Thr Ser Lys Asn
                85                  90                  95

Thr Leu Tyr Leu Gln Met Asn Ser Leu Arg Val Glu Asp Thr Ala Val
            100                 105                 110

Tyr Tyr Cys Ala Asn Asn Pro His Tyr Asp Ala Gly Ser Pro His Arg
        115                 120                 125

Ala Ser Glu Asp Tyr Trp Gly Gln Gly Thr Leu Val Thr Val Ser Ser
    130                 135                 140

Thr Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr His His His His His His
        275
```

<210> SEQ ID NO 150
<211> LENGTH: 282
<212> TYPE: PRT
<213> ORGANISM: homosapiens

<400> SEQUENCE: 150

```
Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Asp Leu Val Gln
            20                  25                  30

Pro Gly Gly Ser Leu Arg Leu Ser Cys Ala Ala Ser Gly Phe Thr Phe
        35                  40                  45

Ser Asn Tyr Ala Met Thr Trp Val Arg Gln Ala Pro Gly Lys Gly Leu
    50                  55                  60

Glu Trp Val Ala Thr Ile Gly Ala Pro Gly Thr Asp Thr Tyr Tyr Ala
65                  70                  75                  80

Asp Ser Val Lys Gly Arg Phe Thr Ile Ser Arg Asp Asn Ser Lys Asn
                85                  90                  95

Met Leu Tyr Leu His Met Asn Ser Leu Arg Ala Glu Asp Thr Ala Ile
            100                 105                 110

His Tyr Cys Ala Lys Asp His Arg Ile Ile His Ser Thr Ala Trp Ala
        115                 120                 125

Thr Leu Pro Asp Ala Phe Asp Val Trp Gly Gln Gly Thr Val Val Thr
    130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Asn Phe Gly
    210                 215                 220

Thr Gln Thr Tyr Thr Cys Asn Val Asp His Lys Pro Ser Asn Thr Lys
225                 230                 235                 240

Val Asp Lys Thr Val Glu Arg Lys Cys Cys Val Glu Cys Pro Pro Cys
                245                 250                 255

Pro Ala Gln Pro Val Ala Gly Pro Ser Val Phe Leu Phe Pro Pro Lys
            260                 265                 270

Pro Lys Asp Thr His His His His His His
        275                 280

<210> SEQ ID NO 151
<211> LENGTH: 282
<212> TYPE: PRT
<213> ORGANISM: homosapiens

<400> SEQUENCE: 151

Met Glu Phe Gly Leu Ser Trp Ile Phe Leu Ala Ala Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Ala Trp Met Thr Trp Val Arg Gln Ala Pro Gly Lys Gly Leu
    50                  55                  60

Glu Trp Val Gly Arg Ile Arg Ser Lys Thr Asp Gly Glu Thr Leu Asp
65                  70                  75                  80

Tyr Ala Ala Pro Val Lys Gly Arg Phe Thr Ile Ser Arg Asp Asp Ser
```

```
            85                  90                  95
Lys Asn Thr Leu Tyr Leu Gln Met Asn Ser Leu Lys Thr Ala Asp Thr
            100                 105                 110

Gly Val Tyr Tyr Cys Thr Thr Met Thr Thr Ala Ala Thr Ala Val
            115                 120                 125

Ile Arg Pro Pro His Asp Asp Trp Gly Gln Gly Thr Leu Val Thr
            130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
                180                 185                 190

Leu Thr Ser Gly Val His Thr Phe Pro Ala Val Leu Gln Ser Ser Gly
                195                 200                 205

Leu Tyr Ser Leu Ser Ser Val Val Thr Val Pro Ser Ser Asn Phe Gly
            210                 215                 220

Thr Gln Thr Tyr Thr Cys Asn Val Asp His Lys Pro Ser Asn Thr Lys
225                 230                 235                 240

Val Asp Lys Thr Val Glu Arg Lys Cys Cys Val Glu Cys Pro Pro Cys
                245                 250                 255

Pro Ala Pro Pro Val Ala Gly Pro Ser Val Phe Leu Phe Pro Pro Lys
            260                 265                 270

Pro Lys Asp Thr His His His His His His
            275                 280

<210> SEQ ID NO 152
<211> LENGTH: 283
<212> TYPE: PRT
<213> ORGANISM: homosapiens

<400> SEQUENCE: 152

Met Glu Phe Gly Leu Ser Trp Val Phe Leu Val Ala Ile Leu Lys Gly
1               5                   10                  15

Val Gln Cys Asp Val Gln Leu Val Glu Ser Gly Gly Gly Leu Glu Gln
                20                  25                  30

Pro Gly Arg Ser Leu Arg Leu Ser Cys Thr Thr Ser Gly Phe Thr Phe
            35                  40                  45

Ser Asp Phe Ala Ile Ser Trp Val Arg Gln Ala Pro Gly Lys Gly Leu
50                  55                  60

Glu Trp Val Gly Phe Ile Arg Ser Lys Pro Tyr Gly Glu Thr Thr Glu
65                  70                  75                  80

Ile Ala Ala Ser Val Lys Gly Arg Phe Ser Ile Ser Arg Asp Asn Ser
                85                  90                  95

Arg Ser Ile Ala Tyr Leu Gln Met Asn Ser Leu Glu Thr Glu Asp Thr
            100                 105                 110

Ala Arg Tyr Phe Cys Thr Arg Phe Gly Pro Tyr Tyr Leu Gly Arg
            115                 120                 125

Gly Gly Ser His Asp Ser Phe Asp Ile Trp Gly Arg Gly Thr Met Val
            130                 135                 140

Thr Val Ser Ser Ala Ser Thr Lys Gly Pro Ser Val Phe Pro Leu Ala
145                 150                 155                 160

Pro Cys Ser Arg Ser Thr Ser Glu Ser Thr Ala Ala Leu Gly Cys Leu
                165                 170                 175
```

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Asn Phe
    210                 215                 220

Gly Thr Gln Thr Tyr Thr Cys Asn Val Asp His Lys Pro Ser Asn Thr
225                 230                 235                 240

Lys Val Asp Lys Thr Val Glu Arg Lys Cys Cys Val Glu Cys Pro Pro
                245                 250                 255

Cys Pro Ala Pro Pro Val Ala Gly Pro Ser Val Phe Leu Phe Pro Pro
            260                 265                 270

Lys Pro Lys Asp Thr His His His His His His
            275                 280

<210> SEQ ID NO 153
<211> LENGTH: 323
<212> TYPE: PRT
<213> ORGANISM: homosapiens

<400> SEQUENCE: 153

Met Glu Phe Gly Leu Ser Trp Val Phe Leu Val Ile Ile Leu Lys Gly
1               5                   10                  15

Val Gln Cys Glu Val Gln Leu Val Glu Ser Gly Gly Asn Leu Val Arg
            20                  25                  30

Pro Gly Gly Ser Leu Arg Ile Ser Cys Thr Gly Ser Gly Leu Asn Val
        35                  40                  45

Ser Asn Asp Asp Met Asn Trp Val Arg Gln Ala Pro Gly Lys Gly Leu
    50                  55                  60

Glu Trp Val Ser Leu Ile Ser Ile Gly Gly Ser Glu Tyr Tyr Ala Asp
65                  70                  75                  80

Ser Val Lys Gly Arg Leu Thr Ile Ser Arg Asp Asn Ala Lys Asn Thr
                85                  90                  95

Leu His Leu Gln Met Asn Ser Leu Arg Ala Glu Asp Thr Ala Val Tyr
            100                 105                 110

Tyr Cys Ala Arg Glu Ala Ser Gly Gly Tyr Tyr Leu Asp Tyr Trp Gly
        115                 120                 125

Gln Gly Ala Leu Val Thr Val Ser Ser Ala Ser Thr Lys Gly Pro Ser
    130                 135                 140

Val Phe Pro Leu Ala Pro Cys Ser Arg Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Thr Cys Asn Val Asn His
    210                 215                 220

Lys Pro Ser Asn Thr Lys Val Asp Lys Arg Val Glu Leu Lys Thr Pro
225                 230                 235                 240

Leu Gly Asp Thr Thr His Thr Cys Pro Arg Cys Pro Glu Pro Lys Ser
                245                 250                 255

Cys Asp Thr Pro Pro Pro Cys Pro Arg Cys Pro Glu Pro Lys Ser Cys
            260                 265                 270

Asp Thr Pro Pro Pro Cys Pro Arg Cys Pro Glu Pro Lys Ser Cys Asp
        275                 280                 285

Thr Pro Pro Pro Cys Pro Arg Cys Pro Ala Pro Glu Leu Leu Gly Gly
        290                 295                 300

Pro Ser Val Phe Leu Phe Pro Pro Lys Pro Lys Asp Thr His His His
305                 310                 315                 320

His His His

<210> SEQ ID NO 154
<211> LENGTH: 279
<212> TYPE: PRT
<213> ORGANISM: homosapiens

<400> SEQUENCE: 154

Met Glu Leu Gly Leu Ser Trp Val Phe Leu Val Val Ile Leu Gln Gly
1               5                   10                  15

Ala His Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Ser
        35                  40                  45

Ser Asp His Tyr Met Asp Trp Val Arg Gln Ala Pro Gly Lys Gly Leu
    50                  55                  60

Glu Trp Val Gly Phe Ile Arg Ser Lys Ala Tyr Gly Trp Thr Ser Glu
65                  70                  75                  80

Tyr Ala Ala Ser Val Lys Gly Arg Phe Thr Phe Ser Arg Tyr Asp Ser
                85                  90                  95

Lys Ser Ile Ala Tyr Leu Gln Val Asp Ser Leu Lys Thr Asp Asp Thr
            100                 105                 110

Ala Val Tyr Tyr Cys Thr Ser His Ser Gln Gln Arg Pro Ala Pro Leu
        115                 120                 125

Arg Ser Leu Asp Tyr Trp Gly Arg Gly Thr Leu Ile Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Pro His His His His His His
        275

<210> SEQ ID NO 155
<211> LENGTH: 271
<212> TYPE: PRT
<213> ORGANISM: homosapiens

<400> SEQUENCE: 155

| | | | | | | | | | | | | | | |
|---|---|---|---|---|---|---|---|---|---|---|---|---|---|---|
|Met|Glu|Phe|Gly|Leu|Ser|Trp|Val|Phe|Leu|Val|Ala|Ile|Leu|Glu|Gly|
|1| | | |5| | | | |10| | | | |15| |

Val Gln Cys Glu Glu Gln Leu Val Glu Ser Gly Gly Gly Leu Val Gln
           20               25               30

Pro Gly Gly Ser Leu Arg Leu Ser Cys Ala Ala Ser Gly Phe Met Phe
        35               40               45

Arg Asp His Tyr Met Ile Trp Val Arg Gln Ala Pro Gly Lys Gly Leu
 50                   55               60

Glu Trp Val Ala Lys Ile Lys Pro Asp Gly Glu Lys Tyr Tyr Val
65               70              75             80

Asp Ser Val Lys Gly Arg Phe Ser Ile Ser Arg Asp Asn Ala Lys Lys
           85               90              95

Ser Leu Phe Leu Gln Met Asn Ser Leu Arg Val Glu Asp Thr Ala Val
           100             105            110

Tyr Tyr Cys Ala Arg Glu His Trp Trp Arg Val Asp Cys Trp Gly Gln
           115             120            125

Gly Thr Leu Val Thr Val Ser Ser Ala Ser Thr Lys Gly Pro Ser Val
           130             135            140

Phe Pro Leu Ala Pro Cys Ser Arg Ser Thr Ser Glu Ser Thr Ala Ala
145             150             155            160

Leu Gly Cys Leu Val Lys Asp Tyr Phe Pro Glu Pro Val Thr Val Ser
           165             170            175

Trp Asn Ser Gly Ala Leu Thr Ser Gly Val His Thr Phe Pro Ala Val
           180             185            190

Leu Gln Ser Ser Gly Leu Tyr Ser Leu Ser Ser Val Val Thr Val Pro
           195             200            205

Ser Ser Asn Phe Gly Thr Gln Thr Tyr Thr Cys Asn Val Asp His Lys
           210             215            220

Pro Ser Asn Thr Lys Val Asp Lys Thr Val Glu Arg Lys Cys Cys Val
225             230             235            240

Glu Cys Pro Pro Cys Pro Ala Pro Pro Val Ala Gly Pro Ser Val Phe
           245             250            255

Leu Phe Pro Pro Lys Pro Lys Asp Thr His His His His His His
           260             265            270

<210> SEQ ID NO 156
<211> LENGTH: 282
<212> TYPE: PRT
<213> ORGANISM: homosapiens

<400> SEQUENCE: 156

Met Glu Phe Gly Leu Ser Trp Val Phe Leu Val Ala Ile Leu Gln Gly
1               5              10             15

Val Gln Cys Glu Val Gln Leu Val Glu Ser Gly Gly Asp Leu Val Arg
           20               25               30

Pro Gly Gly Ser Leu Arg Leu Ser Cys Val Gly Ser Gly Phe Thr Phe
        35               40               45

Ser Asp His Phe Met Asp Trp Val Arg Gln Ala Pro Gly Lys Gly Leu
 50                   55               60

Glu Trp Val Ala Arg Ile Arg Asn Glu Gly Asn Arg Phe Pro Thr Glu
65               70              75             80

Tyr Ala Ala Ser Val Lys Asp Arg Phe Thr Ile Ser Arg Asp Asp Ser
           85               90              95

```
Lys Thr Ser Val Phe Leu Gln Val Asp Ser Leu Arg Ala Asp Asp Thr
            100                 105                 110

Ala Val Tyr Tyr Cys Ala Arg Gly His Tyr Tyr Ser Asp Ser Arg Gly
        115                 120                 125

Tyr Tyr Ala His Phe Phe Asp Phe Trp Gly Gln Gly Thr Leu Val Thr
    130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Asn Phe Gly
    210                 215                 220

Thr Gln Thr Tyr Thr Cys Asn Val Asp His Lys Pro Ser Asn Thr Lys
225                 230                 235                 240

Val Asp Lys Thr Val Glu Arg Lys Cys Cys Val Glu Cys Pro Pro Cys
                245                 250                 255

Pro Ala Pro Pro Val Ala Gly Pro Ser Val Phe Leu Phe Pro Pro Lys
            260                 265                 270

Pro Lys Asp Thr His His His His His His
        275                 280

<210> SEQ ID NO 157
<211> LENGTH: 307
<212> TYPE: PRT
<213> ORGANISM: homosapiens

<400> SEQUENCE: 157

Met Glu Phe Gly Leu Ser Trp Val Phe Leu Val Ala Ile Val Lys Gly
1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Val Arg Gln Ala Pro Gly Met Gly Leu
    50                  55                  60

Glu Trp Leu Ser Tyr Thr Ser Gly Tyr Gly Ser Thr Tyr Asn Thr
65                  70                  75                  80

Asp Ser Val Lys Gly Arg Phe Thr Ile Ser Arg Asp Asn Ala Lys Asn
                85                  90                  95

Ser Leu Ser Leu Gln Met Thr Ser Leu Arg Val Asp Asp Thr Ala Val
            100                 105                 110

Tyr Tyr Cys Ala Arg Pro Leu Arg Gly Ala Ile Gln Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Cys Ser Arg Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
```

```
                180                 185                 190
Leu Gln Ser Ser Gly Leu Tyr Ser Leu Ser Ser Val Val Thr Val Pro
            195                 200                 205

Ser Ser Ser Leu Gly Thr Gln Thr Tyr Thr Cys Asn Val Asn His Lys
        210                 215                 220

Pro Ser Asn Thr Lys Val Asp Lys Arg Val Glu Leu Lys Thr Pro Leu
225                 230                 235                 240

Gly Asp Thr Thr His Thr Cys Pro Arg Cys Pro Glu Pro Lys Ser Cys
                245                 250                 255

Asp Thr Pro Pro Pro Cys Pro Arg Cys Pro Glu Pro Lys Ser Cys Asp
            260                 265                 270

Thr Pro Pro Pro Cys Pro Arg Cys Pro Ala Pro Glu Leu Leu Gly Gly
        275                 280                 285

Pro Ser Val Phe Leu Phe Pro Pro Lys Pro Lys Asp Thr His His His
        290                 295                 300

His His His
305

<210> SEQ ID NO 158
<211> LENGTH: 274
<212> TYPE: PRT
<213> ORGANISM: homosapiens

<400> SEQUENCE: 158

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Lys Ser Leu Arg Leu Ser Cys Ala Ala Ser Gly Phe Thr Leu
        35                  40                  45

Ser His Tyr Ala Val His Trp Val Arg Gln Ala Pro Gly Lys Gly Leu
    50                  55                  60

Glu Trp Val Ser Gly Ile Asn Ser Thr Gly Gly Thr Thr Tyr Tyr Ala
65                  70                  75                  80

Asp Ser Val Leu Gly Arg Phe Thr Ile Ser Arg Asp Asn Ser Lys Lys
                85                  90                  95

Ile Leu Tyr Leu His Met Asn Ile Leu Arg Ala Asp Asp Thr Ala Val
            100                 105                 110

Tyr Tyr Cys Ala Arg Pro Tyr Tyr Asp Ile Trp Asn His Phe Asp Pro
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240
```

```
Cys Cys Val Glu Cys Pro Pro Cys Pro Ala Pro Pro Val Ala Gly Pro
            245                 250                 255

Ser Val Phe Leu Phe Pro Pro Lys Pro Lys Asp Thr His His His His
            260                 265                 270

His His

<210> SEQ ID NO 159
<211> LENGTH: 277
<212> TYPE: PRT
<213> ORGANISM: homosapiens

<400> SEQUENCE: 159

Met Glu Phe Gly Leu Ser Trp Val Phe Leu Val Ala Ile Leu Glu Gly
1               5                   10                  15

Val Gln Cys Glu Val Lys Leu Val Glu Ser Gly Gly Gly Leu Val Gln
            20                  25                  30

Pro Gly Gly Ser Leu Arg Leu Ser Cys Ala Ala Ser Gly Phe Ser Phe
        35                  40                  45

Ser Asn Phe Glu Met Asn Trp Leu Arg Leu Ala Pro Gly Lys Gly Pro
    50                  55                  60

Glu Trp Val Ser His Ile Gly Ser Asp Val Thr Phe Lys His Tyr Ala
65                  70                  75                  80

Asp Ser Val Lys Gly Arg Phe Thr Ile Ser Arg Asp Asn Ala Met Asn
                85                  90                  95

Ser Val Phe Leu Gln Met Asp Ser Leu Arg Val Glu Asp Thr Ala Val
            100                 105                 110

Tyr Tyr Cys Ala Lys Glu Val Thr His Leu His Ser Gly Tyr Asp Ala
        115                 120                 125

Phe Asp Leu Trp Gly Gln Gly Thr Leu Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
            260                 265                 270

His His His His His
        275

<210> SEQ ID NO 160
<211> LENGTH: 254
<212> TYPE: PRT
<213> ORGANISM: homosapiens

<400> SEQUENCE: 160

Met Glu Ser Gly Gly Gly Val Val Gln Pro Gly Arg Ser Leu Arg Leu
```

```
1               5                   10                  15
Ser Cys Ala Gly Ser Gly Phe Thr Phe Ser Ser His Ala Ile His Trp
            20                  25                  30

Val Arg Gln Ala Pro Gly Lys Gly Leu Glu Trp Val Ala Leu Ile Ser
            35                  40                  45

Tyr Asp Gly Ser Asp Lys Tyr Tyr Ala Asp Ser Val Lys Gly Arg Phe
        50                  55                  60

Thr Ile Ser Arg Asp Asp Ser Lys Asn Thr Ile Tyr Leu Gln Met Asn
65                  70                  75                  80

Ser Leu Arg Pro Glu Asp Thr Ala Met Tyr Tyr Cys Val Lys Thr Met
                85                  90                  95

Val Arg Gly Ser Phe Tyr Tyr Gly Val Asp Val Trp Gly His Gly
                100                 105                 110

Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr His His His His His His
                245                 250

<210> SEQ ID NO 161
<211> LENGTH: 278
<212> TYPE: PRT
<213> ORGANISM: homosapiens

<400> SEQUENCE: 161

Met Glu Phe Gly Leu Ser Trp Val Phe Leu Val Ala Ile Leu Lys Gly
1               5                   10                  15

Val Gln Cys Glu Glu Phe Leu Leu Glu Ser Gly Gly Gly Leu Val Arg
            20                  25                  30

Pro Gly Gly Ser Leu Arg Leu Ser Cys Ala Thr Ser Gly Phe Arg Phe
            35                  40                  45

Arg Asp His Thr Met Ala Trp Val Arg Gln Ala Pro Gly Lys Gly Leu
        50                  55                  60

Glu Trp Ile Ser Ser Val Ser Ser Asp Ala Asp Asn Gly Asn Thr Tyr
65                  70                  75                  80

Tyr Ala Asp Ser Val Arg Gly Arg Phe Thr Val Ser Arg Asp Asn Ser
                85                  90                  95

Met Asn Thr Val His Leu Gln Met Asp Ile Leu Arg Val Asp Asp Thr
            100                 105                 110

Ala Val Tyr Phe Cys Ala Arg Glu Gly Met Trp Gln Val Gly Tyr Trp
            115                 120                 125
```

```
Tyr Phe Asn Leu Trp Gly Arg Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
            165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

His His His His His His
            275

<210> SEQ ID NO 162
<211> LENGTH: 277
<212> TYPE: PRT
<213> ORGANISM: homosapiens
<220> FEATURE:
<221> NAME/KEY: MISC_FEATURE
<222> LOCATION: (270)..(270)
<223> OTHER INFORMATION: Xaa is Tyr or His or Asn or Asp.

<400> SEQUENCE: 162

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Tyr Tyr Gly Met His Trp Val Arg Gln Ala Pro Gly Lys Gly Leu
    50                  55                  60

Glu Trp Val Ala Leu Ile Ser Tyr Asp Gly Ser Lys Lys Tyr Tyr Ala
65                  70                  75                  80

Asp Ser Val Lys Gly Arg Phe Thr Ile Ser Arg Asp Asp Ser Lys Asn
                85                  90                  95

Thr Leu Tyr Leu Gln Met Asn Ser Leu Arg Pro Glu Asp Thr Ala Met
            100                 105                 110

Tyr Phe Cys Ala Lys Asp Leu Gly Tyr Thr Ser Gly Ser Pro Leu Trp
        115                 120                 125

Gly His Gly Thr Met Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
```

```
                195                 200                 205
Val Pro Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Xaa Thr His
            260                 265                 270

His His His His His
        275

<210> SEQ ID NO 163
<211> LENGTH: 278
<212> TYPE: PRT
<213> ORGANISM: homosapiens

<400> SEQUENCE: 163

Met Glu Phe Gly Leu Ile Trp Val Phe Leu Val Ala Leu Leu Arg Gly
1               5                   10                  15

Val Gln Cys Gln Ala Gln Leu Val Glu Ser Gly Gly Gly Val Val Gln
            20                  25                  30

Pro Gly Arg Ser Gln Arg Pro Ser Cys Gly Ala Ser Gly Phe Arg Phe
        35                  40                  45

Ser Asp Tyr Gly Met His Trp Val Arg Gln Ala Pro Gly Arg Gly Leu
    50                  55                  60

Glu Trp Val Ala Phe Ile Ser Phe Asp Gly Thr Asp Lys Tyr Tyr Ala
65                  70                  75                  80

Gly Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Leu
            100                 105                 110

Tyr Tyr Cys Ala Lys Val Val Glu Tyr Thr Leu Phe Pro Ala Pro Val
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

His His His His His His
        275
```

<210> SEQ ID NO 164
<211> LENGTH: 271
<212> TYPE: PRT
<213> ORGANISM: homosapiens

<400> SEQUENCE: 164

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Gly Ser Leu Arg Leu Ser Cys Ala Ala Ser Gly Phe Thr Phe
        35                  40                  45

Ser Arg Ser Ser Met His Trp Val Arg Gln Ala Pro Gly Lys Gly Leu
50                  55                  60

Glu Trp Val Ala Ile Ile Ser Ser Asp Gly Ser Lys Ile Tyr Tyr Ala
65                  70                  75                  80

Asp Ser Val Glu Gly Arg Phe Ile Ile Ser Arg Asp Asn Ser Arg Asn
                85                  90                  95

Thr Leu Tyr Leu Gln Met Ser Ser Leu Arg Pro Glu Asp Thr Ala Leu
            100                 105                 110

Tyr His Cys Ala Lys Asp Trp Gln Trp Leu Val Asp Ser Trp Gly Gln
        115                 120                 125

Gly Thr Leu Val Ala Phe Ser Ser Ala Ser Thr Lys Gly Pro Ser Val
130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr His His His His His His
            260                 265                 270

<210> SEQ ID NO 165
<211> LENGTH: 281
<212> TYPE: PRT
<213> ORGANISM: homosapiens

<400> SEQUENCE: 165

Met Glu Phe Gly Leu Ser Trp Val Phe Leu Val Ala Leu Leu Arg Gly
1               5                   10                  15

Val Gln Cys Gln Val Gln Met Val Glu Ser Gly Gly Gly Val Val Gln
            20                  25                  30

Pro Gly Gly Ser Leu Arg Leu Ser Cys Ala Ala Ser Gly Phe Thr Phe
        35                  40                  45

Thr Ser His Gly Met His Trp Val Arg Gln Ala Pro Gly Lys Gly Leu
50                  55                  60

Glu Trp Val Ala Leu Met Ser Tyr Asp Gly Thr Asn Lys Tyr Tyr Ala
65                  70                  75                  80

Asp Ser Val Lys Gly Arg Ser Thr Ile Ser Arg Asp Asn Ser Lys Asn
                85                  90                  95

Thr Phe Phe Leu Gln Met Asn Ala Leu Thr Ala Glu Asp Thr Ala Val
            100                 105                 110

Tyr Tyr Cys Ala Lys Asp Arg Cys Val Ser Arg Cys Ser Tyr Asp
        115                 120                 125

Phe Ser Asp Gly Met Asp Val Trp Gly Gln Gly Thr Val Ile Val
    130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr His His His His His His
            275                 280

<210> SEQ ID NO 166
<211> LENGTH: 277
<212> TYPE: PRT
<213> ORGANISM: homosapiens

<400> SEQUENCE: 166

Met Glu Phe Arg Leu Ser Trp Val Phe Leu Val Ala Leu Leu Arg Gly
1               5                   10                  15

Val Arg Cys Gln Met Gln Leu Val Glu Ser Gly Gly Gly Val Val Gln
            20                  25                  30

Pro Gly Gly Ser Leu Arg Leu Ser Cys Ala Ala Ser Gly Phe Thr Phe
        35                  40                  45

Ser His Tyr Gly Met His Trp Val Arg Gln Ala Pro Gly Lys Gly Pro
    50                  55                  60

Glu Trp Val Ala Val Thr Trp Ser Asp Gly Arg Phe Lys Glu Tyr Ala
65                  70                  75                  80

Asp Ser Val Lys Gly Arg Phe Thr Val Ser Arg Asp Asn Ser Arg Asn
                85                  90                  95

Thr Leu Tyr Leu Gln Met Asn Ser Leu Arg Pro Glu Asp Thr Ala Val
            100                 105                 110

Tyr Tyr Cys Ala Arg Gly Gly Ser Gly Trp Lys Thr Gly Trp Gly
        115                 120                 125

Phe Asp Tyr Trp Gly Gln Gly Thr Leu Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
            260                 265                 270

His His His His His
        275

<210> SEQ ID NO 167
<211> LENGTH: 276
<212> TYPE: PRT
<213> ORGANISM: homosapiens

<400> SEQUENCE: 167

Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Val Val Glu
            20                  25                  30

Pro Gly Arg Ser Leu Arg Leu Ser Tyr Ala Ala Ser Gly Phe Asp Leu
        35                  40                  45

Asn Arg Tyr Ala Met His Trp Ala Arg Lys Ala Pro Gly Lys Gly Leu
    50                  55                  60

Glu Trp Val Ala Gly Phe Ser Arg Thr Asp Asn Val Lys Val Tyr Ala
65                  70                  75                  80

Asp Ser Val Lys Gly Arg Phe Thr Ile Thr Arg Asp Glu Ala Arg Asn
                85                  90                  95

Ala Leu Gln Leu Glu Met Phe Ser Leu Arg Thr Asp Asp Ser Ala Leu
            100                 105                 110

Tyr Tyr Cys Val Lys Asp Ser Gly Pro Ser Val Val Pro Ala Arg Leu
        115                 120                 125

Val Thr Trp Gly Gln Gly Ile Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala

```
                    245                 250                 255
Gly Pro Ser Val Phe Leu Phe Pro Pro Lys Pro Lys Asp Thr His His
            260                 265                 270
His His Pro His
        275

<210> SEQ ID NO 168
<211> LENGTH: 267
<212> TYPE: PRT
<213> ORGANISM: homosapiens

<400> SEQUENCE: 168

Met Glu Phe Gly Leu Ser Trp Val Phe Leu Val Ala Ile Leu Lys Gly
1               5                   10                  15

Val Gln Cys Gln Val Gln Leu Val Glu Ser Gly Gly Gly Leu Val Gln
            20                  25                  30

Pro Gly Gly Ser Leu Arg Leu Ser Cys Ala Val Ser Gly Phe Thr Ile
        35                  40                  45

Ser Ser Ser Ala Leu Ser Trp Val Arg Gln Ala Pro Gly Lys Gly Leu
    50                  55                  60

Glu Trp Val Ser Thr Ile Ala Gly Asn Ala Gly His Ser Phe Tyr Ala
65                  70                  75                  80

Asp Ser Val Lys Gly Arg Phe Ser Ile Ser Arg Asp Thr Ser Lys Asn
                85                  90                  95

Thr Leu Phe Leu Gln Leu Asn Ser Leu Arg Thr Glu Asp Thr Ala Val
            100                 105                 110

Tyr Tyr Cys Glu Lys Arg Phe Asp Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Asn Phe
        195                 200                 205

Gly Thr Gln Thr Tyr Thr Cys Asn Val Asp His Lys Pro Ser Asn Thr
    210                 215                 220

Lys Val Asp Lys Thr Val Glu Arg Lys Cys Cys Val Glu Cys Pro Pro
225                 230                 235                 240

Cys Pro Ala Pro Pro Val Ala Gly Pro Ser Val Phe Leu Phe Pro Pro
                245                 250                 255

Lys Pro Lys Asp Thr Gln His His His His
            260                 265

<210> SEQ ID NO 169
<211> LENGTH: 285
<212> TYPE: PRT
<213> ORGANISM: homosapiens

<400> SEQUENCE: 169

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
```

```
            20                  25                  30
Pro Gly Arg Ser Leu Arg Leu Ser Cys Ala Glu Ser Gly Phe Thr Phe
         35                  40                  45
Ser Ser Tyr Gly Met His Trp Val Arg Gln Ala Pro Gly Lys Gly Leu
 50                  55                  60
Glu Trp Val Ala Val Ile Trp Phe Asp Gly Arg Asn Lys Tyr Tyr Ala
 65                  70                  75                  80
Asp Ser Val Lys Gly Arg Phe Thr Ile Ser Arg Asp Asn Ser Lys Asn
                 85                  90                  95
Thr Leu Tyr Leu Gln Met Asn Arg Leu Ser Ala Glu Asp Thr Ala Val
            100                 105                 110
Tyr Tyr Cys Ala Arg Asp Arg Tyr Cys Ser Asp Gly Thr Cys Ser Asp
            115                 120                 125
Gly Gly Asn Tyr Leu Asp Tyr Trp Gly Gln Gly Thr Leu Val Thr Val
        130                 135                 140
Ser Ser Ala Ser Thr Lys Gly Pro Ser Val Phe Pro Leu Ala Pro Ser
145                 150                 155                 160
Ser Lys Ser Thr Ser Gly Gly Thr Ala Ala Leu Gly Cys Leu Val Lys
                165                 170                 175
Asp Tyr Phe Pro Glu Pro Val Thr Val Ser Trp Asn Ser Gly Ala Leu
            180                 185                 190
Thr Ser Gly Val His Thr Phe Pro Ala Val Leu Gln Ser Ser Gly Leu
        195                 200                 205
Tyr Ser Leu Ser Ser Val Val Thr Val Pro Ser Ser Ser Leu Gly Thr
    210                 215                 220
Gln Thr Tyr Ile Cys Asn Val Asn His Lys Pro Ser Asn Thr Lys Val
225                 230                 235                 240
Asp Lys Lys Val Glu Pro Lys Ser Cys Asp Lys Thr His Thr Cys Pro
                245                 250                 255
Pro Cys Pro Ala Pro Glu Leu Leu Gly Gly Pro Ser Val Phe Leu Phe
            260                 265                 270
Pro Pro Lys Pro Lys Asp Thr His His His His His His
        275                 280                 285

<210> SEQ ID NO 170
<211> LENGTH: 273
<212> TYPE: PRT
<213> ORGANISM: homosapiens

<400> SEQUENCE: 170

Met Glu Phe Gly Leu Ser Trp Val Phe Leu Val Val Ile Leu Gln Gly
 1               5                  10                  15
Val Gln Cys Glu Val Gln Leu Val Glu Ser Gly Gly Asp Leu Val Arg
            20                  25                  30
Pro Gly Gly Ser Leu Arg Leu Ser Cys Val Gly Ser Gly Phe Ser Phe
         35                  40                  45
Ser Asp Tyr Phe Met Asp Trp Val Arg Gln Ala Pro Gly Lys Gly Leu
 50                  55                  60
Glu Trp Val Ala Arg Ile Arg Asn Lys Arg Asn Arg Tyr Ser Thr Gln
 65                  70                  75                  80
His Ala Ala Ser Val Lys Asp Arg Phe Thr Ile Ser Arg Asp Asp Ser
                 85                  90                  95
Lys Ser Ser Val Phe Leu His Met Asn Ser Leu Lys Thr Glu Asp Thr
            100                 105                 110
```

Ala Val Tyr Tyr Cys Ala Arg Asp Tyr Gln Gly Leu Gly Thr Ser Trp
                115                 120                 125

Gly Gln Gly Thr Leu Val Thr Val Ser Ser Ala Ser Thr Lys Gly Pro
            130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
                195                 200                 205

Val Pro Ser Ser Asn Phe Gly Thr Gln Thr Tyr Thr Cys Asn Val Asp
                210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Gln His His His His
                260                 265                 270

His

<210> SEQ ID NO 171
<211> LENGTH: 274
<212> TYPE: PRT
<213> ORGANISM: homosapiens

<400> SEQUENCE: 171

Met Glu Phe Gly Leu Ser Trp Val Phe Leu Val Ala Leu Leu Arg Gly
1               5                   10                  15

Val Gln Cys Gln Val Gln Met Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Ile Phe Gly Ile His Trp Val Arg Gln Ser Pro Gly Lys Gly Leu
    50                  55                  60

Glu Cys Leu Ala Val Ile Ser Asn Asp Gly Ser Lys Glu Tyr Tyr Ala
65                  70                  75                  80

Gly Ser Val Lys Gly Arg Ile Thr Ile Ser Arg Asp Asn Ala Lys Asn
                85                  90                  95

Met Val Tyr Leu Gln Met Asn Gly Leu Arg Ala Glu Asp Thr Ala Val
                100                 105                 110

Tyr Tyr Cys Val Arg Asp Asn Pro Asp Gly Tyr Asn His Phe Asp His
                115                 120                 125

Trp Gly Gln Gly Thr Leu Val Thr Val Ser Ser Ala Ser Thr Lys Gly
            130                 135                 140

Pro Ser Val Phe Pro Leu Ala Pro Cys Ser Arg Ser Thr Ser Glu Ser
145                 150                 155                 160

Thr Ala Thr Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
            195                 200                 205

Thr Val Pro Ser Ser Asn Phe Gly Thr Gln Thr Tyr Thr Cys Asn Val
210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Val Ala Gly Pro
            245                 250                 255

Ser Val Phe Leu Phe Pro Pro Lys Pro Lys Asp Thr His His His
            260                 265                 270

His His

<210> SEQ ID NO 172
<211> LENGTH: 277
<212> TYPE: PRT
<213> ORGANISM: homosapiens

<400> SEQUENCE: 172

Met Glu Phe Gly Leu Ser Trp Val Phe Leu Val Ala Leu Leu Arg Gly
1               5                   10                  15

Val Gln Cys Gln Ala His Leu Val Glu Ser Gly Gly Gly Val Val Gln
                20                  25                  30

Pro Gly Arg Ser Leu Arg Leu Ser Cys Ala Ala Ser Thr Phe Ser Phe
            35                  40                  45

Ser Ser Tyr Ala Met His Trp Val Arg Gln Ala Pro Gly Lys Gly Leu
50                  55                  60

Glu Trp Val Ala Gly Ile Ser Ser Asp Gly Ser Asp Gln Arg His Ala
65                  70                  75                  80

Asp Ser Val Thr Gly Arg Phe Thr Ile Ser Arg Asp Asn Ser Lys Ser
                85                  90                  95

Thr Leu Phe Leu Gln Met Ser Ser Leu Thr Val Glu Asp Thr Gly Leu
            100                 105                 110

Tyr Tyr Cys Val Arg Ser Gln Gln Pro Gln Arg Phe Asp Trp Leu Leu
        115                 120                 125

Ser Glu Tyr Trp Gly Gln Gly Thr Leu Val Thr Val Ser Ser Ala Ser
130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Val
                245                 250                 255

Ala Gly Pro Ser Val Phe Leu Phe Pro Pro Lys Pro Lys Asp Thr His
            260                 265                 270

His His His His His
        275

<210> SEQ ID NO 173
<211> LENGTH: 275

<212> TYPE: PRT
<213> ORGANISM: homosapiens

<400> SEQUENCE: 173

Met Glu Phe Gly Leu Ser Trp Val Phe Leu Val Ala Ile Leu Glu Gly
1               5                   10                  15

Val Arg Cys Glu Val Gln Leu Val Glu Ser Gly Gly Asp Leu Val Lys
            20                  25                  30

Pro Gly Gly Ser Leu Arg Leu Ser Cys Ala Ala Ser Gly Phe Ile Phe
        35                  40                  45

Ser Asp Tyr Tyr Met Ser Trp Ile Arg Gln Ala Pro Gly Lys Gly Leu
    50                  55                  60

Glu Trp Val Ser Cys Ile Ser Ser Ser Gly Ser Ile Ile Tyr Asp Ala
65                  70                  75                  80

Asp Ser Val Lys Gly Arg Phe Thr Ile Ser Arg Asp Asn Ser Lys Asn
                85                  90                  95

Ser Val Tyr Leu Gln Leu Asn Ser Leu Arg Ala Glu Asp Thr Ala Val
            100                 105                 110

Tyr Tyr Cys Ala Arg Pro Val Val Pro Ala Ser Asp Ala Phe Asp
        115                 120                 125

Thr Trp Gly Gln Gly Thr Met Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Val Ala Gly
                245                 250                 255

Pro Ser Val Phe Leu Phe Pro Pro Lys Pro Lys Asp Pro His His His
            260                 265                 270

His His His
        275

<210> SEQ ID NO 174
<211> LENGTH: 285
<212> TYPE: PRT
<213> ORGANISM: homosapiens

<400> SEQUENCE: 174

Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Leu Val Lys
            20                  25                  30

Pro Gly Gly Ser Leu Ile Leu Ser Cys Ala Ala Ser Gly Phe Thr Phe
        35                  40                  45

Ser Asp Tyr Tyr Met Gly Trp Ile Arg Gln Ala Pro Gly Asn Gly Leu
    50                  55                  60

Glu Cys Ile Ser Tyr Ile Ser Gly Ser Gly Ile Asp Thr His Tyr Thr
65                  70                  75                  80

Asp Ser Val Lys Gly Arg Phe Thr Ile Ser Arg Asp Asn Ala Met Asn
                85                  90                  95

Ser Leu Tyr Leu Gln Met Asn Ser Leu Arg Ala Asp Asp Thr Ala Val
            100                 105                 110

Tyr Tyr Cys Ala Arg Leu Pro Pro His Cys Thr Asn Asn Ile Cys Pro
            115                 120                 125

Val Leu Gly Asp Tyr Phe Tyr Gly Met Asp Val Trp Gly Gln Gly Thr
        130                 135                 140

Thr Val Thr Val Ser Ser Ala Ser Thr Lys Gly Pro Ser Val Phe Pro
145                 150                 155                 160

Leu Ala Pro Cys Ser Arg Ser Thr Ser Glu Ser Thr Ala Ala Leu Gly
                165                 170                 175

Cys Leu Val Lys Asp Tyr Phe Pro Glu Pro Val Thr Val Ser Trp Asn
            180                 185                 190

Ser Gly Ala Leu Thr Ser Gly Val His Thr Phe Pro Ala Val Leu Gln
        195                 200                 205

Ser Ser Gly Leu Tyr Ser Leu Ser Ser Val Val Thr Val Pro Ser Ser
210                 215                 220

Asn Phe Gly Thr Gln Thr Tyr Thr Cys Asn Val Asp His Lys Pro Ser
225                 230                 235                 240

Asn Thr Lys Val Asp Lys Thr Val Glu Arg Lys Cys Cys Val Glu Cys
                245                 250                 255

Pro Pro Cys Pro Ala Pro Pro Val Ala Gly Pro Ser Val Phe Leu Phe
            260                 265                 270

Pro Pro Lys Pro Lys Asp Thr His His His His His His
        275                 280                 285

<210> SEQ ID NO 175
<211> LENGTH: 271
<212> TYPE: PRT
<213> ORGANISM: homosapiens

<400> SEQUENCE: 175

Met Glu Leu Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Lys Ser Leu Arg Leu Ser Cys Ala Val Ser Gly Phe Asn Phe
        35                  40                  45

Ser Ala Tyr Gly Met His Trp Val Arg Gln Ala Pro Gly Lys Gly Leu
    50                  55                  60

Glu Trp Val Ala Val Val Trp His Asp Glu Ile Asn Lys Ile Tyr Ala
65                  70                  75                  80

Asp Ser Val Lys Gly Arg Phe Ser Ile Ser Arg Asp Asn Ser Glu Asn
                85                  90                  95

Val Met Tyr Leu Gln Met Asn Ser Leu Arg Val Glu Asp Thr Gly Leu
            100                 105                 110

Tyr Phe Cys Val Arg Asp Gln Asn Tyr Ile Phe Asp Phe Trp Gly Gln
            115                 120                 125

Gly Thr Val Val Thr Val Ser Ser Ala Ser Thr Lys Gly Pro Ser Val
        130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
            165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
            195                 200                 205

Ser Ser Asn Phe Gly Thr Gln Thr Tyr Thr Cys Asn Val Asp His Lys
        210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr His His His His His His
            260                 265                 270

<210> SEQ ID NO 176
<211> LENGTH: 282
<212> TYPE: PRT
<213> ORGANISM: homosapiens

<400> SEQUENCE: 176

Met Glu Phe Gly Leu Ser Trp Val Phe Leu Val Ala Ile Leu Lys Gly
1               5                   10                  15

Val Gln Cys Glu Ile Glu Val Arg Glu Ser Gly Gly Gly Leu Val Lys
            20                  25                  30

Pro Gly Arg Ser Leu Arg Leu Ser Cys Thr Thr Ser Gly Phe Arg Phe
            35                  40                  45

Arg Asp Tyr Ala Ile Ser Trp Phe Arg Gln Ala Pro Gly Lys Gly Leu
        50                  55                  60

Glu Trp Val Gly Leu Ile Arg Ala Arg Ile Tyr Gly Gly Thr Thr Asp
65                  70                  75                  80

Phe Ala Ala Ala Val Arg Gly Arg Phe Ile Ile Ser Arg Asp Asp Ser
                85                  90                  95

Gln Asn Val Ala Tyr Leu Gln Met Ala Ser Leu Glu Ala Glu Asp Thr
            100                 105                 110

Ala Ile Tyr Tyr Cys Thr Arg Val Gly Leu Asn Asp Leu Ile Ala Ala
            115                 120                 125

Gly Ser Met Tyr Ser Phe Asp His Trp Gly Gln Gly Thr Leu Val Ile
        130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
            195                 200                 205

Leu Tyr Ser Leu Ser Ser Val Val Thr Val Pro Ser Ser Asn Phe Gly
        210                 215                 220

Thr Gln Thr Tyr Thr Cys Asn Val Asp His Lys Pro Ser Asn Thr Lys
225                 230                 235                 240

Val Asp Lys Thr Val Glu Arg Lys Cys Cys Val Glu Cys Pro Pro Cys
                245                 250                 255

Pro Ala Pro Pro Val Ala Gly Pro Ser Val Phe Leu Phe Pro Pro Lys

```
                    260                 265                 270
Pro Lys Asp Thr Asp Tyr His His His His
        275                 280

<210> SEQ ID NO 177
<211> LENGTH: 274
<212> TYPE: PRT
<213> ORGANISM: homosapiens

<400> SEQUENCE: 177

Met Glu Phe Gly Leu Ser Trp Val Phe Leu Val Ala Leu Leu Arg Gly
1               5                   10                  15

Val Gln Cys Glu Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser His Ala Met His Trp Val Arg Gln Ala Pro Gly Lys Gly Leu
    50                  55                  60

Glu Trp Val Thr Cys Ile Ser Tyr Asp Gly Asn Tyr Glu Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asp Ser Leu Arg Ile Glu Asp Thr Ala Met
            100                 105                 110

Tyr Tyr Cys Ala Arg Gly Thr Gly Glu Gln Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr His His His His
            260                 265                 270

His His

<210> SEQ ID NO 178
<211> LENGTH: 275
<212> TYPE: PRT
<213> ORGANISM: homosapiens

<400> SEQUENCE: 178

Met Glu Phe Gly Leu Ser Trp Val Phe Leu Val Ala Leu Leu Arg Gly
1               5                   10                  15

Val Gln Cys Gln Val Gln Leu Met Glu Ser Gly Gly Gly Val Val Gln
            20                  25                  30
```

-continued

```
Pro Gly Gly Ser Leu Arg Leu Ser Cys Ala Ala Ser Gly Phe Asn Phe
            35                  40                  45

Asn Tyr Phe Pro Met His Trp Val Arg Gln Ala Pro Gly Lys Gly Leu
 50                  55                  60

Glu Trp Leu Ala Val Ile Leu Asp His Glu Arg Gly Arg Tyr Tyr Ala
 65                  70                  75                  80

Asp Ser Val Lys Gly Arg Phe Ile Ile Phe Arg Asp Ile Ser Arg Ser
                 85                  90                  95

Thr Leu His Leu Gln Met Asp Ala Leu Arg Pro Asp Asp Ser Ala Leu
                100                 105                 110

Tyr Tyr Cys Ala Arg Glu Thr Arg Pro Asn Gly Asp Ser Ala Cys Asp
                115                 120                 125

Ser Trp Gly Gln Gly Thr Arg Val Thr Val Ser Ala Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr His His His
                260                 265                 270

His His His
    275

<210> SEQ ID NO 179
<211> LENGTH: 272
<212> TYPE: PRT
<213> ORGANISM: homosapiens

<400> SEQUENCE: 179

Met Glu Phe Glu Leu Ser Trp Val Phe Leu Val Ala Leu Leu Arg Gly
 1               5                  10                  15

Val Gln Cys Gln Val Gln Val Val Glu Ser Gly Gly Gly Val Val Gln
                 20                  25                  30

Pro Gly Arg Ser Leu Arg Leu Ser Cys Ala Ala Ser Gly Phe Thr Leu
            35                  40                  45

Pro Asn Tyr Ala Met Gln Trp Val Arg Gln Ala Pro Gly Lys Gly Leu
 50                  55                  60

Glu Trp Val Ala Ile Ile Leu His Asp Gly Ser Arg Glu Tyr Tyr Gly
 65                  70                  75                  80

Glu Ser Val Lys Gly Arg Phe Thr Ile Ser Arg Asp Thr Ser Lys Asn
                 85                  90                  95

Thr Val Tyr Leu Gln Ile Ser Ser Leu Arg Ala Glu Asp Thr Ala Val
                100                 105                 110

Tyr Tyr Cys Ala Arg Glu Arg Thr Gly Tyr Tyr Leu Glu Gln Trp Gly
```

```
            115                 120                 125
Gln Gly Thr Leu Val Thr Val Ser Ser Ala Ser Thr Lys Gly Pro Ser
        130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr His His His His His His
            260                 265                 270

<210> SEQ ID NO 180
<211> LENGTH: 282
<212> TYPE: PRT
<213> ORGANISM: homosapiens

<400> SEQUENCE: 180

Met Glu Phe Gly Leu Ser Trp Val Phe Leu Val Ala Ile Leu Glu Gly
1               5                   10                  15

Val Gln Cys Glu Val Gln Leu Val Glu Ser Gly Gly Ala Val Val Gln
            20                  25                  30

Pro Gly Gly Ser Leu Arg Leu Ser Cys Ala Ala Ser Gly Phe Thr Phe
        35                  40                  45

Arg Asp His Asn Met Asn Trp Val Arg Gln Ala Pro Gly Gln Gly Leu
    50                  55                  60

Glu Trp Val Ser Leu Ile Asn Ser His Gly Ser Asp Thr Phe Tyr Thr
65                  70                  75                  80

Asp Ser Val Lys Gly Arg Phe Thr Ile Ser Arg Asp Asn Ser Lys Asn
                85                  90                  95

Ser Leu Tyr Leu Gln Met Asn Ser Leu Arg Pro Glu Asp Thr Ser Phe
            100                 105                 110

Tyr Tyr Cys Val Lys Asp Gly Gly Tyr Cys Arg Gly Gly Ser Cys His
        115                 120                 125

Trp Glu Gly Ile Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
    210                 215                 220
```

```
Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr His His His His His His His
            275                 280
```

<210> SEQ ID NO 181
<211> LENGTH: 279
<212> TYPE: PRT
<213> ORGANISM: homosapiens

<400> SEQUENCE: 181

```
Met Val Phe Gly Leu Ser Trp Leu Phe Leu Val Ala Ile Leu Lys Gly
1               5                   10                  15

Val Arg Cys Glu Val Gln Leu Val Gly Ser Gly Gly Gly Leu Val Lys
                20                  25                  30

Pro Gly Glu Ser Leu Arg Leu Ser Cys Ala Ala Ser Gly Phe Thr Phe
            35                  40                  45

Ser Asn Tyr Ala Met Asn Trp Val Arg Gln Ala Ala Gly Lys Arg Pro
50                  55                  60

Glu Trp Val Ser Ile Ile Thr Gly Ser Gly Ala Asp Thr Tyr Tyr Pro
65                  70                  75                  80

Gln Ser Met Arg Gly Arg Phe Thr Ile Ser Arg Asp Asn Ser Gln Asn
                85                  90                  95

Thr Val Tyr Leu Gln Met Asn Ser Leu Arg Val Glu Asp Thr Ala Val
            100                 105                 110

Tyr Tyr Cys Ala Lys Gly Thr Gln Phe Ser Cys Ser Ser Thr Arg Cys
        115                 120                 125

Tyr Pro Leu Asp Tyr Trp Gly Gln Gly Thr Leu Val Thr Val Ser Ser
130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr His His His His His His
        275
```

<210> SEQ ID NO 182
<211> LENGTH: 274
<212> TYPE: PRT
<213> ORGANISM: homosapiens

<400> SEQUENCE: 182

```
Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Asn Trp Val Arg Gln Ala Pro Gly Lys Gly Leu
    50                  55                  60

Glu Trp Val Ser Phe Ile Ser Gly Ser Ala Lys Thr Phe Tyr Ala
65                  70                  75                  80

Asp Ser Val Lys Gly Arg Phe Thr Ile Ser Arg Asp Asn Ser Lys Asp
                85                  90                  95

Thr Leu Tyr Leu Gln Met Asn Ser Leu Arg Ala Asp Asp Thr Ala Val
            100                 105                 110

Tyr Phe Cys Ala Lys Met Thr Thr Val Val Leu Glu Ser Ile Asp Ser
        115                 120                 125

Trp Gly Gln Gly Thr Leu Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr His His His His
            260                 265                 270

His His
```

<210> SEQ ID NO 183
<211> LENGTH: 282
<212> TYPE: PRT
<213> ORGANISM: homosapiens

<400> SEQUENCE: 183

```
Met Glu Phe Gly Leu Ser Trp Val Phe Leu Val Ala Ile Leu Glu Gly
1               5                   10                  15

Val Gln Cys Glu Val Gln Leu Val Glu Ser Gly Gly Asp Leu Val Gln
            20                  25                  30

Pro Gly Gly Ser Leu Arg Leu Ser Cys Ala Ala Ser Gly Phe Thr Phe
        35                  40                  45

Gly Asn Tyr Trp Met Asn Trp Val Arg Gln Ala Pro Gly Lys Gly Leu
    50                  55                  60

Glu Trp Val Ala Asn Ile Asn Lys Asp Gly Ser Asp Lys Phe Tyr Ala
65                  70                  75                  80
```

-continued

```
Asp Ser Val Glu Gly Arg Phe Thr Ile Ser Arg Asp Asn Ala Glu Asn
                85                  90                  95

Ser Leu Tyr Leu Gln Met Asn Ser Leu Arg Val Glu Asp Thr Ala Val
            100                 105                 110

Tyr Tyr Cys Ala Arg Pro Leu Glu Trp Phe Gly Glu Leu Ile Ser Gly
        115                 120                 125

Trp Phe Asp Pro Trp Gly Arg Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Asn His His His His
        275                 280

<210> SEQ ID NO 184
<211> LENGTH: 273
<212> TYPE: PRT
<213> ORGANISM: homosapiens

<400> SEQUENCE: 184

Met Glu Phe Gly Leu Ser Trp Ile Leu Leu Val Ala Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Ser Val
        35                  40                  45

Gly Asp Val Trp Met Ser Trp Val Arg Gln Ala Pro Gly Lys Gly Leu
    50                  55                  60

Glu Trp Val Gly Arg Ile His Ser Lys Ala Asp Ala Gly Thr Ile Asp
65                  70                  75                  80

Tyr Asn Thr Pro Val Lys Gly Arg Phe Thr Met Ser Arg Asp Asp Ser
                85                  90                  95

Thr Asn Thr Leu Tyr Leu Gln Met Asn Ser Leu Lys Ser Glu Asp Thr
            100                 105                 110

Gly Val Tyr Tyr Cys Thr Arg Arg Ser Ser Met Gly Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175
```

```
Ser Gly Ala Leu Thr Ser Gly Val His Thr Phe Pro Ala Val Leu Gln
            180                 185                 190

Ser Ser Gly Leu Tyr Ser Leu Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr His His His His
            260                 265                 270

His

<210> SEQ ID NO 185
<211> LENGTH: 283
<212> TYPE: PRT
<213> ORGANISM: homosapiens

<400> SEQUENCE: 185

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Leu Val Gln
            20                  25                  30

Pro Gly Gly Ser Leu Arg Leu Ser Cys Ala Pro Ser Gly Phe Thr Phe
        35                  40                  45

Asp Asp Tyr Trp Met His Trp Val Arg Gln Ala Pro Gly Lys Gly Leu
    50                  55                  60

Val Trp Val Ser Arg Ile Ser Pro Asp Gly Ser Gly Thr Thr Tyr Ala
65                  70                  75                  80

Asp Ser Val Lys Gly Arg Phe Thr Ile Ser Arg Asp Asn Ala Lys Asn
                85                  90                  95

Thr Val Phe Leu Gln Met Asn Ser Leu Arg Val Glu Asp Thr Ala Val
            100                 105                 110

Tyr Tyr Cys Val Arg Asp Ile Gly Ile Gly Ser Ser Tyr Gly Trp Gln
        115                 120                 125

Lys Trp Phe Asp Pro Trp Gly Gln Gly Thr Gln Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270
```

Lys Pro Lys Asp Thr His His His His His
            275                 280

<210> SEQ ID NO 186
<211> LENGTH: 289
<212> TYPE: PRT
<213> ORGANISM: homosapiens

<400> SEQUENCE: 186

Met Lys Leu Trp Arg Lys Val Pro Ala Ala Asp Lys Ala Pro Tyr Leu
1               5                   10                  15

Gln Lys Ala Lys Asp Asn Arg Ala Ala His Arg Ile Asn Lys Val Gln
            20                  25                  30

Lys Val Glu Tyr Gly Gly Gly Leu Ala Gln Pro Gly Gly Ser Leu Arg
        35                  40                  45

Leu Ser Cys Ala Ala Ser Gly Phe Ser Phe Ser Asp Tyr Asp Met Thr
    50                  55                  60

Trp Val Arg Gln Ala Pro Gly Lys Gly Leu Glu Trp Val Ser Tyr Ile
65                  70                  75                  80

Ser Ser Gly Gly Ser Ala Ile Ser Tyr Ala Asp Ser Val Arg Gly Arg
                85                  90                  95

Phe Thr Ile Ser Arg Asp Asn Ala Lys Asn Ala Leu Phe Leu Gln Met
            100                 105                 110

Asn Ser Leu Arg Ala Glu Asp Thr Ala Val Tyr Phe Cys Ala Arg Arg
        115                 120                 125

Lys Arg Trp Asp Ser Ser Gly Ser Leu Asp Tyr Trp Gly Gln Gly Thr
    130                 135                 140

Leu Val Thr Val Ser Ser Ala Ser Thr Lys Gly Pro Ser Val Phe Pro
145                 150                 155                 160

Leu Ala Pro Ser Ser Lys Ser Thr Ser Gly Gly Thr Ala Ala Leu Gly
                165                 170                 175

Cys Leu Val Lys Asp Tyr Phe Pro Glu Pro Val Thr Val Ser Trp Asn
            180                 185                 190

Ser Gly Ala Leu Thr Ser Gly Val His Thr Phe Pro Ala Val Leu Gln
        195                 200                 205

Ser Ser Gly Leu Tyr Ser Leu Ser Ser Val Val Thr Val Pro Ser Ser
    210                 215                 220

Ser Leu Gly Thr Gln Thr Tyr Ile Cys Asn Val Asn His Lys Pro Ser
225                 230                 235                 240

Asn Thr Lys Val Asp Lys Lys Val Glu Pro Lys Ser Cys Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr His His His His His
        275                 280                 285

His

<210> SEQ ID NO 187
<211> LENGTH: 278
<212> TYPE: PRT
<213> ORGANISM: homosapiens

<400> SEQUENCE: 187

Met Glu Phe Gly Leu Ser Trp Val Phe Leu Val Ala Leu Leu Arg Gly
1               5                   10                  15

-continued

Val His Cys Gln Val Gln Leu Val Glu Ser Gly Gly Val Val Gln
            20                  25                  30

Pro Gly Ser Ser Leu Arg Leu Ser Cys Val Gly Ser Gly Phe Thr Phe
            35                  40                  45

Arg Ser Tyr Ala Met His Trp Val Arg Gln Ala Pro Gly Lys Gly Leu
    50                  55                  60

Asp Trp Val Ala Val Ile Ser Tyr His Gly Arg Asp Lys Tyr Tyr Ala
65                  70                  75                  80

Asp Ser Val Lys Gly Arg Phe Thr Ile Ser Arg Val Asn Ser Lys Asn
                85                  90                  95

Thr Leu Tyr Leu Gln Met Asn Ser Leu Arg Ala Gly Asp Thr Ala Val
            100                 105                 110

Tyr Tyr Cys Ala Arg Asp Arg Gly Asp Tyr Gly Gly Pro Ile Pro Gly
            115                 120                 125

Ala Phe Asp Ile Trp Gly Gln Gly Thr Thr Val Thr Val Ser Ser Ala
            130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Asn Phe Gly Thr Gln Thr Tyr
        210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

His His His His His His
        275

<210> SEQ ID NO 188
<211> LENGTH: 274
<212> TYPE: PRT
<213> ORGANISM: homosapiens

<400> SEQUENCE: 188

Met Glu Phe Gly Leu Ser Trp Ile Phe Leu Leu Ala Thr Leu Lys Gly
1               5                   10                  15

Val Gln Cys Glu Val Gln Leu Val Glu Ser Gly Gly Gly Leu Ala Gln
            20                  25                  30

Pro Gly Gly Ser Leu Arg Leu Ser Cys Ala Val Ser Gly Phe Asn Phe
            35                  40                  45

Gly Asp His Asp Met His Trp Val Arg Gln Pro Pro Gly Lys Gly Leu
    50                  55                  60

Gln Trp Val Ala Ser Ile Ser Glu Asn Gly Tyr Thr Ile Lys Tyr Ser
65                  70                  75                  80

Asp Ser Val Lys Gly Arg Phe Thr Ile Ser Arg Asp Asn Ala Met Asn
                85                  90                  95

Ser Leu Tyr Leu His Leu Asn Ser Leu Arg Ser Glu Asp Thr Ala Ser
            100                 105                 110

Tyr Tyr Cys Ala Lys Ile Pro Tyr Gly Ser Glu Asn Phe Phe Asp Tyr
            115                 120                 125

Trp Gly Gln Gly Ala Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Cys Ser Leu Ser Ser Val Val
            195                 200                 205

Thr Val Pro Ser Ser Asn Phe Gly Thr Gln Thr Tyr Thr Cys Asn Val
210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr His His His His
            260                 265                 270

His His

<210> SEQ ID NO 189
<211> LENGTH: 271
<212> TYPE: PRT
<213> ORGANISM: homosapiens

<400> SEQUENCE: 189

Met Glu Phe Gly Leu Ser Trp Val Phe Leu Val Ala Ile Phe Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Pro Gly Tyr Met Phe
        35                  40                  45

Thr Asn Leu Trp Met Ser Trp Val Arg Gln Ala Pro Gly Lys Gly Leu
50                  55                  60

Glu Trp Val Ala Asn Ile Asn Gln Asp Gly Ser Val Lys His Ser Val
65                  70                  75                  80

Asp Ser Val Arg Gly Arg Phe Thr Ile Ser Arg Asp Asn Val Lys Asn
                85                  90                  95

Ser Leu Tyr Leu Gln Met Asn Ser Leu Arg Ala Glu Asp Thr Ala Val
            100                 105                 110

Tyr Tyr Cys Ala Thr Ser Ile Asp Ala Ala Gly Thr Asp Trp Gly Gln
            115                 120                 125

Gly Thr Leu Val Thr Val Ser Ser Ala Ser Thr Lys Gly Pro Ser Val
        130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
        210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Val Ala Gly Pro Ser Val Phe
                245                 250                 255

Leu Phe Pro Pro Lys Pro Lys Asp Thr His His His His His His
            260                 265                 270

<210> SEQ ID NO 190
<211> LENGTH: 273
<212> TYPE: PRT
<213> ORGANISM: homosapiens

<400> SEQUENCE: 190

Met Glu Phe Gly Leu Ser Trp Ile Phe Leu Ala Ala Thr Leu Lys Gly
1               5                   10                  15

Val Gln Cys Glu Val Gln Leu Val Glu Ser Gly Gly Gly Leu Val Lys
            20                  25                  30

Pro Ala Gly Ser Leu Arg Leu Ser Cys Glu Ala Ser Gly Phe Ala Phe
        35                  40                  45

Ser Asn Val Trp Met Thr Trp Val Arg Gln Ala Pro Gly Lys Gly Leu
    50                  55                  60

Glu Trp Val Gly Arg Ile Thr Thr Lys Ala Asp Asn Trp Gly Thr Asp
65                  70                  75                  80

Tyr Ala Ala Pro Leu Arg Gly Arg Phe Thr Ile Ser Arg Asp Asp Ser
                85                  90                  95

Lys Asn Thr Leu Tyr Leu Gln Met Asn Ser Leu Lys Thr Glu Asp Thr
            100                 105                 110

Ala Ala Tyr Tyr Cys Ala Ile Leu Asn Arg Gly Arg Phe Glu Ser Trp
        115                 120                 125

Gly Gln Gly Thr Leu Val Thr Val Ser Ser Ala Ser Thr Asn Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Val Ala Gly Pro Ser
                245                 250                 255

Val Phe Leu Phe Pro Pro Lys Pro Lys Asp Thr His His His His His
            260                 265                 270

His

<210> SEQ ID NO 191
<211> LENGTH: 282
<212> TYPE: PRT
<213> ORGANISM: homosapiens

<400> SEQUENCE: 191

```
Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Phe
        35                  40                  45

Ser Lys Phe Trp Met His Trp Val Arg Gln Leu Pro Gly Lys Gly Leu
    50                  55                  60

Val Trp Val Ser Arg Ile Asn Arg Asp Gly Ser Gly Thr Arg Tyr Val
65                  70                  75                  80

Asp Ser Val Arg Gly Arg Ile Thr Ile Ser Arg Asp Asn Ala Lys Asn
                85                  90                  95

Thr Leu Tyr Leu Gln Met Asn Ser Leu Arg Ala Glu Asp Thr Gly Val
            100                 105                 110

Tyr His Cys Ala Arg Gly Tyr Tyr Gly Ser Gly Lys Phe Gly Pro
        115                 120                 125

Gly Asp Tyr Tyr Gly Leu Asp Val Trp Gly Gln Gly Thr Thr Val Thr
    130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Asn Phe Gly
    210                 215                 220

Thr Gln Thr Tyr Thr Cys Asn Val Asp His Lys Pro Ser Asn Thr Lys
225                 230                 235                 240

Val Asp Lys Thr Val Glu Arg Lys Cys Cys Val Glu Cys Pro Pro Cys
                245                 250                 255

Pro Ala Pro Pro Val Ala Gly Pro Ser Val Phe Leu Phe Pro Pro Lys
            260                 265                 270

Pro Lys Asp Thr His His His His His His
        275                 280
```

<210> SEQ ID NO 192
<211> LENGTH: 277
<212> TYPE: PRT
<213> ORGANISM: homosapiens

<400> SEQUENCE: 192

```
Met Glu Phe Gly Leu Ser Trp Val Phe Leu Val Ala Leu Leu Arg Gly
1               5                   10                  15

Val Gln Cys Gln Val Leu Leu Val Gln Ser Gly Gly Gly Val Val Gln
            20                  25                  30

Pro Gly Arg Ser Leu Arg Leu Ser Cys Ala Gly Ser Gly Phe Ser Phe
        35                  40                  45

Ser Asn Tyr Ala Ile His Trp Val Arg Gln Ala Pro Gly Lys Gly Leu
    50                  55                  60

Glu Trp Val Ala Gly Ile Ser Ser Asn Gly Ile Asp Lys Ile Tyr Thr
65                  70                  75                  80
```

```
Asp Ser Leu Glu Gly Arg Phe Ala Ile Ser Arg Asp Asn Phe Lys Asp
                85                  90                  95

Thr Leu Tyr Leu Gln Met Asn Ser Leu Arg Leu Glu Asp Thr Ala Val
            100                 105                 110

Tyr Tyr Cys Val Arg Ser Arg Asp Pro Ser Ala Phe Asp Trp Leu Phe
        115                 120                 125

Ser Asp Tyr Trp Gly Gln Gly Ala Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr His
            260                 265                 270

His His His His His
        275

<210> SEQ ID NO 193
<211> LENGTH: 274
<212> TYPE: PRT
<213> ORGANISM: homosapiens

<400> SEQUENCE: 193

Met Glu Phe Gly Leu Ser Trp Val Phe Leu Ala Ala Ile Leu Lys Gly
1               5                   10                  15

Val Gln Cys Asp Val Gln Leu Val Glu Ser Gly Gly Gly Leu Val Gln
            20                  25                  30

Pro Gly Gly Ser Leu Ile Leu Ser Cys Val Ala Ser Gly Phe Thr Phe
        35                  40                  45

Ser Ser His Trp Met Tyr Trp Val Arg Gln Ala Pro Gly Lys Gly Leu
    50                  55                  60

Val Trp Val Ser Val Ile Gly Tyr Asp Gly Ser Ser Lys Ile Tyr Ala
65                  70                  75                  80

Asp Ser Val Lys Gly Arg Phe Thr Ile Ser Arg Asp Asn Ala Lys Asn
                85                  90                  95

Thr Leu His Leu Glu Met Asn Asn Val Lys Asp Glu Asp Ser Ala Val
            100                 105                 110

Tyr Tyr Cys Ala Arg Gly Gly Tyr Asp His Ala Leu Asp Tyr Trp Gly
        115                 120                 125

Gln Gly Thr Leu Val Ala Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
```

```
            165                 170                 175
Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Asn Phe Gly Thr Gln Thr Tyr Thr Cys Asn Val Asp His
            210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
            245                 250                 255

Phe Leu Phe Pro Pro Lys Pro Lys Asp Thr His His His His His His
            260                 265                 270

His His

<210> SEQ ID NO 194
<211> LENGTH: 275
<212> TYPE: PRT
<213> ORGANISM: homosapiens

<400> SEQUENCE: 194

Met Glu Phe Gly Leu Ser Trp Val Phe Leu Leu Ala Ile Leu Lys Gly
1               5                   10                  15

Val Gln Cys Lys Val Gln Leu Val Glu Ser Gly Gly Gly Leu Val Gln
            20                  25                  30

Pro Gly Gly Ser Leu Arg Leu Ser Cys Gly Ala Ser Gly Phe Thr Phe
            35                  40                  45

Ser Thr Tyr Trp Met His Trp Val Arg Gln Ser Pro Glu Lys Gly Leu
        50                  55                  60

Val Trp Val Ser Arg Ile Asn His Glu Gly Thr Ser Thr Arg Tyr Ala
65                  70                  75                  80

Asp Ser Val Lys Gly Arg Phe Thr Val Ser Arg Asp Asn Ala Lys Asn
                85                  90                  95

Thr Val Tyr Leu Gln Met Asn Ser Leu Arg Val Asp Asp Thr Ala Val
            100                 105                 110

Tyr Tyr Cys Ala Arg Asp Leu Gly Glu Ser Thr Pro Leu Asp Pro Trp
        115                 120                 125

Gly Gln Gly Thr Leu Val Ile Val Ser Ser Ala Ser Thr Lys Gly Pro
130                 135                 140

Ser Val Phe Pro Leu Ala Ser Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr His His His His His
```

His His His
    275

<210> SEQ ID NO 195
<211> LENGTH: 230
<212> TYPE: PRT
<213> ORGANISM: homosapiens

<400> SEQUENCE: 195

Met His Trp Val Arg Gln Ala Pro Gly Lys Gly Leu Asp Trp Val Ala
1               5                   10                  15

Leu Leu Ser His Asp Gly Ser His Glu Tyr Tyr Ala Asp Ser Val Lys
            20                  25                  30

Gly Arg Phe Thr Ile Ser Arg Asp Asn Ser Lys Asn Arg Leu Tyr Leu
        35                  40                  45

Gln Met Asn Ser Leu Arg Val Glu Asp Thr Ala Val Tyr Tyr Cys Thr
    50                  55                  60

Arg Val Ala Tyr Ser Phe Glu Phe Gly Asn Gly Phe Asp Pro Trp Gly
65                  70                  75                  80

Gln Gly Thr Leu Val Thr Val Ser Ser Ala Ser Thr Lys Gly Pro Ser
                85                  90                  95

Val Phe Pro Leu Ala Pro Ser Ser Lys Ser Thr Ser Gly Gly Thr Ala
            100                 105                 110

Ala Leu Gly Cys Leu Val Lys Asp Tyr Phe Pro Glu Pro Val Thr Val
        115                 120                 125

Ser Trp Asn Ser Gly Ala Leu Thr Ser Gly Val His Thr Phe Pro Ala
    130                 135                 140

Val Leu Gln Ser Ser Gly Leu Tyr Ser Leu Ser Ser Val Val Thr Val
145                 150                 155                 160

Pro Ser Ser Ser Leu Gly Thr Gln Thr Tyr Ile Cys Asn Val Asn His
                165                 170                 175

Lys Pro Ser Asn Thr Lys Val Asp Lys Lys Val Glu Pro Lys Ser Cys
            180                 185                 190

Asp Lys Thr His Thr Cys Pro Pro Cys Pro Ala Pro Glu Leu Leu Gly
        195                 200                 205

Gly Pro Ser Val Phe Leu Phe Pro Pro Lys Pro Lys Asp Thr His His
    210                 215                 220

His His His His His His
225                 230

<210> SEQ ID NO 196
<211> LENGTH: 275
<212> TYPE: PRT
<213> ORGANISM: homosapiens

<400> SEQUENCE: 196

Met Glu Phe Gly Leu Ser Trp Val Phe Leu Val Ala Leu Leu Arg Gly
1               5                   10                  15

Val His Cys Gln Val Gln Leu Val Glu Ser Gly Gly Gly Val Val Gln
            20                  25                  30

Pro Gly Arg Ser Leu Arg Leu Ser Cys Gly Ala Ser Gly Phe Thr Phe
        35                  40                  45

Ser Asn Tyr Ala Met His Trp Val Arg Gln Phe Pro Gly Lys Gly Leu
    50                  55                  60

Asp Trp Val Ala Leu Ile Ser His Asp Ala Arg Glu Thr Tyr His Ala

```
                65                  70                  75                  80
        Glu Ser Val Ser Gly Arg Phe Thr Ile Ser Arg Asp Asn Ser Lys Asn
                            85                  90                  95

Thr Leu Phe Leu Glu Met Asn Ser Leu Arg Gly Glu Asp Thr Ala Val
                        100                 105                 110

Tyr Phe Cys Ala Arg Asp Gln Asp Ser Ser Gly Asp Thr Ala Leu Arg
                        115                 120                 125

Asp Trp Gly Gln Gly Thr Leu Val Thr Val Ser Ser Ala Ser Thr Lys
                130                 135                 140

Gly Pro Ser Val Phe Pro Leu Ala Pro Cys Ser Arg Ser Thr Ser Glu
        145                 150                 155                 160

Ser Thr Ala Ala Leu Gly Cys Leu Val Lys Asp Tyr Phe Pro Glu Pro
                        165                 170                 175

Val Thr Val Ser Trp Asn Ser Gly Ala Leu Thr Ser Gly Val His Thr
                        180                 185                 190

Phe Pro Ala Val Leu Gln Ser Ser Gly Leu Tyr Ser Leu Ser Ser Val
                        195                 200                 205

Val Thr Val Pro Ser Ser Asn Phe Gly Thr Gln Thr Tyr Thr Cys Asn
                210                 215                 220

Val Asp His Lys Pro Ser Asn Thr Lys Val Asp Lys Thr Val Glu Arg
        225                 230                 235                 240

Lys Cys Cys Val Glu Cys Pro Pro Cys Pro Ala Pro Pro Val Ala Gly
                        245                 250                 255

Pro Ser Val Phe Leu Phe Pro Pro Lys Pro Lys Asp Thr His His His
                        260                 265                 270

His His His
                275

<210> SEQ ID NO 197
<211> LENGTH: 278
<212> TYPE: PRT
<213> ORGANISM: homosapiens

<400> SEQUENCE: 197

Met Glu Phe Gly Leu Ser Trp Val Val Leu Val Ala Leu Leu Arg Gly
        1               5                   10                  15

Val Gln Cys Gln Val His Leu Gly Glu Ser Gly Gly Gly Val Val Gln
                        20                  25                  30

Pro Gly Gly Ser Leu Arg Leu Ser Cys Thr Ala Thr Gly Leu Gly Phe
                    35                  40                  45

Ser Thr Phe Ala Leu His Trp Ala Arg Gln Ala Pro Gly Gln Gly Leu
                50                  55                  60

Glu Trp Val Ala Gly Ile Ser Tyr Asp Glu Thr Arg Thr Ala Tyr Ala
        65                  70                  75                  80

Asp Ser Val Arg Gly Arg Phe Thr Ile Ser Arg Gly Asn Ser Lys Ala
                            85                  90                  95

Ser Leu Phe Leu Gln Met Asp Asp Leu Arg Pro Asp Thr Gly Val
                        100                 105                 110

Tyr Tyr Cys Thr Leu Ser Gln Thr Asn Glu Glu Tyr Asp Ile Leu Asn
                        115                 120                 125

Gly Leu Asp Tyr Trp Gly Gln Gly Val Leu Val Ala Val Ser Ser Ala
                130                 135                 140

Ser Thr Lys Gly Pro Ser Val Phe Pro Leu Ala Pro Cys Ser Arg Ser
        145                 150                 155                 160
```

```
Thr Ser Glu Ser Thr Ala Ala Leu Gly Cys Leu Val Lys Asp Tyr Phe
            165                 170                 175

Pro Glu Pro Val Thr Val Ser Trp Asn Ser Gly Ala Leu Thr Ser Gly
        180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Cys Pro Ala Pro Pro
                245                 250                 255

Val Ala Gly Pro Ser Val Phe Leu Phe Pro Pro Lys Pro Lys Asp Thr
        260                 265                 270

His His His His His His
        275

<210> SEQ ID NO 198
<211> LENGTH: 284
<212> TYPE: PRT
<213> ORGANISM: homosapiens

<400> SEQUENCE: 198

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Trp Met His Trp Val Arg Gln Ala Pro Gly Lys Gly Leu
    50                  55                  60

Val Trp Val Ser Arg Ile Asn Ser Asp Gly Ser Ser Ile Ser Tyr Ala
65              70                  75                  80

Asp Ala Val Lys Gly Arg Phe Thr Ile Ser Arg Asp Asn Ala Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Gly Ile Gly Gly Asn Ser Pro Asp Gly Pro
        115                 120                 125

Asp Ser Phe Tyr Tyr Gly Met Asp Val Trp Cys Gln Gly Thr Pro
    130                 135                 140

Val Thr Val Ser Ser Ala Ser Thr Lys Gly Pro Ser Val Phe Pro Leu
145                 150                 155                 160

Ala Pro Cys Ser Arg Ser Thr Ser Glu Ser Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Asn
    210                 215                 220

Phe Gly Thr Gln Thr Tyr Thr Cys Asn Val Asp His Lys Pro Ser Asn
225                 230                 235                 240

Thr Lys Val Asp Lys Thr Val Glu Arg Lys Cys Cys Val Glu Cys Pro
                245                 250                 255
```

Pro Cys Pro Ala Pro Val Ala Gly Pro Ser Val Phe Leu Phe Pro
                260                 265                 270

Pro Lys Pro Lys Asp Asn His His His His His
            275                 280

<210> SEQ ID NO 199
<211> LENGTH: 275
<212> TYPE: PRT
<213> ORGANISM: homosapiens

<400> SEQUENCE: 199

Met Glu Phe Gly Leu Ser Trp Val Phe Leu Val Ala Ile Leu Glu Gly
1               5                   10                  15

Val Gln Cys Glu Val Gln Leu Val Glu Ser Gly Gly Asp Leu Val Gln
            20                  25                  30

Pro Gly Gly Ser Leu Arg Leu Ser Cys Ala Ala Ser Gly Phe Thr Phe
        35                  40                  45

Gly Asn Tyr Trp Met Asn Trp Val Arg Gln Ala Pro Gly Lys Gly Leu
    50                  55                  60

Glu Trp Val Ala Asn Ile Asn Gln Asp Gly Ser Glu Lys Tyr Phe Val
65                  70                  75                  80

Asp Ser Val Lys Gly Arg Phe Thr Ile Ser Arg Asp Asn Ala Lys Lys
                85                  90                  95

Ser Phe Tyr Leu Gln Met Ser Ser Leu Arg Val Glu Asp Thr Ala Leu
            100                 105                 110

Tyr Tyr Cys Ala Arg Asp Ser Asn Val Tyr Pro Asp Thr Ser Gly Asp
        115                 120                 125

Tyr Trp Gly Gln Gly Thr Leu Val Ser Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr His His His
            260                 265                 270

His His His
    275

<210> SEQ ID NO 200
<211> LENGTH: 274
<212> TYPE: PRT
<213> ORGANISM: homosapiens

<400> SEQUENCE: 200

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Leu Val Gln
        20                  25                  30

Pro Gly Gly Ser Leu Arg Leu Ser Cys Ala Gly Ser Gly Phe Ser Phe
        35                  40                  45

Ser Ser His Thr Ile Asn Trp Val Arg Leu Ala Pro Gly Lys Gly Leu
    50                  55                  60

Gly Trp Val Ala Ala Ile Thr Gly Ser Gly Asp Thr Thr Tyr Tyr Asn
65                  70                  75                  80

Asp Ala Leu Lys Gly Arg Phe Thr Ile Ser Arg Asp Asn Ser Glu Asn
                85                  90                  95

Thr Leu Tyr Leu Gln Met Asn Ser Leu Arg Ala Glu Asp Thr Ala Leu
            100                 105                 110

Tyr Tyr Cys Ala Arg Gly Lys Gly Ala Gly Ala Trp Val Tyr Asp Leu
        115                 120                 125

Trp Gly Gln Gly Thr Leu Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr His His His His
            260                 265                 270

His His

<210> SEQ ID NO 201
<211> LENGTH: 278
<212> TYPE: PRT
<213> ORGANISM: homosapiens

<400> SEQUENCE: 201

Met Lys Phe Gly Leu Ser Trp Val Phe Leu Val Ala Leu Leu Arg Gly
1               5                   10                  15

Val Gln Cys His Met Gln Leu Val Asp Ser Gly Gly Gly Val Val Gln
        20                  25                  30

Pro Gly Arg Ser Leu Arg Leu Ser Cys Ala Ala Ser Gly Phe Thr Phe
        35                  40                  45

Ser Ser Phe Ala Ile His Trp Val Arg Gln Ala Pro Gly Lys Gly Leu
    50                  55                  60

Glu Trp Val Ala Val Ile Ala Tyr Asp Gly Lys Asn Lys Tyr Tyr Val
65                  70                  75                  80

Asp Ser Val Lys Gly Arg Phe Thr Ile Ser Arg Asp Asn Ser Lys Asn
                85                  90                  95

Thr Val Tyr Leu Gln Met Asp Ser Leu Arg Gly Glu Asp Thr Ala Val
            100                 105                 110

```
Tyr Tyr Cys Ala Lys Asp Pro Ser Ser Gly Trp Asp Asp Tyr Ser
        115                 120                 125

Ala Met Glu Val Trp Gly Gln Gly Thr Thr Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
                195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
                260                 265                 270

His His His His His His
        275

<210> SEQ ID NO 202
<211> LENGTH: 273
<212> TYPE: PRT
<213> ORGANISM: homosapiens

<400> SEQUENCE: 202

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Val Ser Gly Phe Asn Phe
        35                  40                  45

Asn Val Val Trp Met Asn Trp Val Arg Gln Ala Pro Gly Lys Gly Leu
    50                  55                  60

Glu Trp Val Gly Arg Ile Lys Gly Lys Thr Glu Ala Gly Thr Thr Glu
65                  70                  75                  80

Tyr Ala Ala Pro Met Lys Asp Arg Phe Thr Ile Ser Arg Asp Asp Ser
                85                  90                  95

Lys Ser Thr Leu Tyr Leu Gln Met Asn Ser Leu Lys Thr Gly Asp Thr
            100                 105                 110

Ala Val Tyr Tyr Cys Thr Thr Gly Phe Phe Asn Ser Gly Gly Ile Asp
        115                 120                 125

Leu Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Val Gln Ser Ser Gly Leu Tyr Ser Leu Ser Ser Val Val Thr
```

-continued

```
                195                 200                 205
Val Pro Ser Ser Asn Phe Gly Thr Gln Thr Tyr Thr Cys Asn Val Asp
    210                 215                 220
His Lys Pro Ser Asn Thr Lys Val Asp Lys Thr Val Glu Arg Lys Cys
225                 230                 235                 240
Cys Val Glu Cys Pro Pro Cys Pro Ala Pro Pro Val Ala Gly Pro Ser
                245                 250                 255
Val Phe Leu Phe Pro Pro Lys Pro Lys Asp Thr His His His His His
            260                 265                 270
His

<210> SEQ ID NO 203
<211> LENGTH: 270
<212> TYPE: PRT
<213> ORGANISM: homosapiens

<400> SEQUENCE: 203

Met Glu Phe Gly Leu Ser Trp Ile Phe Leu Val Ala Leu Leu Arg Gly
1               5                   10                  15
Val Gln Cys Gln Val His Leu Val Glu Thr Gly Gly Gly Val Val Gln
            20                  25                  30
Pro Gly Met Ser Ala Arg Leu Ser Cys Val Ala Ser Gly Phe Thr Phe
        35                  40                  45
Ser Pro Tyr Ala Met His Trp Val Arg Gln Ala Pro Gly Lys Gly Leu
    50                  55                  60
Glu Trp Val Ala Ser Met Ser Pro Asp Gly Gln Cys Tyr Phe Val Asp
65                  70                  75                  80
Ser Val Arg Gly Arg Phe Thr Met Ser Arg Asp Thr Ala Lys Asn Ser
                85                  90                  95
Leu Asp Leu Gln Met Lys Ser Leu Arg Val Glu Asp Thr Ala Val Tyr
            100                 105                 110
Ser Cys Ala Arg Asp Gln Phe Asp Trp Ser His Tyr Trp Gly Gln Gly
        115                 120                 125
Thr Leu Val Thr Val Ser Ser Ala Ser Thr Lys Gly Pro Ser Val Phe
    130                 135                 140
Pro Leu Ala Pro Cys Ser Arg Ser Thr Ser Glu Ser Thr Ala Ala Leu
145                 150                 155                 160
Gly Cys Leu Val Lys Asp Tyr Phe Pro Glu Pro Val Thr Val Ser Trp
                165                 170                 175
Asn Ser Gly Ala Leu Thr Ser Gly Val His Thr Phe Pro Ala Val Leu
            180                 185                 190
Gln Ser Ser Gly Leu Tyr Ser Leu Ser Ser Val Val Thr Val Pro Ser
        195                 200                 205
Ser Asn Phe Gly Thr Gln Thr Tyr Thr Cys Asn Val Asp His Lys Pro
    210                 215                 220
Ser Asn Thr Lys Val Asp Lys Thr Val Glu Arg Lys Cys Cys Val Glu
225                 230                 235                 240
Cys Pro Pro Cys Pro Ala Pro Pro Val Ala Gly Pro Ser Val Phe Leu
                245                 250                 255
Phe Pro Pro Lys Pro Lys Asp Thr His His His His His
            260                 265                 270

<210> SEQ ID NO 204
<211> LENGTH: 278
<212> TYPE: PRT
```

<213> ORGANISM: homosapiens

<400> SEQUENCE: 204

```
Met Glu Phe Gly Leu Ser Trp Val Phe Leu Val Ala Leu Leu Arg Gly
1               5                   10                  15
Val Gln Cys Gln Val Gln Leu Val Asp Ser Gly Gly Gly Val Val Gln
            20                  25                  30
Pro Gly Arg Ser Leu Arg Leu Ser Cys Ala Ala Ser Gly Phe Thr Phe
        35                  40                  45
Ser Ser Phe Ala Val His Trp Val Arg Gln Ala Pro Gly Lys Gly Leu
    50                  55                  60
Glu Trp Val Ala Val Ile Ala Tyr Asp Gly Asn Asn Lys Tyr Tyr Ala
65                  70                  75                  80
Asp Ser Val Lys Gly Arg Phe Thr Ile Ser Arg Asp Asn Ser Lys Asn
                85                  90                  95
Thr Val His Leu Gln Met Asn Ser Leu Arg Ala Glu Asp Thr Ala Val
            100                 105                 110
Tyr Tyr Cys Ala Lys Asp Pro Ser Ser Gly Trp Ala Asp Asp Tyr Ser
        115                 120                 125
Ala Met Glu Val Trp Gly Gln Gly Thr Thr Val Thr Val Ser Ser Ala
    130                 135                 140
Ser Thr Lys Gly Pro Ser Val Phe Pro Leu Ala Pro Cys Ser Arg Ser
145                 150                 155                 160
Thr Ser Glu Ser Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Asn Phe Gly Thr Gln Thr Tyr
    210                 215                 220
Thr Cys Asn Val Asp His Lys Pro Ser Asn Thr Lys Val Asp Lys Thr
225                 230                 235                 240
Val Glu Arg Lys Cys Cys Val Glu Cys Pro Pro Cys Pro Ala Pro Pro
                245                 250                 255
Val Ala Gly Pro Ser Val Phe Leu Phe Pro Pro Lys Pro Lys Asp Thr
            260                 265                 270
His His His His His His
        275
```

ARTIFICIALLY PRODUCED POLYCLONAL IMMUNOGLOBULIN PREPARATION

TECHNICAL FIELD

The present invention relates to an artificial polyclonal immunoglobulin composition. More specifically, the present invention relates to an artificial polyclonal immunoglobulin composition containing, as active ingredients, plural kinds of single chain variable fragments (also referred to as ScFvs) each comprised of a heavy chain variable region, heavy chain constant region 1, and hinge region (VH-CH1-hinge) of an immunoglobulin, in which the heavy chain variable regions are different each other. Further, the present invention relates to a therapeutic method for an infectious disease or an inflammatory disease, the method including administering the artificial polyclonal immunoglobulin composition according to the present invention, and to use of the artificial polyclonal immunoglobulin composition according to the present invention, in production of a pharmaceutical composition for treating an infectious disease or an inflammatory disease.

BACKGROUND ART

Immunoglobulin (Ig) is a generic term for antibodies and proteins structurally or functionally related to the antibodies. That is, when an antigen to which an immunoglobulin binds has been revealed, the immunoglobulin is called an antibody in association with the particular antigen. In a basic molecular structure of the immunoglobulin, two each of two kinds (small and large) of polypeptides, i.e., light chains (also referred to as L chains) and heavy chains (also referred to as H chains) are linked together by disulfide bonds. The heavy chain has a structure consisting of a constant region (also referred to as C region) comprised of three domains (CH1, CH2, and CH3) and a variable region (also referred to as V region) comprised of a VH domain, both regions of which is being linked together. In the immunoglobulin except IgM and IgE, there is a peptide called a hinge region between CH1 and CH2. The light chain has a structure consisting of a constant region comprised of a CL domain and a variable region comprised of a VL domain, both regions of which are being linked together. The variable regions are found to have diversity in amino acid sequence, and thus various antibodies against various antigens are produced in a living body.

A hitherto clinically used immunoglobulin preparation is a blood preparation obtained by concentrating immunoglobulins extracted from human blood, and has an action of protecting a living body by causing antigen-antibody reactions with foreign invaders such as bacteria. In recent years, the immunoglobulin preparation has been being used for, for example, idiopathic thrombocytopenic purpura, agammaglobulinemia, the acute phase of Kawasaki disease, Guillain-Barré syndrome, and Churg-Strauss syndrome as vasculitis as well as a severe infectious disease. In addition, in the treatment of those diseases, an "IVIg therapy" involving high dose intravenous administration of immunoglobulins has been frequently employed. Recently, the IVIg therapy has attracted attention as a therapeutic method for refractory vasculitis or the like, and has been internationally regarded as important as a therapeutic method for various diseases as well. In addition, the IVIg therapy has been approved for an autoimmune disease, and in association with this, the IVIg therapies have been started for connective tissue disease and myasthenia as targets in succession. Further, the IVIg therapy has a 20-year history of Kawasaki disease treatment, and has been recently approved as being more effective in single-dose administration at 2 g/kg body weight. As described above, IVIg is extremely effective for a high-severity disease and a refractory disease of unknown cause. Further, IVIg is a useful therapeutic method also because of having virtually no side effects.

There are some hypotheses about an action mechanism of the immunoglobulin preparation. One hypothesis is such that the immunoglobulin preparation contains many kinds of antibodies including antibodies against unknown antigens and thus exert pharmacological effects. Further, another hypothesis is such that antibodies against myeloperoxidase (MPO) (anti-MPO antibodies) among the many kinds of antibodies have the effects, and in particular, many kinds of anti-MPO antibodies against a wide range of epitopes of MPO exert the pharmacological effects. What is common to both the hypotheses is that the therapeutic effect is significantly contributed by the fact that the immunoglobulin preparation is a mixture of multiple immunoglobulins, i.e., polyclonal immunoglobulins. Though there are other hypotheses, the two hypotheses given as examples are each a popular one.

An immunoglobulin preparation clinically used at present is a blood preparation, and hence always involves such a risk that an unknown pathogen such as a virus derived from a raw material may be mixed therein. In fact, a blood preparation contaminated with a pathogenic virus has caused medication-related harm, becoming a serious social issue. In addition, in association with an increase in the number of diseases to be treated, a shortage of blood serving as a raw material is predicted, and hence the immunoglobulin preparation as a blood preparation is unreliable in terms of stable supply.

Under such circumstances, in order to reduce an infection risk for a patient and reveal the process of healing by the immunoglobulin preparation, there is a demand for an artificial, synthesized immunoglobulin preparation. For producing the artificial immunoglobulin preparation, the following method has been carried out. The method involves obtaining a gene of an immunoglobulin, expressing the gene by using a recombinant DNA technology, and obtaining a purified immunoglobulin. For example, a chimeric antibody obtained by replacing only a variable region of an immunoglobulin with a mouse-derived one (Japanese Patent Application Laid-open No. Hei 5-304989), and a humanized antibody obtained by replacing only a CDR region in a variable region with a mouse-derived one (Japanese Patent Application Laid-open No. 2000-14383) can each be produced by a recombinant DNA technology. The chimeric antibody and the humanized antibody have already been put to practical use as antibody drugs. Further, as a technology for expressing an immunoglobulin gene as a normal soluble protein in host cells, there is known an example in which an immunoglobulin is expressed as a fusion protein with a chaperonin (Japanese Patent Application Laid-open No. 2004-81199). However, each of those preparations comprises a single kind of immunoglobulin, i.e., a monoclonal immunoglobulin. Further, the properties of cDNA clones are not stable, and hence the quality of purified products is not stable. Thus, the immunoglobulin preparation has problems in therapeutic effect and quality control.

REFERENCE LIST

Non-Patent References

[Patent Reference 1] Japanese Patent Application No. Tokkai-Hei 5-304989.

[Patent Reference 2] Japanese Patent Application No. Tokkai 2000-14383.
[Patent Reference 3] Japanese Patent Application No. Tokkai 2004-81199.
[Patent Reference 4] Japanese Patent Application No. Tokkai 2005-312445.

SUMMARY OF INVENTION

Problem to be Solved by the Invention

An artificial immunoglobulin preparation that replaces a blood preparation has been demanded to be provided. As described above, however, the currently produced artificial immunoglobulin is a monoclonal immunoglobulin, and hence has problems in therapeutic effect and quality control of the immunoglobulin preparation.

The effect of the artificial immunoglobulin preparation is significantly contributed by the fact that the preparation is a mixture of multiple immunoglobulins, i.e., polyclonal immunoglobulins. The production of the polyclonal immunoglobulin mixture may be carried out by preparing plural kinds of recombinant vectors corresponding to multiple immunoglobulin variable regions to prepare a recombinant vector mixture, and expressing plural kinds of polypeptides corresponding to the multiple immunoglobulin variable regions in a recombinant organism to prepare a mixture of the polypeptides. However, the artificial polyclonal immunoglobulin mixture produced by such method has a problem in that the properties of purified products are not stable.

In order to solve the problem, the inventors of the present invention have devised a production method for an artificial polyclonal immunoglobulin, the method including preparing a mixture of vectors for expressing plural kinds of genes each encoding a single chain variable fragment (ScFv) comprised of a heavy chain variable region, heavy chain constant region 1, and hinge region (VH-CH1-hinge) of an immunoglobulin (Japanese Patent Application Laid-open No. 2005-312445).

A problem to be solved by the present invention is to provide an artificial polyclonal immunoglobulin composition that shows a high therapeutic effect and safety, and is capable of being supplied stably in a large amount.

In order to solve the problem, the inventors of the present invention have produced a mixture of plural kinds of single chain variable fragments (ScFvs) each comprised of a heavy chain variable region, heavy chain constant region 1, and hinge region (VH-CH1-hinge) of an immunoglobulin, in which the heavy chain variable regions are different each other, from cDNAs derived from tissues or cells expressing immunoglobulins by using a recombinant DNA technology, and have tested its effect through the use of vasculitis model mice. As a result, the inventors have found that a mixture of 204 polypeptides represented by amino acid sequences set forth in SEQ ID NOS: 1 to 204 of the sequence listing alleviates vasculitis symptoms in vasculitis model mice. Thus, the present invention has been completed.

That is, the present invention relates to the following:

1. an artificial polyclonal immunoglobulin composition, comprising, as active ingredients, polypeptides represented by amino acid sequences set forth in SEQ ID NOS: 1 to 204 of the sequence listing;
2. a pharmaceutical composition for treating an infectious disease or an inflammatory disease, comprising polypeptides represented by amino acid sequences set forth in SEQ ID NOS: 1 to 204 of the sequence listing;
3. a pharmaceutical composition for treating of vasculitis, comprising polypeptides represented by amino acid sequences set forth in SEQ ID NOS: 1 to 204 of the sequence listing;
4. a method of treating an infectious disease or an inflammatory disease, comprising administering an artificial polyclonal immunoglobulin composition comprising, as active ingredients, polypeptides represented by amino acid sequences set forth in SEQ ID NOS: 1 to 204 of the sequence listing;
5. the method according to the item 4, wherein the infectious disease or the inflammatory disease is vasculitis;
6. a use of polypeptides represented by amino acid sequences set forth in SEQ ID NOS: 1 to 204 of the sequence listing, in production of a pharmaceutical composition for treating an infectious disease or an inflammatory disease; and
7. the use according to the item 6, wherein the infectious disease or the inflammatory disease is vasculitis.

According to the present invention, there can be provided an artificial polyclonal immunoglobulin composition containing, as active ingredients, plural kinds of single chain variable fragments (ScFvs) each comprised of a heavy chain variable region, heavy chain constant region 1, and hinge region (VH-CH1-hinge) of an immunoglobulin, in which the heavy chain variable regions are different each other, the composition being produced from cDNA derived from tissues or cells expressing immunoglobulins by using a recombinant DNA technology. For example, it is possible to provide the artificial polyclonal immunoglobulin composition containing, as active ingredients, the 204 polypeptides represented by the amino acid sequences set forth in SEQ ID NOS: 1 to 204 of the sequence listing.

The artificial polyclonal immunoglobulin composition according to the present invention contains multiple immunoglobulins as with a blood-derived immunoglobulin preparation. Thus, the artificial polyclonal immunoglobulin composition according to the present invention has a high therapeutic effect, and high safety by virtue of an extremely low infection risk, and is capable of being stably supplied in a large amount. Therefore, the artificial polyclonal immunoglobulin composition according to the present invention is extremely useful for an IVIg therapy.

BRIEF DESCRIPTION OF DRAWINGS

FIG. 5-A is a graph showing that the administration of the hScFv mixture gave a decreased leukocyte count and decreased lymphocyte count in peripheral blood (Example 2). In the figure, symbol "*" indicates the presence of a significant difference (P<0.05).

FIG. 5-B is graphs showing that the administration of the hScFv mixture gave a decreased monocyte count and decreased granulocyte (neutrophil) count in peripheral blood (Example 2).

FIG. 5-C is a graph showing that the administration of the hScFv mixture gave a decreased platelet count in peripheral blood (Example 2). In the figure, symbol "*" indicates the presence of a significant difference (P<0.05).

DETAILED DESCRIPTION OF THE PRESENT INVENTION

Figure 1:
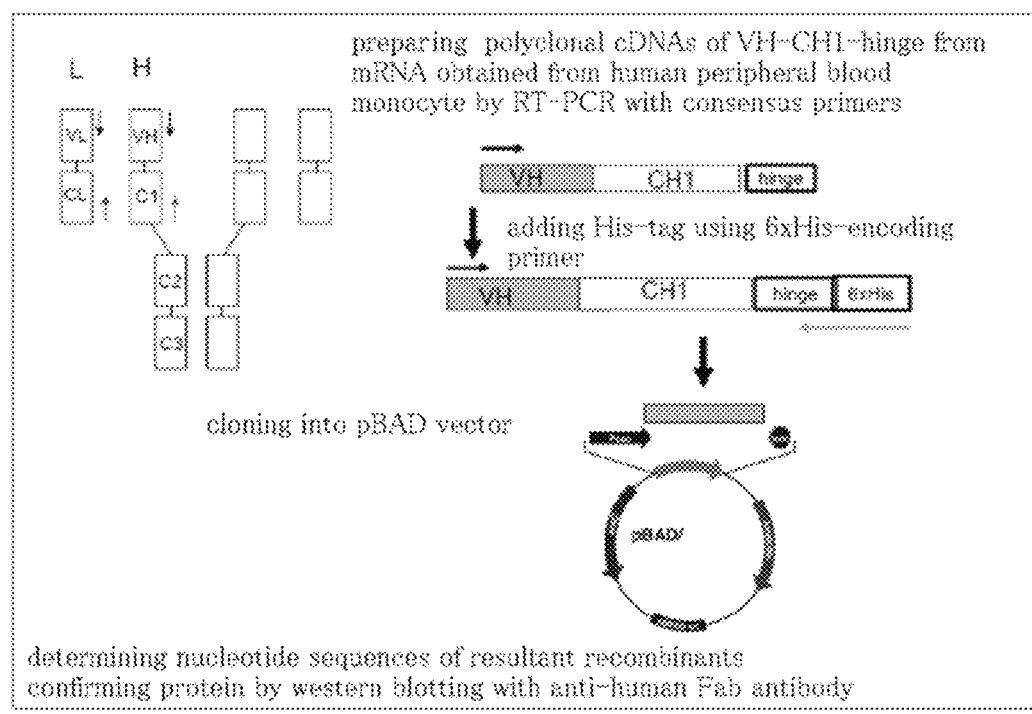
FIG. 1 is a diagram illustrating the cloning of a human single chain variable fragment (hScFv) (Example 1).

The present invention relates to an artificial polyclonal immunoglobulin composition. More specifically, the present invention relates to an artificial polyclonal immunoglobulin composition containing, as active ingredients, plural kinds of single chain variable fragments (ScFvs) each comprised of a heavy chain variable region, heavy chain constant region 1, and hinge region (VH-CH1-hinge) of an immunoglobulin, in which the heavy chain variable regions are different each other.

A polyclonal immunoglobulin composition means a composition containing plural kinds of immunoglobulins which antigen specificities are different.

The artificial polyclonal immunoglobulin composition according to the present invention is preferably an artificial polyclonal immunoglobulin composition containing, as active ingredients, 204 polypeptides represented by amino acid sequences set forth in SEQ ID NOS: 1 to 204 of the sequence listing. Each of those polypeptides is a human single chain variable fragment (hScFv) comprised of a heavy chain variable region, heavy chain constant region 1, and hinge region (VH-CH1-hinge) of a human gamma globulin, and is a polypeptide produced from RNA extracted from healthy adult peripheral blood mononuclear cells by using a recombinant cDNA technology.

The artificial polyclonal immunoglobulin composition according to the present invention may be produced as a pharmaceutical composition containing a pharmaceutically acceptable carrier (pharmaceutical carrier) as required.

Examples of the pharmaceutical carrier may include a filler, an extender, a binder, a moisture imparting agent, a disintegrating agent, a lubricant, a diluent, and an excipients, which can be generally used depending on the form of use of the pharmaceutical preparation. These can be suitably selected and used depending on the form of administration of the pharmaceutical preparation obtained. More specific examples thereof may include water, a pharmaceutically acceptable organic solvent, collagen, polyvinyl alcohol, polyvinylpyrrolidone, a carboxyvinyl polymer, sodium alginate, water-soluble dextran, sodium carboxymethylstarch, pectin, xanthan gum, gum arabic, casein, gelatin, agar, glycerin, propylene glycol, polyethylene glycol, vaseline, paraffin, stearyl alcohol, stearic acid, human serum albumin, mannitol, sorbitol, and lactose. One or a combination of two or more kinds of these carriers may be used depending on the dosage form of the composition. In addition, there may be appropriately used, for example, a stabilizing agent, a bactericide, a buffer, a tonicity adjusting agent, a chelating agent, a surfactant, and a pH adjusting agent. Examples of the stabilizing agent may include human serum albumin, a general L-amino acid, a saccharide, and a cellulose derivative. The L-amino acid is not particularly limited, and may be any of L-amino acids such as glycine, cysteine, and glutamic acid. The saccharide is also not particularly limited, and may be any of saccharides such as: a monosaccharide, e.g., glucose, mannose, galactose, or fructose; a sugar alcohol, e.g., mannitol, inositol, or xylitol; a disaccharide, e.g., sucrose, maltose, or lactose; a polysaccharide, e.g., dextran, hydroxypropylstarch, chondroitin sulfate, or hyaluronic acid; and a derivative thereof. The cellulose derivative is also not particularly limited, and may be any of cellulose derivatives such as methyl cellulose, ethyl cellulose, hydroxyethyl cellulose, hydroxypropyl cellulose, hydroxypropylmethyl cellulose, and sodium carboxymethyl cellulose. The surfactant is also not particularly limited, and any of an ionic surfactant and a nonionic surfactant may be used. Examples of the surfactant include a polyoxyethylene glycol sorbitan alkyl ester-based surfactant, a polyoxyethylene alkyl ether-based surfactant, a sorbitan monoacyl ester-based surfactant, and a fatty acid glyceride-based surfactant. Examples of the buffer may include: boric acid, phosphoric acid, acetic acid, citric acid, γ-aminocaproic acid, and glutamic acid; and/or a salt thereof (e.g., alkali metal salts thereof and alkali earth metal salts thereof, such as a sodium salt thereof, a potassium salt thereof, a calcium salt thereof, and a magnesium salt thereof). Examples of the tonicity adjusting agent may include sodium chloride, potassium chloride, saccharides, and glycerin. Examples of the chelating agent may include sodium edetate and citric acid.

Total amount of the active ingredients contained in the artificial polyclonal immunoglobulin composition according to the present invention can be suitably selected from a wide range. A suitable amount is generally within a range of approximately 0.00001 to 70 wt %, preferably approximately 0.0001 to 5 wt %.

Dosage range of the artificial polyclonal immunoglobulin composition according to the present invention is not particularly limited, and is suitably selected depending on, for example, effectiveness of the ingredients contained therein, an administration form, an administration route, the type of disease, the properties of a subject (such as a body weight, an age, a condition, and whether a subject is taking other pharmaceutical agents), and a judgment by a doctor in charge. A suitable dosage is, for example, within a range of about from 0.01 µg to 100 mg, preferably about 0.1 µg to about 1 mg, per 1 kg of body weight of the subject. However, such dosage can be altered using conventional experiments for optimization of a dosage that are well known in the art. The aforementioned dosage can be divided for administration once to several times a day. Further, as required, a large amount of the composition may be administered with reference to a dose employed in a hitherto performed IVIg therapy.

In terms of a route of administration, either systemic administration or local administration may be selected. In this case, a suitable administration route is selected depending on a disease, symptoms and the like. The composition according to the present invention may be administered by any of an oral route and a parenteral route. Examples of the parenteral route may include subcutaneous, intradermal, and intramuscular administration as well as general intravenous administration and intraarterial administration. Among them, intravenous administration is more preferred. Particularly when a large amount of the composition is administered in an IVIg therapy, the composition is preferably administered by intravenous administration.

A dosage form is not particularly limited, and various dosage forms may be adopted. For example, the composition may be used as a solution preparation, or may be lyophilized so as to be storable and then dissolved at time of use in, for example, water, a buffer solution containing physiological saline, or the like so as to be prepared at an appropriate concentration before use. Further, the dosage form may be a sustained dosage form or an extended release dosage form.

Specific examples of the parenteral drug may include, but not limited to, injections such as an intravenous injection, a subcutaneous injection, an intramuscular injection, and an intraperitoneal injection, a patch, ointment, and lotion for transdermal administration, sublingual medicine and a patch for application to oral-cavity mucosa for buccal administration, an aerosol for transnasal administration, and a suppository. For oral administration, the following forms may be adopted: a tablet, a capsule, a powder, a granule, a pill, a liquid, an emulsion, a suspension, a solution, a spirit, a syrup, an extract, and an elixir. Those preparations may be produced by a known method generally employed in a formulation process.

In the case of preparing the injection, subcutaneous, intramuscular, and intravenous injections can be produced by a conventional method through the addition of a pH adjusting agent, a buffer, a stabilizing agent, a tonicity adjusting agent, a local anesthetic, and the like to the above-mentioned compound. In such a case, examples of the pH adjusting agent and the buffer may include sodium citrate, sodium acetate, and sodium phosphate. Examples of the stabilizing agent may include sodium pyrosulfite, ethylenediamine tetraacetic acid (EDTA), thioglycolic acid, and thiolactic acid. Examples of the local anesthetic may include procaine hydrochloride and lidocaine hydrochloride. Examples of the tonicity adjusting agent may include sodium chloride and glucose.

In the case of preparing a solid preparation for oral administration, a tablet, a coated tablet, a granule, a powder, a capsule, and the like can be produced by a conventional method after the addition of an excipient and as required, a binder, a disintegrating agent, a lubricant, a colorant, a taste masking agent, an odor masking agent, and the like to the above-mentioned active ingredients. An additive generally used in the field can be used as such additive. Examples of the excipient may include lactose, white soft sugar, sodium chloride, glucose, starch, calcium carbonate, kaolin, microcrystalline cellulose, and silicic acid. Examples of the binder may include water, ethanol, propanol, a simple syrup, a glucose solution, a starch solution, a gelatin solution, carboxymethyl cellulose, hydroxypropyl cellulose, hydroxypropylstarch, methyl cellulose, ethyl cellulose, shellac, calcium phosphate, and polyvinylpyrrolidone. Examples of the disintegrating agent may include dry starch, sodium alginate, powdered agar, sodium hydrogen carbonate, calcium carbonate, sodium lauryl sulfate, stearic acid monoglyceride, and lactose. Examples of the lubricant include purified talc, a stearate, borax, and polyethylene glycol. Examples of the taste masking agent may include white soft sugar, bitter orange peel, citric acid, and tartaric acid.

In the case of preparing a liquid preparation for oral administration, an internal liquid, a syrup, an elixir, and the like can be produced by a conventional method through the addition of a taste masking agent, a buffer, a stabilizing agent, an odor masking agent, and the like to the above-mentioned compound. In such a case, examples of the taste masking agent may include the above-mentioned agents, examples of the buffer may include sodium citrate, and examples of the stabilizing agent may include tragacanth, gum arabic, and gelatin.

The artificial polyclonal immunoglobulin composition according to the present invention is useful for the treatment of a disease for which a therapy by immunoglobulin administration, e.g., IVIg is effective. Examples of such disease may include an infectious disease, an inflammatory disease, idiopathic thrombocytopenic purpura, agammaglobulinemia, the acute phase of Kawasaki disease, Guillain-Barré syndrome, and Churg-Strauss syndrome as vasculitis, preferably an infectious disease and an inflammatory disease, more preferably vasculitis. The indications of the artificial polyclonal immunoglobulin composition according to the present invention are not limited to those diseases, and the composition is applicable to any disease as long as the disease is a disease for which an immunoglobulin preparation is effective.

The present invention further provides a therapeutic method for an infectious disease or an inflammatory disease, the method including administering the artificial polyclonal immunoglobulin composition according to the present invention.

The present invention also provides the use of the polypeptides represented by the amino acid sequences set forth in SEQ ID NOS: 1 to 204 of the sequence listing, in the production of a pharmaceutical composition for the therapy of an infectious disease or an inflammatory disease.

The polypeptides as the active ingredients of the artificial polyclonal immunoglobulin composition according to the present invention may be produced by, for example, using a recombinant DNA technology. Specifically, the polypeptides may be produced by: first mixing plural kinds of genes encoding the plural kinds of the polypeptides; contacting the resultant gene mixture with appropriate vectors to make it incorporate therein; transfecting the resultant mixture of recombinant vectors into an appropriate host; culturing the resultant transformants to express the plural kinds of genes; and collecting a mixture of the polypeptides encoded by the genes from the culture, followed by purification.

A vector is not particularly limited as long as the vector is replicable on a host, and it is suitably selected depending on the kind of host and intended use. The vector may be obtained by extracting naturally existing vectors, or may be one in which one part of DNA segment other than a segment necessary for replication has been deleted. Representative examples thereof may include vectors derived from a plasmid, a bacteriophage, and a virus. The plasmid may be exemplified by a plasmid derived from *Escherichia coli*, a plasmid derived from *Bacillus subtilis*, and a plasmid derived from yeast. The bacteriophage may be exemplified by λ phage. The vector derived from a virus may be exemplified by vectors derived from animal viruses such as a retrovirus, a vaccinia virus, an adenovirus, a papovavirus, SV40, a fowlpox virus, and a pseudorabies virus, or vectors derived from insect viruses such as a baculovirus. Other examples of the vectors may include a vector derived from a transposon, a vector derived from an insertion element, and a vector derived from yeast chromosomal element. Alternatively, for example, there may be given a vector produced by combining those materials, such as a vector produced by combining genetic elements of a plasmid and a bacteriophage (such as a cosmid or a phagemid).

A vector is required to have a target gene that is incorporated in such a way as to allow the function of the gene to appear, and contains at least the target gene sequence and a promoter as components thereof. In addition to these components, as desired, one or more genetic sequences in combination selected from genetic sequences that encode information relating to replication and regulation, may be incorporated into the vector by using a well-known method. Such genetic sequences can be exemplified by a ribosome binding sequence, terminator, signal sequence, cis element such as an enhancer, splicing signal, and a selective marker.

A selective marker can be exemplified by dihydrofolate reductase gene, ampicillin-resistant gene and neomycin-resistant gene.

As a method of incorporating the target gene sequence into the vector, any known method can be employed. For example, a method may be used which comprises treating the target gene sequence with suitable restriction enzymes to cleave it at specific sites, and then mixing it with a similarly treated vector DNA for ligation using a ligase. Alternatively, a desired recombinant vector can also be obtained by ligating a suitable linker to the target gene sequence, and then inserting it into the multi-cloning site of a vector suitable for the desired purpose.

Both prokaryotes and eukaryotes can be used as a host. Examples of the prokaryote include bacteria belonging to the *Escherichia* genus, such as, *Escherichia coli*, bacteria belonging to the *Bacillus* genus, such as, *Bacillus subtilis*, bacteria belonging to the *Pseudomonas* genus, such as, *Pseudomonas putida*, and bacteria belonging to the *Rhizobium* genus, such as, *Rhizobium meliloti*. Examples of the eukaryote include yeasts such as *Saccharomyces cerevisiae* and *Schizosaccharomyces pombe*, insect cells such as Sf9 and Sf21, and animal cells such as monkey kidney-derived cells, (COS cells, Vero cells), Chinese hamster ovary cells (CHO cells), mouse L cells, rat GH3 cells, human FL cells or 293 EBNA cells, and *Xenopus laevis* oocyte.

Introduction of a vector into a host cell can be performed according to a known method, for example, by applying a standard method described in publications (Sambrook et al., Eds., "Molecular Cloning, A Laboratory Manual, 2nd Edition", 1989, Cold Spring Harbor Laboratory). When gene stability is a consideration, it is preferable to use a method that integrates the gene onto a chromosome. Meanwhile, it is convenient to use an autonomous replication system that utilizes an extranuclear gene. Specifically, calcium phosphate transfection, DEAE-dextran mediated transfection, microinjection, cationic lipid-mediated transfection, electroporation, transduction, scrape loading, ballistic introduction, infection, and the like, may be mentioned.

The polypeptides as the active ingredients of the artificial polyclonal immunoglobulin composition according to the present invention are each a fusion protein containing a heavy chain variable region (VH) and part of a heavy chain constant region (CH1) of an immunoglobulin. The heavy chain constant region of an antibody contributes to the stability of the antibody, and hence the polypeptides according to the present invention can provide an artificial polyclonal immunoglobulin composition having higher stability and a longer half-life in blood.

Thus, the polypeptides as the active ingredients of the artificial polyclonal immunoglobulin composition according to the present invention can be produced using *Escherichia coli* as host cells, and hence mass culture can be easily applied to the production. The polypeptides according to the present invention can be produced simply and in large amounts, and hence ensure stable supply thereof in large amounts.

The artificial polyclonal immunoglobulin composition according to the present invention contains multiple immunoglobulins as with a blood-derived immunoglobulin preparation. Thus, the artificial polyclonal immunoglobulin composition has an effect similar to that of a conventional immunoglobulin preparation. Further, as the artificial polyclonal immunoglobulin composition is artificially produced, the composition does not contain microorganisms such as a virus, resulting in an extremely low infection risk and very high safety.

Hereinafter, the present invention is more specifically described by way of examples. The present invention is by no means limited to the examples shown below. In the following examples, the collection of blood samples used for extracting immunoglobulin genes in all the cases was performed after the confirmation of the willingness of blood donors through informed consent.

Example 1

Cloning of human artificial gamma globulins, and mass culture and protein purification thereof were performed. As the human artificial gamma globulins, human single chain variable fragments (hScFvs) were produced, each of which were comprised of a heavy chain variable region, heavy chain constant region 1, and hinge region (VH-CH-hinge) of a human gamma globulin, by the method described in Japanese Patent Application Laid-open No. 2005-312445.

1. Cloning of hScFvs (FIG. 1)

Peripheral blood mononuclear cells (MNC) were isolated from peripheral blood of 20 healthy adults who gave informed consent, and total RNA was extracted therefrom and pooled by ordinary methods. Primers were made using consensus sequences at the 5' end of VH and the 3' end of a hinge region. Reverse transcription polymerase chain reaction (RT-PCT) was performed with the total RNA as a template and the consensus primers to afford polyclonal cDNAs encoding VH-CH1-hinge. The DNAs were added with a six histidine tag-encoding sequence at their 3' end by using a 3' end side primer having a sequence encoding six histidines added at the 3' end, and were added with a sequence of 16 nucleotides homologous to the vector at their 5' end. The cDNAs were incorporated into a pBAD vector by homologous recombination with an In-Fusion system to transform *Escherichia coli* by a heat shock method. 1,000 Clones of colonies of transformed bacteria capable of growing on an ampicillin-containing selective medium were picked up, from each of which plasmid DNA was extracted, and the nucleotide sequence of the cDNA being incorporated into the vector was determined through analysis by the Sanger method with a fluorescent terminator. Further, proteins were extracted from bacterial cells of each of the clones and were applied to sodium dodecyl sulfate-polyacrylamide gel electrophoresis (SDS-PAGE), which was followed by Western blotting with an anti-human Fab antibody to confirm whether or not VH-CH1-hinge was synthesized as a protein. Through sequence analysis, among 272 clones capable of expressing VH-CH1-hinge polypeptides, duplicate clones and clones whose VH-CH1-hinge structures had been broken (21 clones having undesired structures and 46 duplicate clones) were removed. Thus, 204 clones having unique sequences were finally obtained. Those clones were mixed to express recombinant proteins.

2. Mass Culture and Protein Purification of hScFvs

The clones expressing VH-CH1-hinge proteins obtained by the cloning were mixed in 500 ml of LB medium and cultured at 37° C. for 16 hours, and was added with glycerol at a final concentration of 15%. The resultant was dispensed into tubes at 10 ml each, cryopreserved at −80° C., and used as a master mix seed. The master mix seed that had been dissolved was added to 5 L of LB medium, and cultured at 37° C. for 6 hours. When OD600 reached 0.4 to 0.6, arabinose was added at 0.002% for the induction of expression. The resultant was further cultured at 37° C. for 16 hours, and bacterial cells were collected by centrifugation. The resultant bacterial cells were suspended in a Tris-ethylenediamine tetraacetic acid (Tris-EDTA) buffer (pH 8.0) and were added with Deoxycholic acid and lysozyme. The mixture was stirred at 37° C. to solubilize the bacterial cells. DNase I was further added to degrade the DNA of *Escherichia coli*, and the resultant was sufficiently solubilized by ultrasonication. The resultant suspension was subjected to high-speed centrifugation to collect a precipitated insoluble fraction (inclusion body). The insoluble fraction was washed with 3 M urea and collected by centrifugation. After that, the insoluble fraction was suspended in 8 M urea and left to stand at room temperature for one day and night to solubilize proteins of interest. The insoluble fraction was removed by high-speed centrifugation, and the supernatant was subjected to chromatography with a nickel chelate column (His-trap), to thereby isolate the proteins of interest. For further purification, the proteins were subjected to nickel chelate column (His-trap) chromatography again to be highly purified.

3. Removal (Reduction) of Endotoxin

The resultant purified proteins were found to include an endotoxin. In order to remove the endotoxin, the protein solution was dialyzed against a buffer obtained by rendering 6 M guanidine hydrochloride strongly alkaline, and was left to stand under the strongly alkaline condition for 3 days and nights to promote the hydrolysis of the endotoxin. Then, the degradation product was removed by 10K pore ultrafiltration. Thus, the endotoxin was reduced.

4. Results

There were obtained 204 clones encoding 204 different polypeptides represented by amino acid sequences set forth in SEQ ID NOS: 1 to 204 of the sequence listing. That is, 204 different hScFvs were obtained. The concentration of the endotoxin contained in the purified preparation obtained by purifying the mixture of the 204 different hScFvs was 10 to 5 ng/1 mg hScFv.

Example 2

The mixture comprised of plural kinds of hScFvs produced in Example 1 was investigated for the therapeutic effect on vasculitis by using SCG/Kj mice as spontaneous vasculitis model mice. The hScFv mixture used comprises 204 different polypeptides represented by amino acid sequences set forth in SEQ ID NOS: 1 to 204 of the sequence listing. The hScFv mixture was dissolved in 1.5% D-mannitol containing 0.45 M arginine (Arg), 0.45% glycine (Gly), and 0.9% sodium chloride before use.

Figure 2:
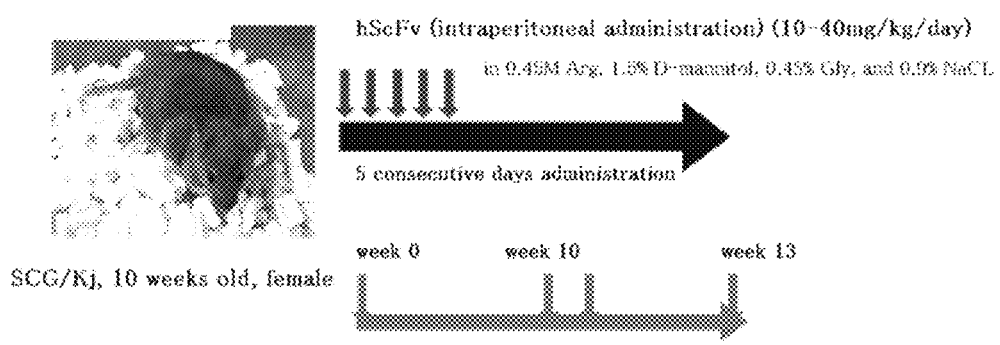
FIG. 2 is a diagram illustrating a schedule according to which the therapeutic effect of a mixture comprised of plural kinds of hScFvs was tested with SCG/Kj mice as spontaneous vasculitis model mice (Example 2).

First, the hScFvs were administered to 10-week-old SCG/Kj mice for five consecutive days at a dose of 10 to 40 mg/Kg/day through intraperitoneal administration (ip). At 13 weeks old, the mice were euthanized with $CO_2$ gas, and were each measured for its myeloperoxidase-specific anti-neutrophil cytoplasmic antibody (MPO-ANCA) level in serum as an indicator for vasculitis, spleen weight, and leukocyte count, lymphocyte count, monocyte count, granulocyte (neutrophil) count, and platelet count in peripheral blood. The therapeutic effect was evaluated based on the results of the measurements (FIG. 2).

Figure 3:
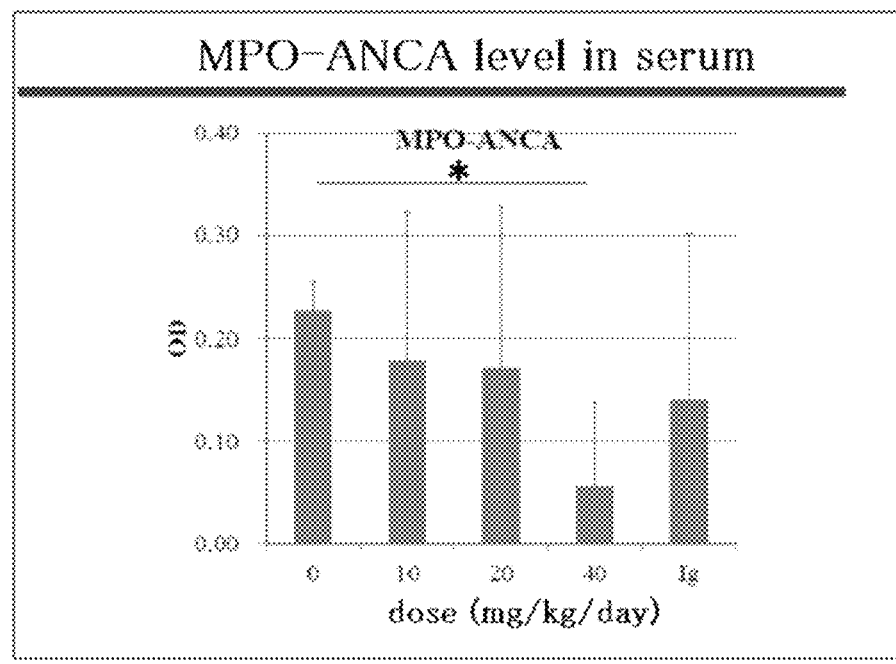
FIG. 3 is a graph showing that the administration of the hScFv mixture gave a reduction in MPO-ANCA level in serum as an indicator for vasculitis (Example 2). In the figure, symbol "*" indicates the presence of a significant difference (P<0.05).
Figure 4:
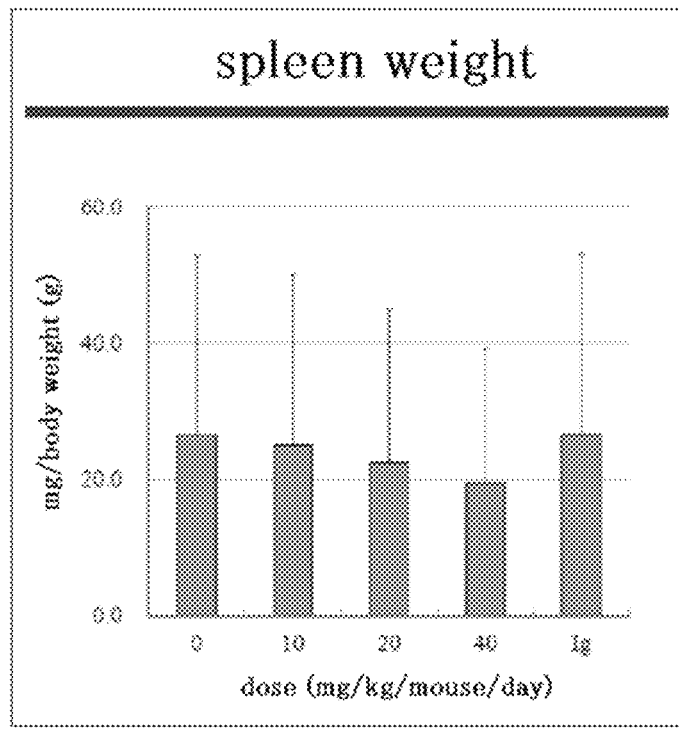
FIG. 4 is a graph showing that the administration of the hScFv mixture gave a decreasing tendency of a spleen weight (Example 2).

It was observed that the administration of the hScFv mixture gave a reduction in the MPO-ANCA level in serum that is an indicator for vasculitis (FIG. 3). Further, a decreasing tendency of the spleen weight was observed (FIG. 4). In addition, the leukocyte count, lymphocyte count, monocyte count, granulocyte (neutrophil) count, and platelet count in peripheral blood decreased (FIGS. 5-A, 5-B, and 5-C). The above-mentioned results confirmed the therapeutic effect of the hScFv mixture.

The present invention is extremely useful in a medical field concerning diseases for which a therapy by immunoglobulin administration, e.g., IVIg, is effective, such as an infectious disease, an inflammatory disease, idiopathic thrombocytopenic purpura, agammaglobulinemia, the acute phase of Kawasaki disease, Guillain-Barré syndrome, and Churg-Strauss syndrome as vasculitis.

---

What is claimed is:

1. An artificial polyclonal immunoglobulin composition, comprising, as active ingredients, polypeptides represented by amino acid sequences set forth in SEQ ID NOS: 1 to 204 of the sequence listing.

2. A pharmaceutical composition for treating an inflammatory disease, comprising polypeptides represented by amino acid sequences set forth in SEQ ID NOS: 1 to 204 of the sequence listing.

3. A pharmaceutical composition for treating vasculitis, comprising polypeptides represented by amino acid sequences set forth in SEQ ID NOS: 1 to 204 of the sequence listing.

4. A method of treating an infectious disease or an inflammatory disease, comprising administering an artificial polyclonal immunoglobulin composition comprising, as active ingredients, polypeptides represented by amino acid sequences set forth in SEQ ID NOS: 1 to 204 of the sequence listing.

5. The method according to claim 4, wherein the infectious disease or the inflammatory disease is vasculitis.

* * * * *